(12) United States Patent
Wickersham et al.

(10) Patent No.: US 11,866,391 B2
(45) Date of Patent: Jan. 9, 2024

(54) ANESTHETIC COMPOUNDS AND METHODS OF MAKING AND USING SAME TO TREAT OR PREVENT PAIN SYMPTOMS

(71) Applicant: PTC Innovations, LLC, San Antonio, TX (US)

(72) Inventors: Pendleton Wickersham, San Antonio, TX (US); Stephen Bendel, Las Cruces, NM (US); Todd Mathis, San Antonio, TX (US); Christian Warren, Larkspur, CO (US)

(73) Assignee: PTC Innovations, LLC, San Antonio, TX (US)

( * ) Notice: Subject to any disclaimer, the term of this patent is extended or adjusted under 35 U.S.C. 154(b) by 0 days.

(21) Appl. No.: 18/358,931

(22) Filed: Jul. 25, 2023

(65) Prior Publication Data

US 2023/0399290 A1     Dec. 14, 2023

Related U.S. Application Data

(63) Continuation of application No. 18/180,344, filed on Mar. 8, 2023.

(60) Provisional application No. 63/317,868, filed on Mar. 8, 2022.

(51) Int. Cl.
| C07C 233/29 | (2006.01) |
| A61K 31/16 | (2006.01) |
| A61K 45/06 | (2006.01) |

(52) U.S. Cl.
CPC ............ *C07C 233/29* (2013.01); *A61K 45/06* (2013.01)

(58) Field of Classification Search
CPC .............................. C07C 233/29; A61K 31/16
USPC .......................................... 564/163; 514/619
See application file for complete search history.

(56) References Cited

U.S. PATENT DOCUMENTS

| 4,310,429 A | 1/1982 | Lai |
| 4,489,186 A | 12/1984 | Sugio et al. |
| 5,244,898 A | 9/1993 | Ogawa et al. |
| 5,258,510 A | 11/1993 | Ogawa et al. |
| 5,336,800 A | 8/1994 | Siegel et al. |
| 5,382,590 A | 1/1995 | Bourzat et al. |
| 5,389,682 A | 2/1995 | Tait et al. |
| 5,447,916 A | 9/1995 | Spellmeyer et al. |
| 5,475,106 A | 12/1995 | Bourzat et al. |
| 5,480,871 A | 1/1996 | Spellmeyer et al. |
| 5,494,926 A | 2/1996 | Owens et al. |
| 5,559,230 A | 9/1996 | Ogawa et al. |
| 5,753,677 A | 5/1998 | Ogawa et al. |
| 5,830,854 A | 11/1998 | Hargreaves |
| 5,985,869 A | 11/1999 | Ogawa et al. |
| 6,103,761 A | 8/2000 | Tait et al. |
| 6,159,482 A | 12/2000 | Tuloup et al. |
| 6,326,014 B1 | 12/2001 | Tuloup et al. |
| 6,350,761 B1 | 2/2002 | Guilford et al. |
| 6,420,396 B1 | 7/2002 | Albers et al. |
| 6,610,749 B2 | 8/2003 | Liao et al. |
| 6,677,333 B1 | 1/2004 | Seko et al. |
| 6,677,360 B2 | 1/2004 | Albers et al. |
| 6,743,788 B2 | 6/2004 | Cirillo et al. |
| 7,049,911 B2 | 8/2006 | Albers et al. |
| 7,172,631 B2 | 2/2007 | Plos et al. |
| 7,189,266 B2 | 3/2007 | Plos et al. |
| 7,261,743 B2 | 8/2007 | Plos et al. |
| 7,265,133 B2 | 9/2007 | Mammen et al. |
| 7,456,199 B2 | 11/2008 | Mammen et al. |
| 7,491,718 B2 | 2/2009 | Comess et al. |
| 7,642,355 B2 | 1/2010 | Mu et al. |

(Continued)

FOREIGN PATENT DOCUMENTS

| AU | 9170939 A | 5/1991 |
| EP | 3666769 A1 | 6/2020 |

(Continued)

OTHER PUBLICATIONS

US 5,889,182 A, 03/1999, Dezube et al. (withdrawn)

(Continued)

*Primary Examiner* — Raymond J Henley, III
(74) *Attorney, Agent, or Firm* — Incubate IP; Randy R. Micheletti

(57) ABSTRACT

The present disclosure provides compounds useful as anesthetics, such as topical anesthetics, of general formula (VIIIk):

(VIIIk)

wherein:
$R_2$=H or Me;
$R_3$=H or Me;
$R_4$=Alkyl;
$R_5$=O-Alkyl; and
Alkyl=aliphatic $C_1$-$C_4$ alkyl.

The present disclosure further provides methods of making compounds of general formula (VIIIk), compositions comprising a therapeutically effective amount of a compound of general formula (VIIIk), and methods of treating or preventing pain in a subject by administering (e.g., topically applying) compositions comprising an effective amount of a compound of general formula (VIIIk) to the subject.

20 Claims, 18 Drawing Sheets

(56) References Cited

U.S. PATENT DOCUMENTS

| | | |
|---|---|---|
| 7,795,315 B2 | 9/2010 | Chen et al. |
| 7,851,632 B2 | 12/2010 | Mammen et al. |
| 7,858,795 B2 | 12/2010 | Mammen et al. |
| 8,030,487 B2 | 10/2011 | Noronha et al. |
| 8,329,911 B2 | 12/2012 | Mu et al. |
| 8,394,965 B2 | 3/2013 | Mauduit et al. |
| 8,466,161 B2 | 6/2013 | Lee et al. |
| 8,586,757 B2 | 11/2013 | Mauduit et al. |
| 8,853,240 B2 | 10/2014 | Menet et al. |
| 9,198,420 B2 | 12/2015 | Hopkins et al. |
| 9,415,037 B2 | 8/2016 | Menet et al. |
| 9,505,754 B2 | 11/2016 | Menet et al. |
| 2004/0068012 A1 | 4/2004 | Comess et al. |
| 2004/0087582 A1 | 5/2004 | Dorsch et al. |
| 2004/0157836 A1 | 8/2004 | Comess et al. |
| 2005/0113426 A1 | 5/2005 | Liao et al. |
| 2006/0139425 A1 | 6/2006 | Tsuchimura et al. |
| 2007/0098816 A1 | 5/2007 | Nakanishi et al. |
| 2008/0221127 A1 | 9/2008 | Lin et al. |
| 2009/0264412 A1 | 10/2009 | Kampen et al. |
| 2010/0093998 A1 | 4/2010 | Isobe et al. |
| 2011/0028715 A1 | 2/2011 | Isobe et al. |

FOREIGN PATENT DOCUMENTS

| | | |
|---|---|---|
| JP | 11180964 A | 7/1999 |
| JP | 11269146 A | 10/1999 |
| WO | 97/29121 A1 | 8/1997 |
| WO | 97/45115 A1 | 12/1997 |
| WO | 2000/035864 A1 | 6/2000 |
| WO | 2009/000558 A1 | 12/2008 |
| WO | 2017/213137 A1 | 12/2017 |
| WO | 2022/026548 A1 | 2/2022 |

OTHER PUBLICATIONS

Alles et al., "Etiology and Pharmacology of Neuropathic Pain," *Pharm. Rev.*, vol. 70, pp. 315-347 (2018), 33 pages.

Danzinger et al., "Automated site-directed drug design: a general algorithm for knowledge acquisition about hydrogen-bonding regions at protein surfaces," *Proc. R. Soc. Lond.*, vol. 236, pp. 101-113 (1989), 14 pages.

Hirst et al., "Conversion of acyclic nonpeptide CCK antagonists into CCK agonists," *Bioorg. & Med. Chem. Lett.*, vol. 7(5), pp. 511-514 (1997), 4 pages.

ANESTHETIC COMPOUNDS AND METHODS OF MAKING AND USING SAME TO TREAT OR PREVENT PAIN SYMPTOMS

PRIORITY CLAIM

This application is a continuation of U.S. patent application Ser. No. 18/180,344, filed on Mar. 8, 2023, which claims priority to U.S. Provisional Patent Application Ser. No. 63/317,868, filed on Mar. 8, 2022, the entire contents of each of which are incorporated herein by reference.

FIELD

The present disclosure provides compounds useful as anesthetic agents, methods of making same, compositions comprising same, and methods of treating or preventing pain using same.

BACKGROUND

Anesthetic agents are commonly used to treat or prevent pain sensations. However, certain classes of anesthetics encourage overuse, abuse, and/or overprescribing. Other agents are potent, but provide low bioavailability for example when administered topically.

A need persists for improved anesthetic agents, especially agents that are effective when applied topically to skin of a subject.

SUMMARY

In one embodiment, the present disclosure provides a compound of formula (I):

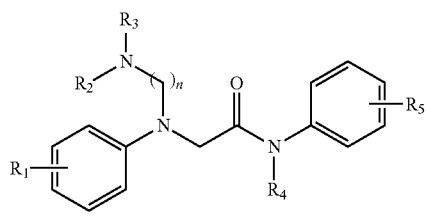

wherein:
$R_1$ is H, —OMe, Me, or one or more electron withdrawing groups;
$R_2$ and $R_3$ are each independently H or alkyl or, taken together, form a 4- to 8-membered heterocyclic ring with the adjacent nitrogen atom;
$R_4$ is H or alkyl;
$R_5$ is H or one or more electron donating groups; and
n is 1 to 4.

In other embodiments, the present disclosure provides a compound of formula (II):

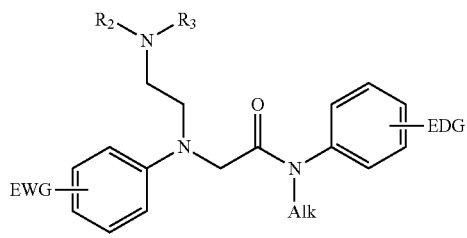

wherein:
EWG is one or more electron withdrawing groups selected from the group consisting of: Cl, F, $CF_3$, and $OCF_3$;
$R_2$ and $R_3$ are each independently H or alkyl;
Alk is an aliphatic carbon group consisting of 1 to 6 carbon atoms; and
EDG is one or more alkoxy or alkyl electron donating groups.

In other embodiments, the present disclosure provides a compound of formula (III):

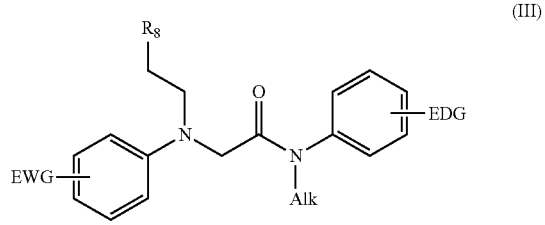

wherein:
EWG is one or more electron withdrawing groups selected from the group consisting of: Cl, F, $CF_3$, and $OCF_3$;
$R_8$ is selected from the group consisting of:
—$NH_2$, —N(H)Alk, —N(Alk)$_2$,

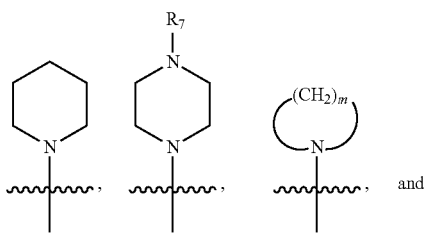

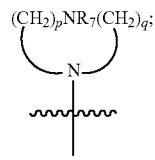

$R_7$ is H or alkyl;
m is 3 to 6;
p is 1 to 4;
q is 1 to 4;
p+q is 3 to 6;
each Alk is independently an aliphatic carbon group consisting of 1 to 6 carbon atoms; and
EDG is one or more alkoxy or alkyl electron donating groups.

In other embodiments, the present disclosure provides a compound of formula (IV):

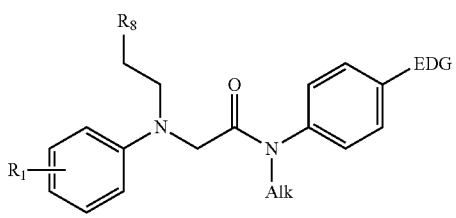

(IV)

wherein:

R$_1$ is H, Cl, F, —CF$_3$, —OCF$_3$, or —OMe;

R$_8$ is selected from the group consisting of:
—NH$_2$, —N(H)Alk, —N(Alk)$_2$,

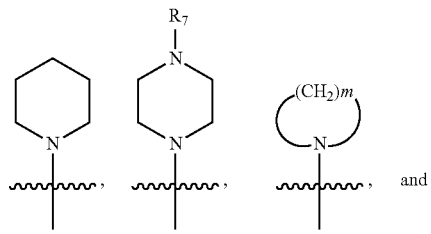

R$_7$ is H or alkyl;

m is 3 to 6;

p is 1 to 4;

q is 1 to 4;

p+q is 3 to 6;

each Alk is independently an aliphatic carbon group consisting of 1 to 6 carbon atoms; and EDG is one or more amino, aryl, acylamido, acyloxy, alkoxy or alkyl electron donating groups.

In other embodiments, the present disclosure provides a compound of formula (V):

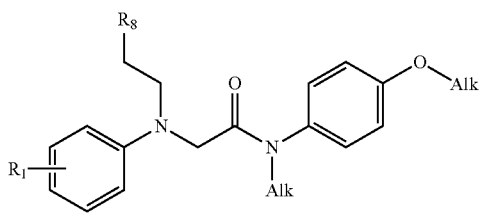

(V)

wherein:

R$_1$ is H, Cl, F, —CF$_3$, —OCF$_3$, or —OMe;

R$_8$ is selected from the group consisting of:
—NH$_2$, —N(H)Alk, —N(Alk)$_2$,

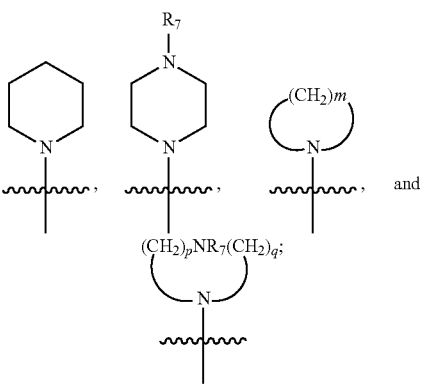

R$_7$ is H or alkyl;

m is 3 to 6;

p is 1 to 4;

q is 1 to 4;

p+q is 3 to 6; and each Alk is independently an aliphatic carbon group consisting of 1 to 6 carbon atoms.

In other embodiments, the present disclosure provides a compound of formula (VI):

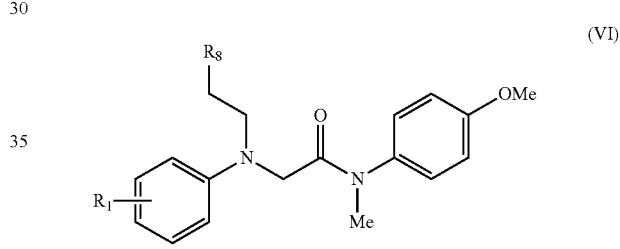

(VI)

wherein:

R$_1$ is H, Cl, F, —CF$_3$, —OCF$_3$, —OMe, or methyl;

R$_8$ is selected from the group consisting of:
—NH$_2$, —N(H)Alk, —N(Alk)$_2$,

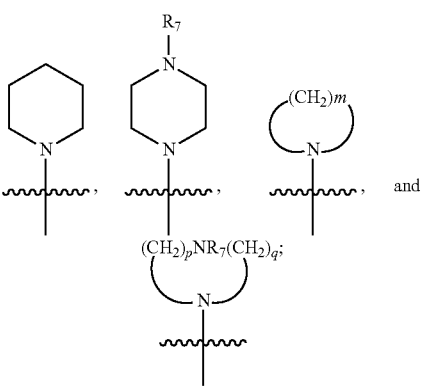

R$_7$ is H or alkyl;

m is 3 to 6;

p is 1 to 4;

q is 1 to 4;

p+q is 3 to 6; and each Alk is independently an aliphatic carbon group consisting of 1 to 6 carbon atoms.

In other embodiments, the present disclosure provides a compound of formula (VII):

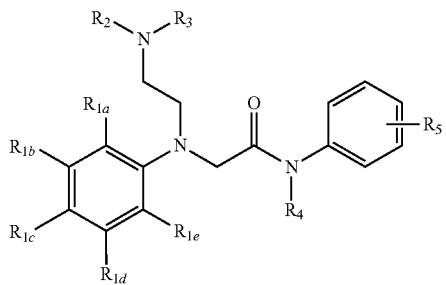
(VII)

wherein:
R$_{1a}$ is H, Cl, F, —CF$_3$, —OMe, or methyl;
R$_{1b}$ is H, Cl, F, —CF$_3$, or —OCF$_3$;
R$_{1c}$ is H, Cl, F, or —OMe;
R$_{1d}$ is H, Cl, F, —CF$_3$, or —OCF$_3$;
R$_{1e}$ is H, Cl, F, —CF$_3$, —OMe, or methyl;
R$_2$ and R$_3$ are each independently H or alkyl or, taken together, form a 4- to 8-membered heterocyclic ring with the adjacent nitrogen atom;
R$_4$ is H or alkyl; and
R$_5$ is H or one or more electron donating groups.

In other embodiments, the present disclosure provides a compound of formula (VIIIa):

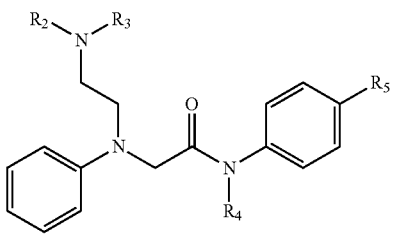
(VIIIa)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIb):

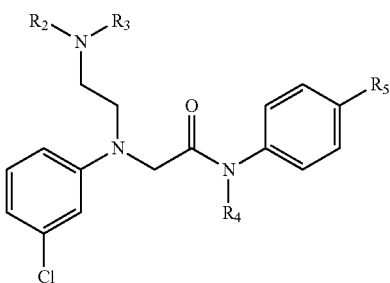
(VIIIb)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIc):

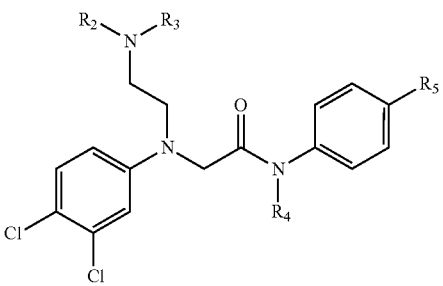
(VIIIc)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIId):

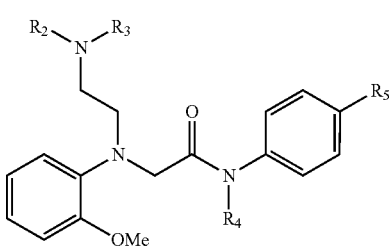
(VIIId)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIe):

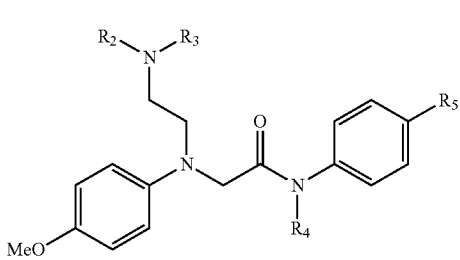
(VIIIe)

wherein:
R$_2$=H or Me;
R$_3$=H or Me;

R$_4$=Alkyl;
R$_5$=O-Alkyl; and
Alkyl=aliphatic C$_1$-C$_4$ alkyl.

In other embodiments, the present disclosure provides a compound of formula (VIIIf):

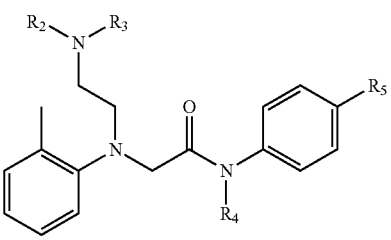

(VIIIf)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIg):

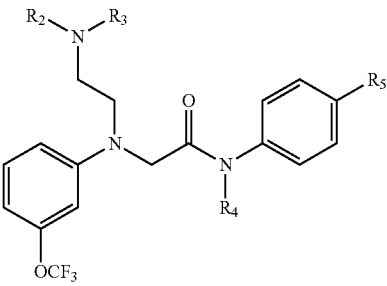

(VIIIg)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIh):

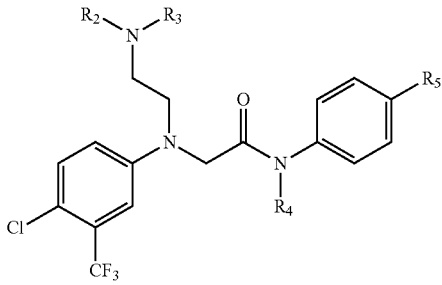

(VIIIh)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIi):

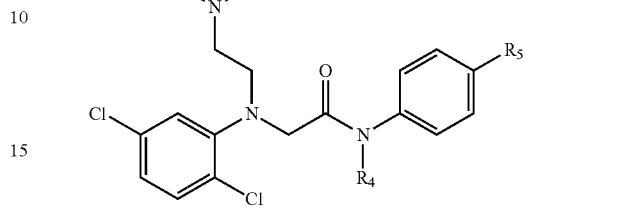

(VIIIi)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIj):

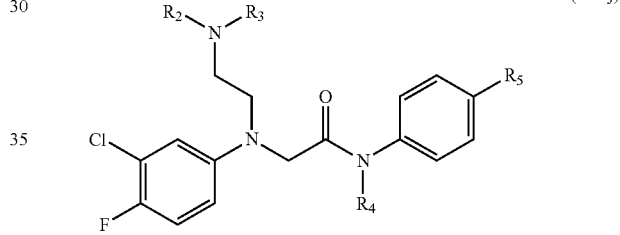

(VIIIj)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIk):

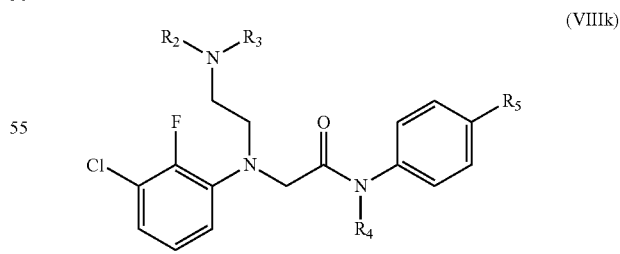

(VIIIk)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In other embodiments, the present disclosure provides a compound of formula (VIIIm):

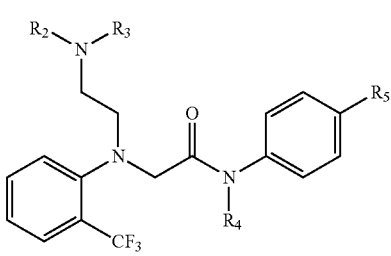

(VIIIm)

wherein:
R₂=H or Me;
R₃=H or Me;
R₄=Alkyl;
R₅=O-Alkyl; and
Alkyl=aliphatic C₁-C₄ alkyl.

In other embodiments, the present disclosure provides a compound of formula (VIIIn):

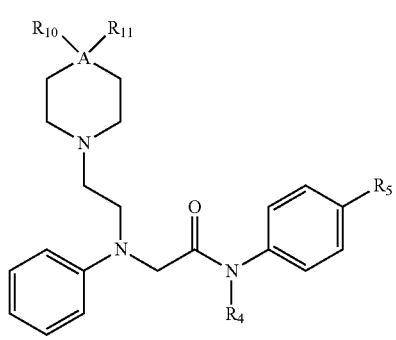

(VIIIn)

wherein:
A=C or N;
R₄=Alkyl;
R₅=O-Alkyl;
when A=C, R₁₀=R₁₁=H; or when A=N, R₁₀=Alkyl and R₁₁=null; and
Alkyl=aliphatic C₁-C₄ alkyl.

In other embodiments, the present disclosure provides a compound of formula (IX):

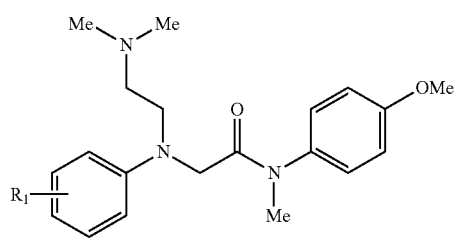

(IX)

wherein:
R₁=H, m-chloro; 3,4-dichloro; o-methoxy; p-methoxy; o-methyl; m-trifluoromethoxy; m-trifluoromethyl, p-chloro; 2,5-dichloro; 3-chloro-4-fluoro; 2-fluoro-3-chloro; or o-trifluoromethyl.

In other embodiments, the present disclosure provides a compound of formula (X):

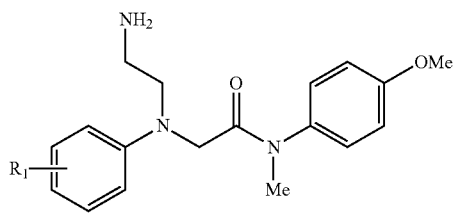

(X)

wherein:
R₁=H, m-chloro; 3,4-dichloro; o-methoxy; p-methoxy; o-methyl; m-trifluoromethoxy; m-trifluoromethyl, p-chloro; 2,5-dichloro; 3-chloro-4-fluoro; 2-fluoro-3-chloro; or o-trifluoromethyl.

In other embodiments, the present disclosure provides a compound of formula (XI):

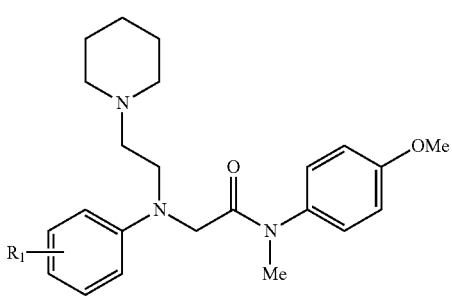

(XI)

wherein:
R₁=H, m-chloro; 3,4-dichloro; o-methoxy; p-methoxy; o-methyl; m-trifluoromethoxy; m-trifluoromethyl, p-chloro; 2,5-dichloro; 3-chloro-4-fluoro; 2-fluoro-3-chloro; or o-trifluoromethyl.

In other embodiments, the present disclosure provides a compound of formula (XII):

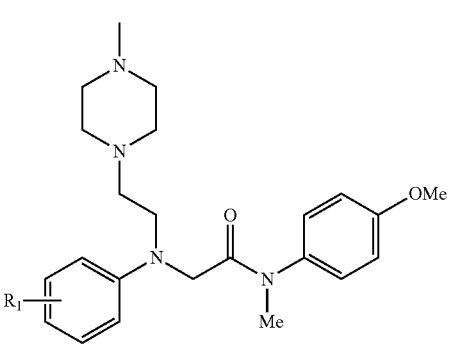

(XII)

wherein:
R₁=H, m-chloro; 3,4-dichloro; o-methoxy; p-methoxy; o-methyl; m-trifluoromethoxy; m-trifluoromethyl, p-chloro; 2,5-dichloro; 3-chloro-4-fluoro; 2-fluoro-3-chloro; or o-trifluoromethyl.

In other embodiments, the present disclosure provides a compound of formula (XIII):

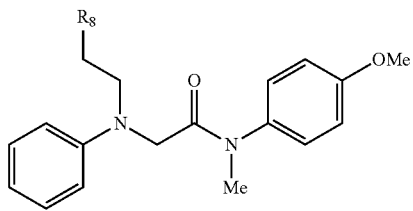

(XIII)

wherein:
$R_8$=$NH_2$, NH(Me), N(Me)$_2$,

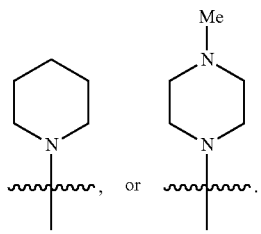 [SMILES: *N1CCCCC1 ; *N1CCN(C)CC1]

In other embodiments, the present disclosure provides a compound of formula (XIV):

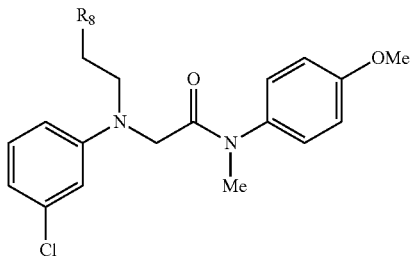

(XIV)

wherein:
$R_8$=$NH_2$, NH(Me), N(Me)$_2$,

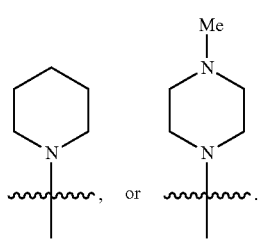 [SMILES: *N1CCCCC1 ; *N1CCN(C)CC1]

In other embodiments, the present disclosure provides a compound of formula (XV):

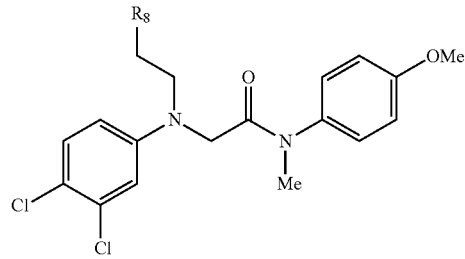

(XV)

wherein:
$R_8$=$NH_2$, NH(Me), N(Me)$_2$,

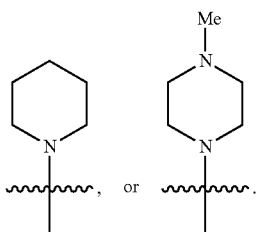 [SMILES: *N1CCCCC1 ; *N1CCN(C)CC1]

In other embodiments, the present disclosure provides a compound of formula (XVI):

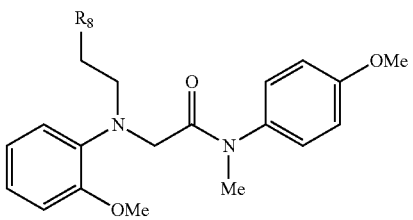

(XVI)

wherein:
$R_8$=$NH_2$, NH(Me), N(Me)$_2$,

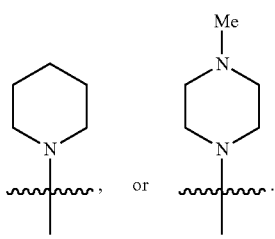

In other embodiments, the present disclosure provides a compound of formula (XVII):

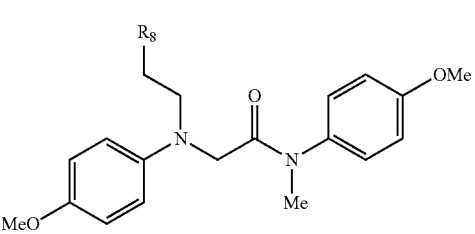

(XVII)

wherein:
$R_8$=NH$_2$, NH(Me), N(Me)$_2$,

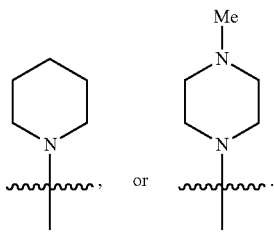 [SMILES: *N1CCCCC1 ; *N1CCN(C)CC1]

In other embodiments, the present disclosure provides a compound of formula (XVIII):

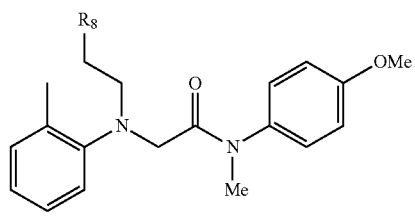

(XVIII)

wherein:
$R_8$=NH$_2$, NH(Me), N(Me)$_2$,

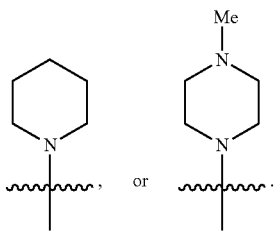 [SMILES: *N1CCCCC1 ; *N1CCN(C)CC1]

In other embodiments, the present disclosure provides a compound of formula (XIX):

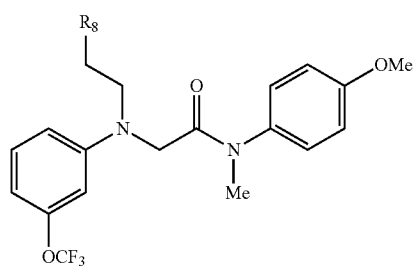

(XIX)

wherein:
$R_8$=NH$_2$, NH(Me), N(Me)$_2$,

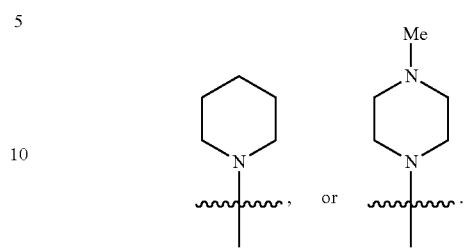

In other embodiments, the present disclosure provides a compound of formula (XX):

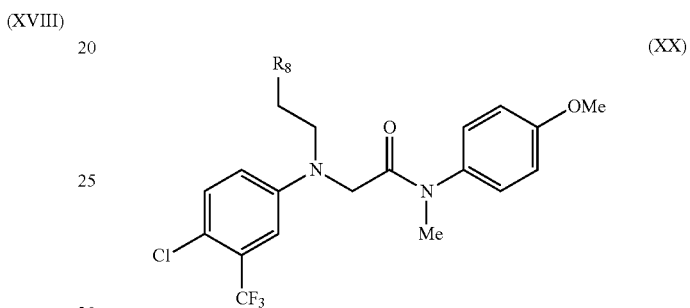

(XX)

wherein:
$R_8$=NH$_2$, NH(Me), N(Me)$_2$,

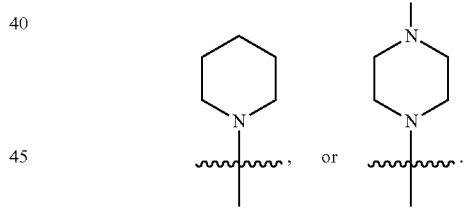

In other embodiments, the present disclosure provides a compound of formula (XXI):

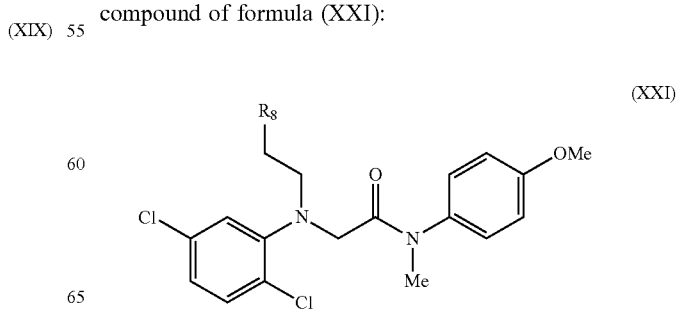

(XXI)

wherein:
R₈=NH₂, NH(Me), N(Me)₂,

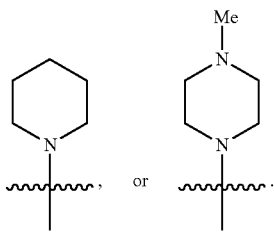 [SMILES: *N1CCCCC1 ; *N1CCN(C)CC1]

In other embodiments, the present disclosure provides a compound of formula (XXII):

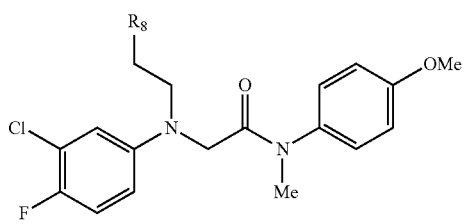

(XXII)

wherein:
R₈=NH₂, NH(Me), N(Me)₂,

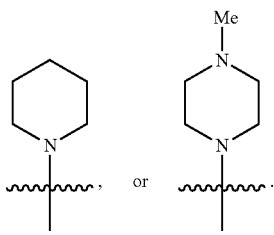 [SMILES: *N1CCCCC1 ; *N1CCN(C)CC1]

In other embodiments, the present disclosure provides a compound of formula (XXIII):

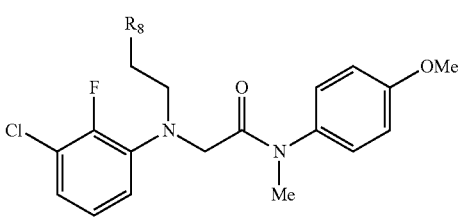

(XXIII)

wherein:
R₈=NH₂, NH(Me), N(Me)₂,

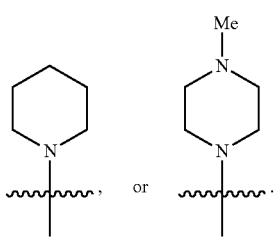 [SMILES: *N1CCCCC1 ; *N1CCN(C)CC1]

In other embodiments, the present disclosure provides a compound of formula (XXIV):

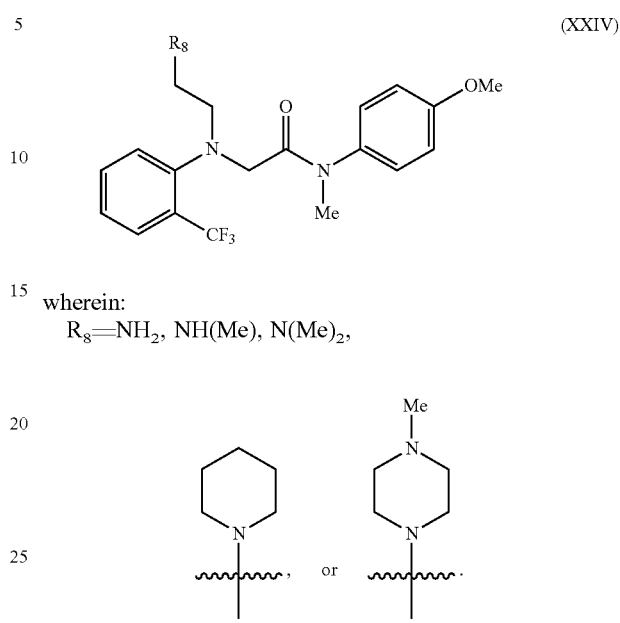

wherein:
R₈=NH₂, NH(Me), N(Me)₂,

In other embodiments, the present disclosure provides a composition comprising a compound of any one of formulas (I) to (XXIV).

In other embodiments, the present disclosure provides a method of treating or preventing pain in a subject, the method comprising topically applying the composition comprising a compound of any one of formulas (I) to (XXIV) to skin of the subject proximal to perceived pain or expected pain.

DETAILED DESCRIPTION

Figure 1:
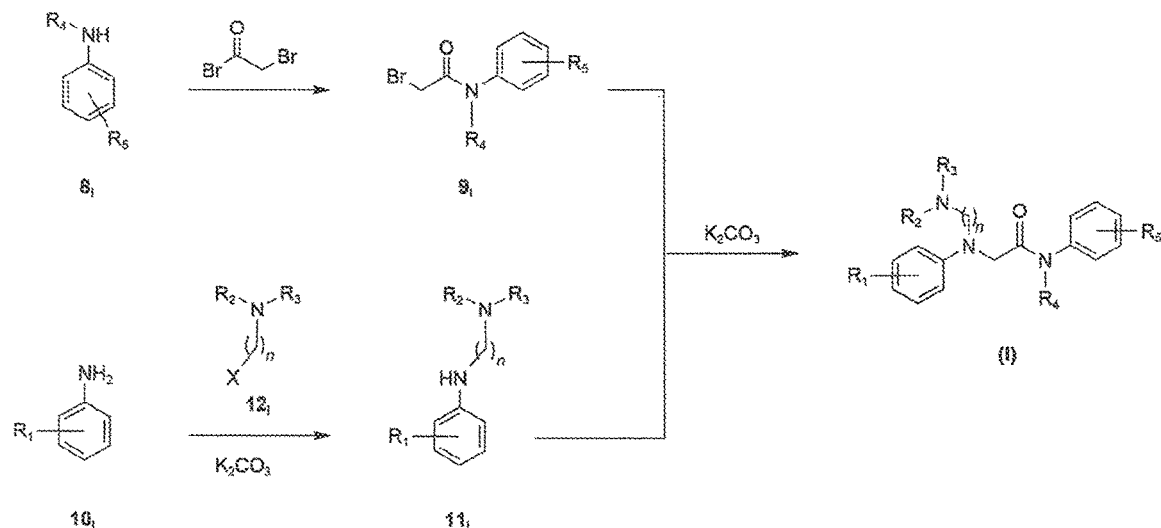
FIG. 1 shows a representative synthetic route for producing compounds of formula (I).

The present disclosure provides compounds useful as anesthetic agents, for example to treat or prevent pain when applied topically to skin of a subject, and methods of making such compounds and using such compounds to treat or prevent pain.

1. Anesthetic Compounds

The present disclosure provides compounds of formula (I):

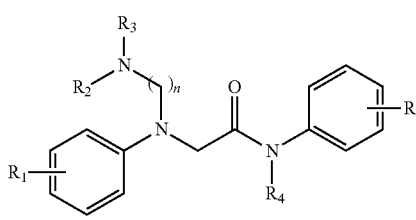

(I)

wherein:
$R_1$ is H, alkyl, alkoxy, or one or more electron withdrawing groups;
$R_2$ and $R_3$ are each independently H or alkyl or, taken together, form a 4- to 8-membered heterocyclic ring with the adjacent nitrogen atom;
$R_4$ is H or alkyl;
$R_5$ is H or one or more electron donating groups; and
n is 1 to 4.

The present disclosure also provides salts of compounds of formula (I), which may be prepared for example by contacting a neutral compound of formula (I) with an acid (e.g., hydrochloric acid) to form a salt (e.g., a hydrochloride salt) of the compound of formula (I). A suitable salt of a compound of formula (I) is a salt of a mineral or organic acid. Suitable mineral acids include hydrochloric, hydrobromic, hydroiodic, nitric or sulfuric acid. A suitable organic acid is, for example, an organic achiral acid such as acetic, trifluoroacetic, oxalic or p-toluenesulfonic acid, or an organic chiral acid such as L-tartaric acid, dibenzoyl-L-tartaric acid or di-p-toluoyl-L-tartaric acid.

The present disclosure also provides hydrates of compounds of formula (I).

In some embodiments, $R_1$ is selected from the group consisting of: H, alkyl, alkoxy, and electron withdrawing groups. In some embodiments, only one $R_1$ group is present and may be at the ortho-, meta-, or para-position of the aryl ring. In other embodiments, two to five $R_1$ groups are present, and each $R_1$ group is independently selected from the group consisting of H, alkyl, alkoxy, and electron withdrawing groups, and each $R_1$ group located at any combination of the ortho-, meta-, and para-positions of the aryl ring. For example and without limitation, two $R_1$ groups may be present in a compound of formula (I) consistent with the present disclosure, and each $R_1$ group is independently selected from the group consisting of H, alkyl, alkoxy, and electron withdrawing groups. In other embodiments, three $R_1$ groups are present, and each $R_1$ group is independently selected from the group consisting of H, alkyl, alkoxy, and electron withdrawing groups. In still other embodiments, four $R_1$ groups are present. In other embodiments, five $R_1$ groups are present, and each $R_1$ group is independently selected from the group consisting of H, alkyl, alkoxy, and electron withdrawing groups.

When $R_1$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When $R_1$ is alkoxy, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

When $R_1$ is an electron withdrawing group, the electron withdrawing group may be a halogen, a halogenated alkyl group, or a halogenated alkoxy group. For example and without limitation, the electron withdrawing group may be a halgoen, a halogen-substituted alkyl, a halogen-substituted alkoxyl, a perhaloalkyl, or a perhaloalkoxyl. fluoro, In some embodiments, each electron withdrawing group is independently selected from chloro, bromide, iodide, halomethyl, dihalomethyl, trihalomethyl, halomethoxyl, dihalomethoxyl, and trihalomethoxyl. In some embodiments, each electron withdrawing group is independently selected from the group consisting of fluoro, chloro, trifluoromethyl, and trifluoromethoxyl.

Each $R_2$ and $R_3$ are each independently H or alkyl or, taken together, form a 4- to 8-membered heterocyclic ring with the adjacent nitrogen atom. In some embodiments, $R_2$ is H while $R_3$ is alkyl. In some embodiments, both $R_2$ and $R_3$ are alkyl. When $R_2$ and/or $R_3$ are alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

In some embodiments, $R_2$ and $R_3$ are covalently connected to form, with the adjacent nitrogen atom, a heterocyclic ring. The heterocyclic ring may include one to three nitrogen atoms and a total of four to eight atoms in the ring. The heterocyclic ring may be unsubstituted or substituted, for example with an alkyl or alkoxyl group. For example and without limitation, $R_2$ and $R_3$ may be covalently connected and include a total of five carbon atoms to form a piperidinyl ring including the nitrogen atom adjacent to $R_2$ and $R_3$. In other embodiments, $R_2$ and $R_3$ may, together, have a general formula
—$(CH_2)_pN(R_7)(CH_2)_q$—, wherein p is 1 to 4, q is 1 to 4, p and q combined total 3 to 8, and $R_7$ is H or alkyl. When $R_7$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

$R_4$ is H or alkyl. When $R_4$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

$R_5$ is H or one or more electron donating groups. When $R_5$ is one or more electron donating groups, $R_5$ may be a single electron donating group in the ortho-, meta-, or para-position of the aryl ring. In other embodiments, $R_5$ may be two to five electron donating groups in any combination of ortho-, meta-, and para-positions of the aryl ring. Each electron donating group may be independently selected from alkyl and alkoxyl. When $R_5$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When $R_5$ is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

The number of methylene groups (n) in compounds of formula (I) may be 1 to 4. In some embodiments, n is 1. In other embodiments, n is 2. In other embodiments, n is 3. In other embodiments, n is 4.

Some example compounds of formula (I) are provided in Table 1 below.

TABLE 1

Example Compounds of Formula (I)

| Compound | $R_1$ | $R_2$ | $R_3$ | $R_4$ | $R_5$ | $R_7$ | n | p | q |
|---|---|---|---|---|---|---|---|---|---|
| 2290 | H | Me | Me | Me | p-OMe | n/a | 2 | n/a | n/a |
| 2291 | m-Cl | Me | Me | Me | p-OMe | n/a | 2 | n/a | n/a |
| 2292 | m-Cl p-Cl | Me | Me | Me | p-OMe | n/a | 2 | n/a | n/a |
| 2293 | o-OMe | Me | Me | Me | p-OMe | n/a | 2 | n/a | n/a |
| 2294 | p-OMe | Me | Me | Me | p-OMe | n/a | 2 | n/a | n/a |
| 2295 | o-Me | Me | Me | Me | p-OMe | n/a | 2 | n/a | n/a |
| 2296 | m-OCF$_3$ | Me | Me | Me | p-OMe | n/a | 2 | n/a | n/a |
| 2297 | m-CF$_3$ p-Cl | Me | Me | Me | p-OMe | n/a | 2 | n/a | n/a |
| 2298 | 2-Cl 5-Cl | Me | Me | Me | p-OMe | n/a | 2 | n/a | n/a |
| 2299 | m-Cl p-F | Me | Me | Me | p-OMe | n/a | 2 | n/a | n/a |
| 2300 | 2-F 3-Cl | Me | Me | Me | p-OMe | n/a | 2 | n/a | n/a |
| 2301 | o-CF$_3$ | Me | Me | Me | p-OMe | n/a | 2 | n/a | n/a |
| 2302 | H | H | H | Me | p-OMe | n/a | 2 | n/a | n/a |
| 2303 | H | —(CH$_2$)$_5$— | | Me | p-OMe | n/a | 2 | n/a | n/a |
| 2304 | H | —(CH$_2$)$_p$N(R$_7$)(CH$_2$)$_q$— | | Me | p-OMe | Me | 2 | 2 | 2 |

Referring now to FIG. 1, compounds consistent with formula (I) can be synthesized by, for example, acylating anilines 8, with bromoacetyl bromide to form α-bromoamido intermediates 9$_I$. Intermediates 11$_I$ can be formed by alkylating anilines 10$_I$ with β-haloamines 12$_I$ in the presence of base. Combining intermediates 11$_I$ with the α-bromoamido intermediates 9$_I$ in the presence of base yields compounds of formula (I).

The present disclosure also provides compounds of formula (II):

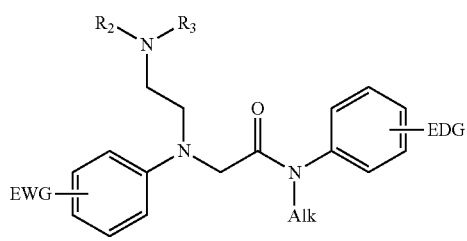

(II)

wherein:
- EWG is one or more electron withdrawing groups selected from the group consisting of: Cl, F, halogenated alkyl, and halogenated alkoxyl;
- $R_2$ and $R_3$ are each independently H or alkyl;
- Alk is an aliphatic carbon group consisting of 1 to 6 carbon atoms; and
- EDG is one or more alkoxy or alkyl electron donating groups.

In compounds of formula (II), EWG is one or more electron withdrawing groups each independently selected from the group consisting of: Cl, F, halogenated alkyl, and halogenated alkoxyl. For example and without limitation, EWG may in some embodiments be a single electron withdrawing group located at the ortho-, meta-, or para-position of the aryl ring. In other embodiments, EWG is two or more electron withdrawing groups located at any combination of the ortho-positions, the meta-positions, and the para-position of the aryl ring.

Each EWG may independently be selected from the group consisting of chloro, fluoro, halogenated alkyl, and halogenated alkoxyl. The halogenated alkyl may be monohaloalkyl, dihaloalkyl, trihaloalkyl, or perhaloalkyl and may have 1 to 6 carbon atoms (i.e., $C_{1-6}$ haloalkyl). The haloalkyl electron withdrawing group may be saturated or unsaturated. The halogenated alkyl may be branched, linear, or cyclic. In some embodiments, the electron withdrawing group is trifluoromethyl. The halogenated alkoxyl may be monohaloalkoxyl, dihaloalkoxyl, trihaloalkoxyl, or perhaloalkoxyl and may have 1 to 6 carbon atoms (i.e., $C_{1-6}$ haloalkoxyl). The haloalkoxyl electron withdrawing group may be saturated or unsaturated. The halogenated alkoxyl may be branched, linear, or cyclic. In some embodiments, the electron withdrawing group is trifluoromethoxyl.

Each $R_2$ and $R_3$ is independently H or alkyl. When $R_2$ and/or $R_3$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

EDG is one or more alkoxy or alkyl electron donating groups. EDG may be a single electron donating group in the ortho-, meta-, or para-position of the aryl ring. In other embodiments, EDG may be two to five electron donating groups in any combination of ortho-, meta-, and para-positions of the aryl ring. Each EDG may be independently selected from alkyl and alkoxyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (II) are provided in Table 2 below.

TABLE 2

Example Compounds of Formula (II)

| Compound | EWG | $R_2$ | $R_3$ | Alk | EDG | $R_7$ | n | p | q |
|---|---|---|---|---|---|---|---|---|---|
| 2290 | H | Me | Me | Me | p-OMe | n/a | 2 | n/a | n/a |
| 2291 | m-Cl | Me | Me | Me | p-OMe | n/a | 2 | n/a | n/a |
| 2292 | m-Cl p-Cl | Me | Me | Me | p-OMe | n/a | 2 | n/a | n/a |
| 2293 | o-OMe | Me | Me | Me | p-OMe | n/a | 2 | n/a | n/a |
| 2294 | p-OMe | Me | Me | Me | p-OMe | n/a | 2 | n/a | n/a |
| 2295 | o-Me | Me | Me | Me | p-OMe | n/a | 2 | n/a | n/a |
| 2296 | m-OCF$_3$ | Me | Me | Me | p-OMe | n/a | 2 | n/a | n/a |
| 2297 | m-CF$_3$ p-Cl | Me | Me | Me | p-OMe | n/a | 2 | n/a | n/a |
| 2298 | 2-Cl 5-Cl | Me | Me | Me | p-OMe | n/a | 2 | n/a | n/a |
| 2299 | m-Cl p-F | Me | Me | Me | p-OMe | n/a | 2 | n/a | n/a |
| 2300 | 2-F 3-Cl | Me | Me | Me | p-OMe | n/a | 2 | n/a | n/a |
| 2301 | o-CF$_3$ | Me | Me | Me | p-OMe | n/a | 2 | n/a | n/a |
| 2302 | H | H | H | Me | p-OMe | n/a | 2 | n/a | n/a |
| 2303 | H | —(CH$_2$)$_5$— | | Me | p-OMe | n/a | 2 | n/a | n/a |
| 2304 | H | —(CH$_2$)$_p$N(R$_7$)(CH$_2$)$_q$— | | Me | p-OMe | Me | 2 | 2 | 2 |

Figure 2:
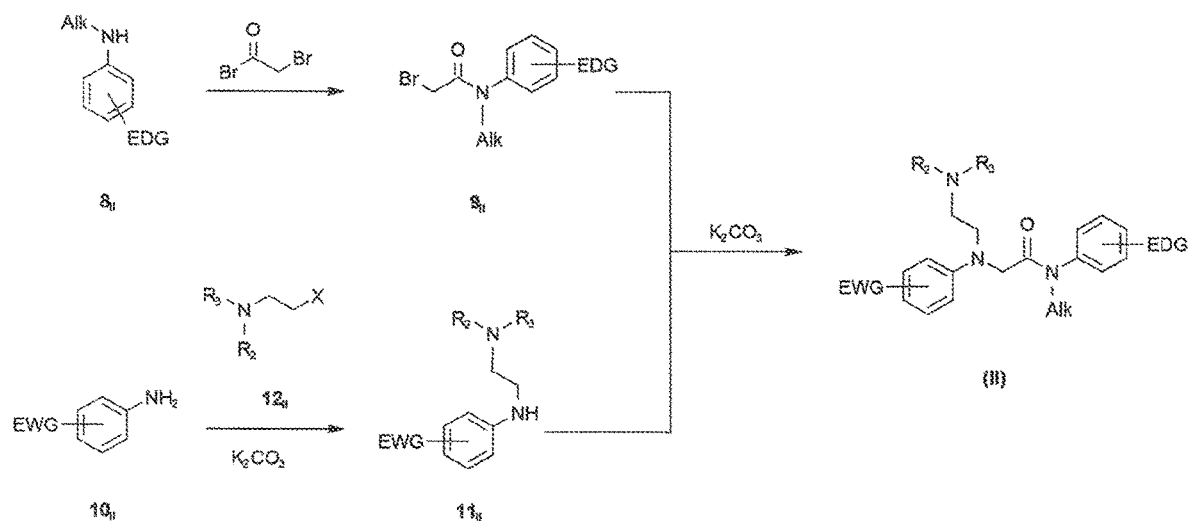
FIG. 2 shows a representative synthetic route for producing compounds of formula (II).

Referring now to FIG. 2, compounds consistent with formula (II) can be synthesized by, for example, acylating alkylanilines $8_{II}$ with bromoacetyl bromide to form α-bromoamido intermediates $9_{II}$. Intermediates $11_{II}$ can be formed by alkylating anilines $10_{II}$ with β-haloamines $12_{III}$ the presence of base. Combining intermediates $11_{II}$ with the α-bromoamido intermediates $9_{III}$ the presence of base yields compounds of formula (II).

The present disclosure also provides compounds of formula (III):

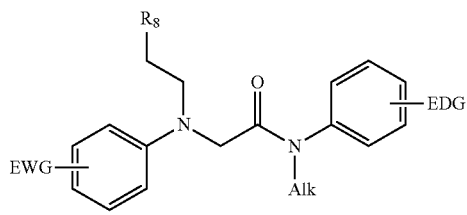

(III)

wherein:
EWG is one or more electron withdrawing groups selected from the group consisting of: Cl, F, CF$_3$, and OCF$_3$;
R$_8$ is selected from the group consisting of:
—NH$_2$, —N(H)Alk, —N(Alk)$_2$,

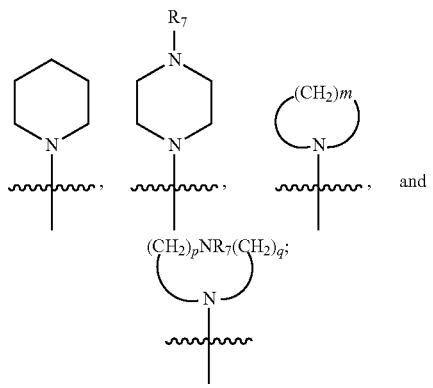

R$_7$ is H or alkyl;
m is 3 to 6;
p is 1 to 4;
q is 1 to 4;
p+q is 3 to 6;
each Alk is independently an aliphatic carbon group consisting of 1 to 6 carbon atoms; and
EDG is one or more alkoxy or alkyl electron donating groups.

In compounds of formula (III), EWG is one or more electron withdrawing groups each independently selected from the group consisting of: chloro, fluoro, trifluoromethyl, and trifluoromethoxy. For example and without limitation, EWG may in some embodiments be a single electron withdrawing group that is chloro, fluoro, trifluoromethyl, or trifluoromethoxy that is located at the ortho-, meta-, or para-position of the aryl ring. In other embodiments, EWG is two or more electron withdrawing groups independently selected from chloro, fluoro, trifluoromethyl, and trifluoromethoxy located at any combination of the ortho-positions, the meta-positions, and the para-position of the aryl ring.

R$_8$ is an n-amino substituent selected from —NH$_2$, —N(H)Alk, —N(Alk)$_2$,

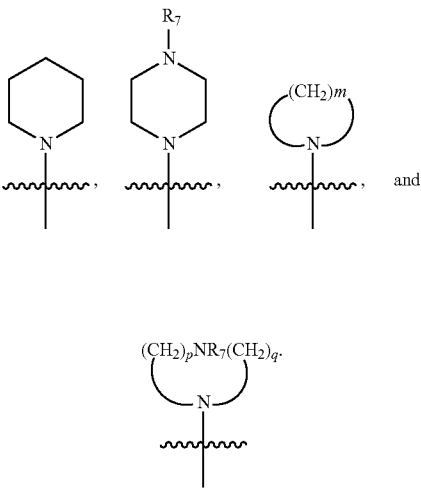

When R$_8$ is —N(H)Alk or —N(Alk)$_2$, Alk is an aliphatic carbon group consisting of 1 to 6 carbon atoms (i.e., C$_{1-6}$ alkyl). Alk may be linear, branched, or cyclic. When Alk is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds.

When R$_8$ is

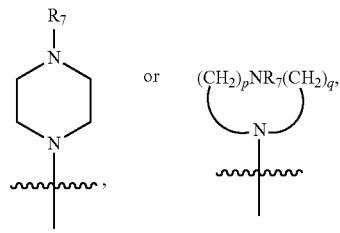

R$_7$ is H or alkyl. When R$_7$ is alkyl, the alkyl group can be an aliphatic carbon group consisting of 1 to 6 carbon atoms (i.e., C$_{1-6}$ alkyl). The alkyl group may be linear, branched, or cyclic. When the alkyl group is cyclic, the alkyl group may consist of three to six carbon atoms (i.e., C$_{3-6}$ cycloalkyl). The alkyl group may be saturated or unsaturated with one or more carbon-carbon double bonds and/or carbon-carbon triple bonds. In some embodiments, R$_7$ is H. In other embodiments, R$_7$ is methyl. In other embodiments, R$_7$ is ethyl. In other embodiments, R$_7$ is propyl (e.g., n-propyl or isopropyl). In other embodiments, R$_7$ is butyl (e.g., 1-butyl, 2-butyl, or t-butyl). In other embodiments, R$_7$ is pentyl (e.g., 1-n-pentyl, 2-n-pentyl, 3-n-pentyl, 2-methylbut-4-yl, 2-methylbuty-3-yl, or 1-dimethylprop-1-yl). In other embodiments, R$_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When R8 is

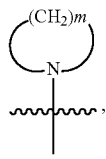

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When R8 is

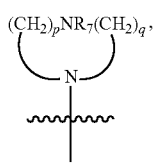

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

EDG is one or more alkoxy or alkyl electron donating groups. EDG may be a single electron donating group in the ortho-, meta-, or para-position of the aryl ring. In other embodiments, EDG may be two to five electron donating groups in any combination of ortho-, meta-, and para-positions of the aryl ring. Each EDG may be independently selected from alkyl and alkoxyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (III) are provided in Table 3 below.

TABLE 3

Example Compounds of Formula (III)

| Compound | EWG | R8 | Alk | EDG | R7 | m | n | p | q |
|---|---|---|---|---|---|---|---|---|---|
| 2290 | H | —N(Alk)2 | Me | p-OMe | n/a | n/a | 2 | n/a | n/a |
| 2291 | m-Cl | —N(Alk)2 | Me | p-OMe | n/a | n/a | 2 | n/a | n/a |
| 2292 | m-Cl p-Cl | —N(Alk)2 | Me | p-OMe | n/a | n/a | 2 | n/a | n/a |
| 2293 | o-OMe | —N(Alk)2 | Me | p-OMe | n/a | n/a | 2 | n/a | n/a |
| 2294 | p-OMe | —N(Alk)2 | Me | p-OMe | n/a | n/a | 2 | n/a | n/a |

TABLE 3-continued

Example Compounds of Formula (III)

| Compound | EWG | R8 | Alk | EDG | R7 | m | n | p | q |
|---|---|---|---|---|---|---|---|---|---|
| 2295 | o-Me | —N(Alk)2 | Me | p-OMe | n/a | n/a | 2 | n/a | n/a |
| 2296 | m-OCF3 | —N(Alk)2 | Me | p-OMe | n/a | n/a | 2 | n/a | n/a |
| 2297 | m-CF3 p-Cl | —N(Alk)2 | Me | p-OMe | n/a | n/a | 2 | n/a | n/a |
| 2298 | 2-Cl 5-Cl | —N(Alk)2 | Me | p-OMe | n/a | n/a | 2 | n/a | n/a |
| 2299 | m-Cl p-F | —N(Alk)2 | Me | p-OMe | n/a | n/a | 2 | n/a | n/a |
| 2300 | 2-F 3-Cl | —N(Alk)2 | Me | p-OMe | n/a | n/a | 2 | n/a | n/a |
| 2301 | o-CF3 | —N(Alk)2 | Me | p-OMe | n/a | n/a | 2 | n/a | n/a |
| 2302 | H | —NH2 | Me | p-OMe | n/a | n/a | 2 | n/a | n/a |
| 2303 | H | 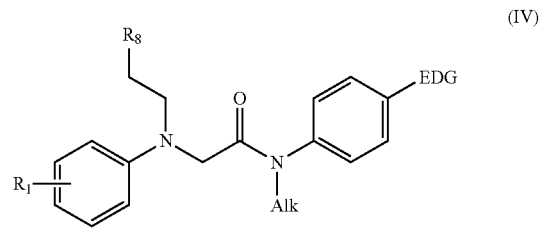 | Me | p-OMe | n/a | 5 | 2 | n/a | n/a |
| 2304 | H | 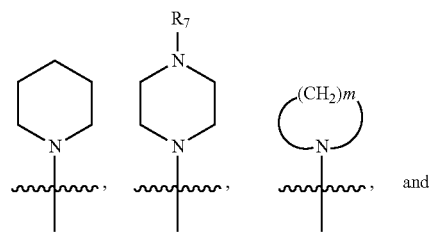 | Me | p-OMe | Me | n/a | 2 | 2 | 2 |

Figure 3:
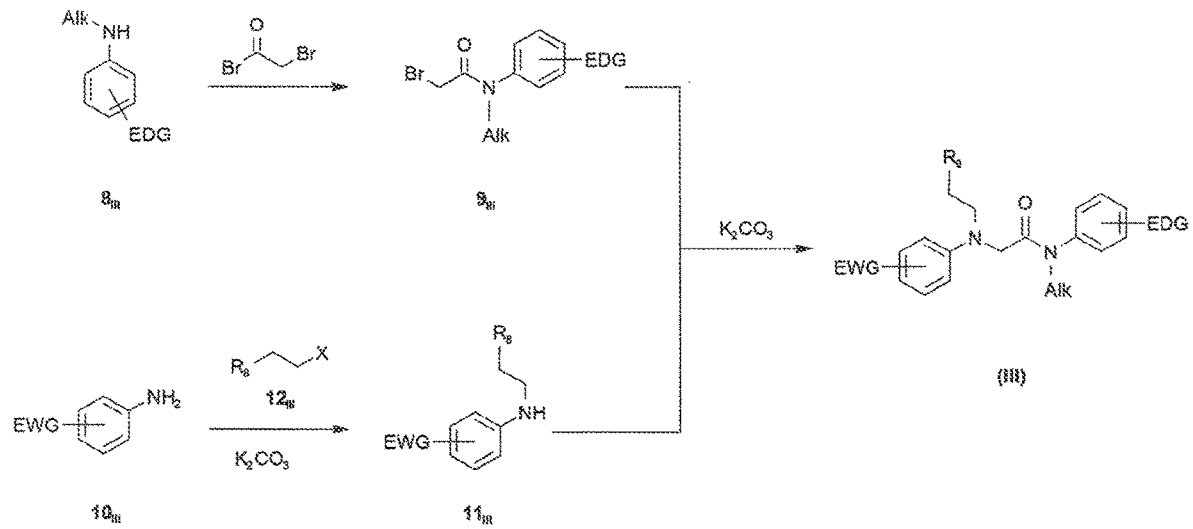
FIG. 3 shows a representative synthetic route for producing compounds of formula (III).

Referring now to FIG. 3, compounds consistent with formula (III) can be synthesized by, for example, acylating alkylanilines $8_{II}$ with bromoacetyl bromide to form α-bromoamido intermediates $9_{III}$. Intermediates $11_{III}$ can be formed by alkylating anilines $10_{III}$ with β-haloamines $12_{III}$ the presence of base. Combining intermediates $11_{III}$ with the α-bromoamido intermediates $9_{III}$ the presence of base yields compounds of formula (III).

The present disclosure further provides compounds of formula (IV):

(IV)

wherein:
R1 is H, Cl, F, —CF3, —OCF3, or —OMe;
R8 is selected from the group consisting of:
—NH2, —N(H)Alk, —N(Alk)2, and -continued

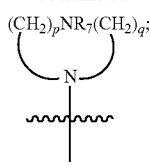

$R_7$ is H or alkyl;

m is 3 to 6;

p is 1 to 4;

q is 1 to 4;

p+q is 3 to 6;

each Alk is independently an aliphatic carbon group consisting of 1 to 6 carbon atoms; and EDG is one or more amino, aryl, acylamido, acyloxy, alkoxy or alkyl electron donating groups.

In compounds of formula (IV), $R_1$ is H or one or more substituents each independently selected from the group consisting of: chloro, fluoro, trifluoromethyl, trifluoromethoxy, and methoxy. For example and without limitation, $R_1$ may in some embodiments be a single substituent that is chloro, fluoro, trifluoromethyl, trifluoromethoxy, or methoxy that is located at the ortho-, meta-, or para-position of the aryl ring. In other embodiments, $R_1$ is two or more substituents each independently selected from chloro, fluoro, trifluoromethyl, trifluoromethoxy, and methoxy located at any combination of the ortho-positions, the meta-positions, and the para-position of the aryl ring.

$R_8$ is an n-amino substituent selected from —$NH_2$, —N(H)Alk, —N(Alk)$_2$,

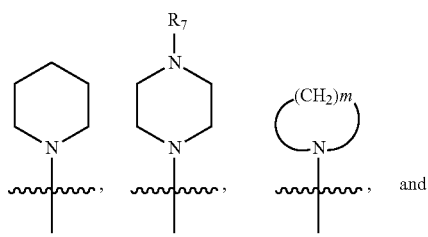

and

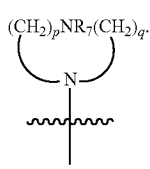

When $R_8$ is —N(H)Alk or —N(Alk)$_2$, Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When $R_8$ is

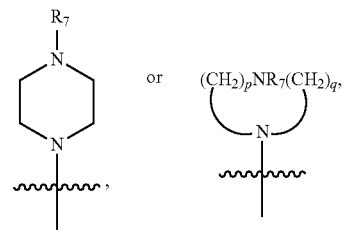

$R_7$ is H or alkyl. When $R_7$ is alkyl, the alkyl group can be an aliphatic carbon group consisting of 1 to 6 carbon atoms (i.e., $C_{1-6}$ alkyl). The alkyl group may be linear, branched, or cyclic. When the alkyl group is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, $R_7$ is H. In other embodiments, $R_7$ is methyl. In other embodiments, $R_7$ is ethyl. In other embodiments, $R_7$ is propyl (e.g., n-propyl or isopropyl). In other embodiments, $R_7$ is butyl (e.g., 1-butyl, 2-butyl, or t-butyl). In other embodiments, $R_7$ is pentyl (e.g., 1-n-pentyl, 2-n-pentyl, 3-n-pentyl, 2-methylbut-4-yl, 2-methylbuty-3-yl, or 1-dimethylprop-1-yl). In other embodiments, $R_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When $R_8$ is

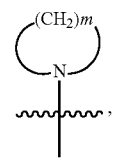

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

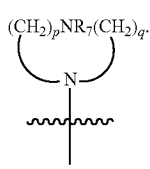

When $R_8$ is, p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

EDG is one or more amino, aryl, acylamido, acyloxy, alkoxy or alkyl electron donating groups. EDG may be a single electron donating substituent in the ortho-, meta-, or para-position of the aryl ring. In some embodiments, the single EDG substituent is at the ortho-position of the aryl ring. In other embodiments, the single EDG substituent is at the para-position of the aryl ring. In other embodiments, EDG may be two to five electron donating groups in any combination of ortho-, meta-, and para-positions of the aryl ring. In some embodiments, two EDG substituents are at the two ortho-positions of the aryl ring. In other embodiments, one EDG substituent is at the ortho-position and a second same or different EDG substituent is at the para-position of the aryl ring. In other embodiments, one EDG substituent is at one ortho-position of the aryl ring and a second same or different EDG substituent is at the other ortho-position of the aryl ring. In some embodiments, one EDG substituent is at one ortho-position of the aryl ring, a second same or different EDG substituent is at the other ortho-position of the aryl ring, and a third same or different EDG substituent is at the para-position of the aryl ring.

Each EDG may be independently selected from amino, aryl, acylamido, acyloxy, alkoxy or alkyl. When EDG is amino, the amino group may be —$NH_2$, —N(H)Alk, or —$N(Alk)_2$, with each Alk being an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is aryl, the aryl substituent may be substituted or unsubstituted. The aryl substituent may be heteroatomic, such as a pyridine ring, a pyrazine ring, or a triazine ring that is substituted or unsubstituted. When EDG is acylamido, the acylamido group has a general formula of —N(H)$COR_9$, with $R_9$ being substituted or unsubstituted alkyl. When EDG is acyloxy, the acyloxy group has a general formula of —OC(O)$R_9$, with $R_9$ being substituted or unsubstituted alkyl. When EDG is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When EDG is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds. In some embodiments, EDG is para-alkoxy, such as para-methoxy, para-ethoxy, or para-propoxy.

Some example compounds of formula (IV) are provided in Table 4 below.

TABLE 4

Example Compounds of Formula (IV)

| Compound | $R_1$ | $R_8$ | Alk | EDG | $R_7$ | m | n | p | q |
|---|---|---|---|---|---|---|---|---|---|
| 2290 | H | —$N(Alk)_2$ | Me | p-OMe | n/a | n/a | 2 | n/a | n/a |
| 2291 | m-Cl | —$N(Alk)_2$ | Me | p-OMe | n/a | n/a | 2 | n/a | n/a |
| 2292 | m-Cl p-Cl | —$N(Alk)_2$ | Me | p-OMe | n/a | n/a | 2 | n/a | n/a |
| 2293 | o-OMe | —$N(Alk)_2$ | Me | p-OMe | n/a | n/a | 2 | n/a | n/a |
| 2294 | p-OMe | —$N(Alk)_2$ | Me | p-OMe | n/a | n/a | 2 | n/a | n/a |
| 2295 | o-Me | —$N(Alk)_2$ | Me | p-OMe | n/a | n/a | 2 | n/a | n/a |
| 2296 | m-$OCF_3$ | —$N(Alk)_2$ | Me | p-OMe | n/a | n/a | 2 | n/a | n/a |
| 2297 | m-$CF_3$ p-Cl | —$N(Alk)_2$ | Me | p-OMe | n/a | n/a | 2 | n/a | n/a |

TABLE 4-continued

Example Compounds of Formula (IV)

| Compound | $R_1$ | $R_8$ | Alk | EDG | $R_7$ | m | n | p | q |
|---|---|---|---|---|---|---|---|---|---|
| 2298 | 3-Cl 5-Cl | —$N(Alk)_2$ | Me | p-OMe | n/a | n/a | 2 | n/a | n/a |
| 2299 | m-Cl p-F | —$N(Alk)_2$ | Me | p-OMe | n/a | n/a | 2 | n/a | n/a |
| 2300 | 3-F 3-Cl | —$N(Alk)_2$ | Me | p-OMe | n/a | n/a | 2 | n/a | n/a |
| 2301 | o-$CF_3$ | —$N(Alk)_2$ | Me | p-OMe | n/a | n/a | 2 | n/a | n/a |
| 2302 | H | —$NH_2$ | Me | p-OMe | n/a | n/a | 2 | n/a | n/a |
| 2303 | H | ![ring with (CH2)m] | Me | p-OMe | n/a | 5 | 2 | n/a | n/a |
| 2304 | H | ![ring with (CH2)pNR7(CH2)q] | Me | p-OMe | Me | n/a | 2 | 2 | 2 |

Figure 4:
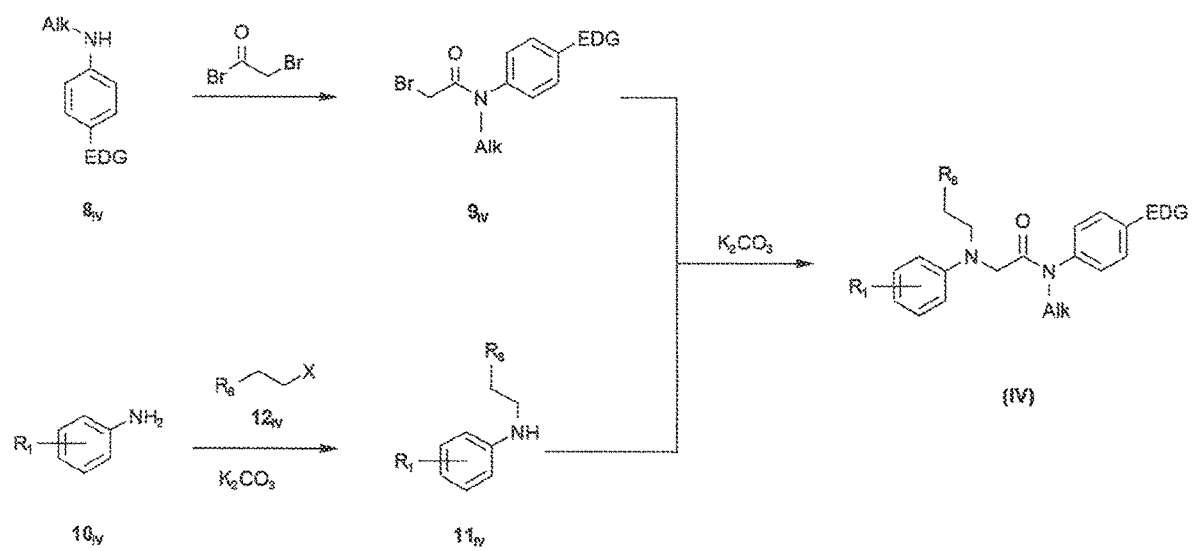
FIG. 4 shows a representative synthetic route for producing compounds of formula (IV).

Referring now to FIG. 4, compounds consistent with formula (IV) can be synthesized by, for example, acylating alkylanilines $8_{IV}$ with bromoacetyl bromide to form α-bromoamido intermediates $9_{IV}$. Intermediates $11_{IV}$ can be formed by alkylating anilines $10_{IV}$ with β-haloamines $12_{IV}$ in the presence of base. Combining intermediates $11_{IV}$ with the α-bromoamido intermediates $9_{IV}$ in the presence of base yields compounds of formula (IV).

The present disclosure provides compounds of formula (V):

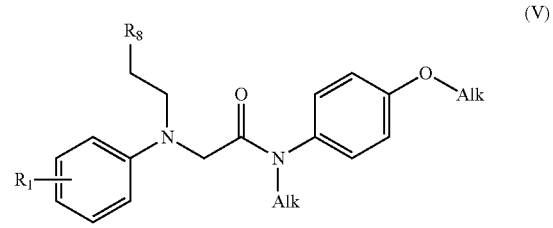

(V)

wherein:

$R_1$ is H, Cl, F, —$CF_3$, —$OCF_3$, or —OMe;

$R_8$ is selected from the group consisting of:

—$NH_2$, —N(H)Alk, —$N(Alk)_2$,

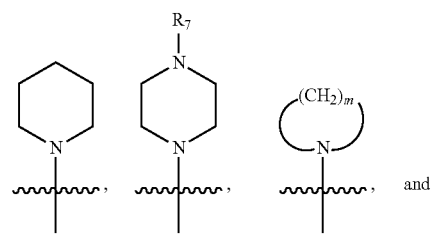

and

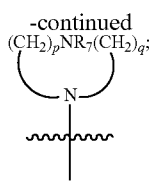

$R_7$ is H or alkyl;
m is 3 to 6;
p is 1 to 4;
q is 1 to 4;
p+q is 3 to 6; and
each Alk is independently an aliphatic carbon group consisting of 1 to 6 carbon atoms.

In compounds of formula (V), $R_1$ is H or one or more substituents each independently selected from the group consisting of: chloro, fluoro, trifluoromethyl, trifluoromethoxy, and methoxy. For example and without limitation, $R_1$ may in some embodiments be a single substituent that is chloro, fluoro, trifluoromethyl, trifluoromethoxy, or methoxy that is located at the ortho-, meta-, or para-position of the aryl ring. In other embodiments, $R_1$ is two or more substituents each independently selected from chloro, fluoro, trifluoromethyl, trifluoromethoxy, and methoxy located at any combination of the ortho-positions, the meta-positions, and the para-position of the aryl ring.

$R_8$ is an n-amino substituent selected from —$NH_2$, —N(H)Alk, —N(Alk)$_2$,

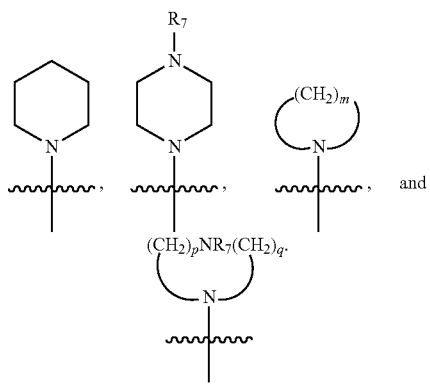

When $R_8$ is —N(H)Alk or —N(Alk)$_2$, Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When $R_8$ is

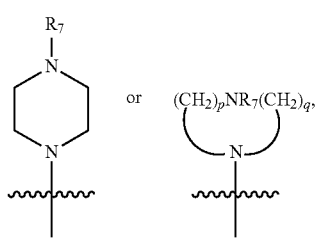

$R_7$ is H or alkyl. When $R_7$ is alkyl, the alkyl group can be an aliphatic carbon group consisting of 1 to 6 carbon atoms (i.e., $C_{1-6}$ alkyl). The alkyl group may be linear, branched, or cyclic. When the alkyl group is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, $R_7$ is H. In other embodiments, $R_7$ is methyl. In other embodiments, $R_7$ is ethyl. In other embodiments, $R_7$ is propyl (e.g., n-propyl or isopropyl). In other embodiments, $R_7$ is butyl (e.g., 1-butyl, 2-butyl, or t-butyl). In other embodiments, $R_7$ is pentyl (e.g., 1-n-pentyl, 2-n-pentyl, 3-n-pentyl, 2-methylbut-4-yl, 2-methylbuty-3-yl, or 1-dimethylprop-1-yl). In other embodiments, $R_7$ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethylbut-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When $R_8$ is

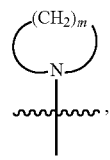

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When $R_8$ is

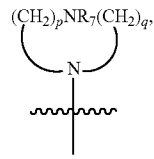

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

Some example compounds of formula (V) are provided in Table 5 below.

TABLE 5

Example Compounds of Formula (V)

| Compound | $R_1$ | $R_8$ | Alk | $R_7$ | m | n | p | q |
|---|---|---|---|---|---|---|---|---|
| 2290 | H | —N(Alk)$_2$ | Me | n/a | n/a | 2 | n/a | n/a |
| 2291 | m-Cl | —N(Alk)$_2$ | Me | n/a | n/a | 2 | n/a | n/a |

TABLE 5-continued

Example Compounds of Formula (V)

| Compound | R₁ | R₈ | Alk | R₇ | m | n | p | q |
|---|---|---|---|---|---|---|---|---|
| 2292 | m-Cl, p-Cl | —N(Alk)₂ | Me | n/a | n/a | 2 | n/a | n/a |
| 2293 | o-OMe | —N(Alk)₂ | Me | n/a | n/a | 2 | n/a | n/a |
| 2294 | p-OMe | —N(Alk)₂ | Me | n/a | n/a | 2 | n/a | n/a |
| 2295 | o-Me | —N(Alk)₂ | Me | n/a | n/a | 2 | n/a | n/a |
| 2296 | m-OCF₃ | —N(Alk)₂ | Me | n/a | n/a | 2 | n/a | n/a |
| 2297 | m-CF₃, p-Cl | —N(Alk)₂ | Me | n/a | n/a | 2 | n/a | n/a |
| 2298 | 3-Cl, 5-Cl | —N(Alk)₂ | Me | n/a | n/a | 2 | n/a | n/a |
| 2299 | m-Cl, p-F | —N(Alk)₂ | Me | n/a | n/a | 2 | n/a | n/a |
| 2300 | 3-F, 3-Cl | —N(Alk)₂ | Me | n/a | n/a | 2 | n/a | n/a |
| 2301 | o-CF₃ | —N(Alk)₂ | Me | n/a | n/a | 2 | n/a | n/a |
| 2302 | H | —NH₂ | Me | n/a | n/a | 2 | n/a | n/a |
| 2303 | H | 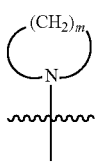 | Me | n/a | 5 | 2 | n/a | n/a |
| 2304 | H | 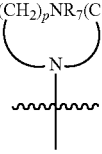 | Me | Me | n/a | 2 | 2 | 2 |

Figure 5:
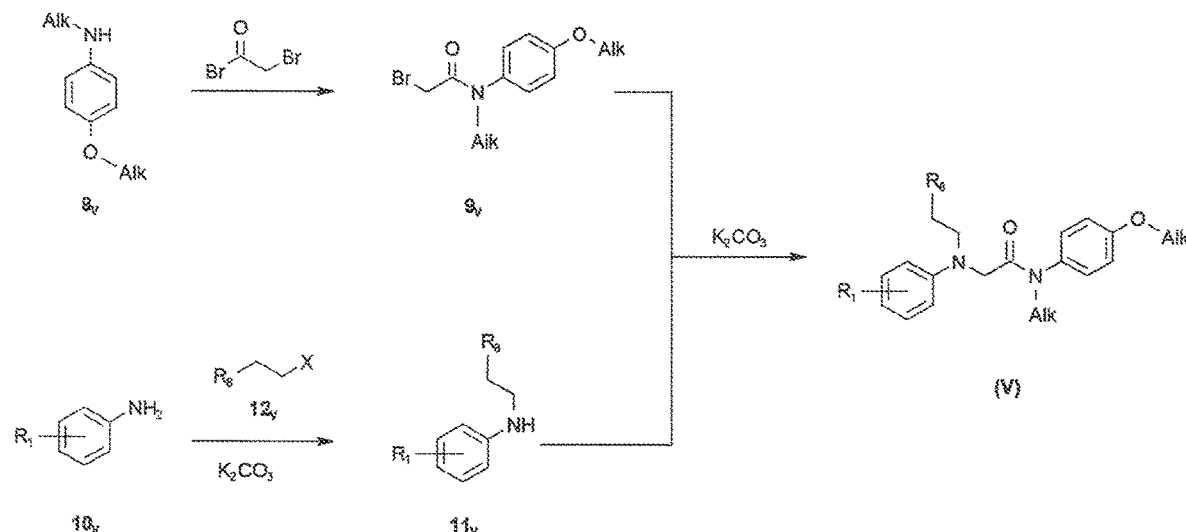
FIG. 5 shows a representative synthetic route for producing compounds of formula (V).

Referring now to FIG. 5, compounds consistent with formula (V) can be synthesized by, for example, acylating alkylaminoalkylphenols $8_V$ with bromoacetyl bromide to form α-bromoamido intermediates $9_V$. Intermediates $11_V$ can be formed by alkylating anilines $10_V$ with β-haloamines $12_V$ in the presence of base. Combining intermediates $11_V$ with α-bromoamido intermediates $9_V$ in the presence of base yields compounds of formula (V).

The present disclosure provides compounds of formula (VI):

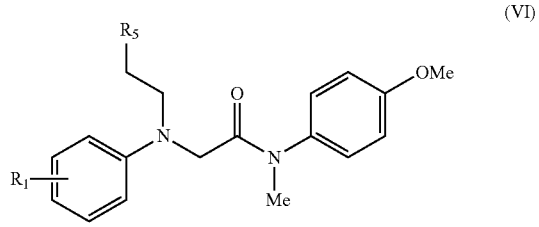

(VI)

wherein:
$R_1$ is H, Cl, F, —CF₃, —OCF₃, —OMe, or methyl;
$R_8$ is selected from the group consisting of:
—NH₂, —N(H)Alk, —N(Alk)₂,

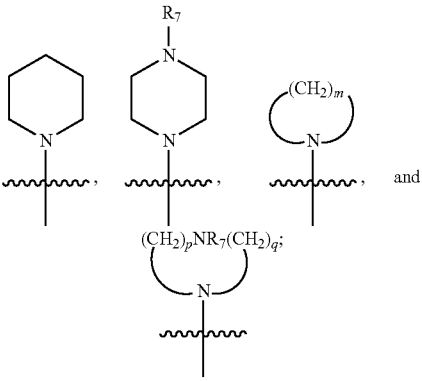

$R_7$ is H or alkyl;
m is 3 to 6;
p is 1 to 4;
q is 1 to 4;
p+q is 3 to 6; and
each Alk is independently an aliphatic carbon group consisting of 1 to 6 carbon atoms.

In compounds of formula (VI), $R_1$ is H or one or more substituents each independently selected from the group consisting of: chloro, fluoro, trifluoromethyl, trifluoromethoxy, methoxy, and methyl. For example and without limitation, $R_1$ may in some embodiments be a single substituent that is chloro, fluoro, trifluoromethyl, trifluoromethoxy, or methoxy that is located at the ortho-, meta-, or para-position of the aryl ring. In other embodiments, $R_1$ is two or more substituents each independently selected from chloro, fluoro, trifluoromethyl, trifluoromethoxy, and methoxy located at any combination of the ortho-positions, the meta-positions, and the para-position of the aryl ring.

$R_8$ is an n-amino substituent selected from —NH₂, —N(H)Alk, —N(Alk)₂,

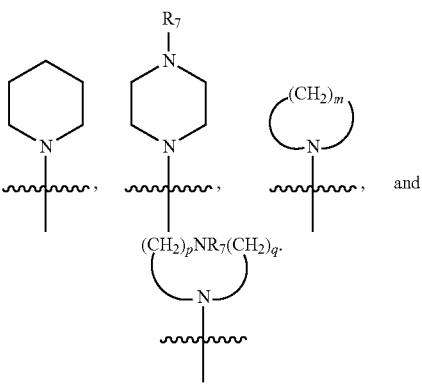

When $R_8$ is —N(H)Alk or —N(Alk)₂, Alk is an aliphatic carbon group consisting of 1 to 6 carbon atoms (i.e., $C_{1-6}$ alkyl). Alk may be linear, branched, or cyclic. When Alk is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

When R₈ is

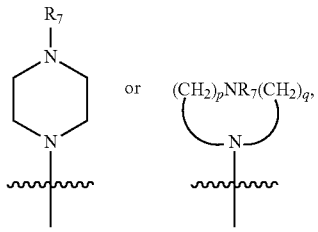

R₇ is H or alkyl. When R₇ is alkyl, the alkyl group can be an aliphatic carbon group consisting of 1 to 6 carbon atoms (i.e., $C_{1-6}$ alkyl). The alkyl group may be linear, branched, or cyclic. When the alkyl group is cyclic, the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, R₇ is H. In other embodiments, R₇ is methyl. In other embodiments, R₇ is ethyl. In other embodiments, R₇ is propyl (e.g., n-propyl or isopropyl). In other embodiments, R₇ is butyl (e.g., 1-butyl, 2-butyl, or t-butyl). In other embodiments, R₇ is pentyl (e.g., 1-n-pentyl, 2-n-pentyl, 3-n-pentyl, 2-methylbut-4-yl, 2-methylbuty-3-yl, or 1-dimethylprop-1-yl). In other embodiments, R₇ is hexyl (e.g., 1-n-hexyl, 2-n-hexyl, 3-n-hexyl, 2-methylpent-5-yl, 2-methylpent-4-yl, 2-methylpent-3-yl, 3-methylpent-5-yl, 2-methylpent-1-yl, 2,3-dimethyl-but-4-yl, 2,2-dimethylbut-4-yl, 3,3-dimethylbut-4-yl, 2,3,3-trimethylprop-3-yl, 1,1-dimethylbut-1-yl, or 1,2,2-trimethylbut-1-yl).

When R₈ is

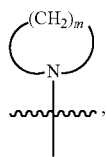

m is 3 to 6. In some embodiments, m is 3, resulting in a 4-membered N-azetidinyl group. In other embodiments, m is 4, resulting in a 5-membered N-pyrrolidinyl group. In other embodiments, m is 5, resulting in a 6-membered N-piperidinyl group. In other embodiments, m is 6, resulting in a 7-membered N-azepanyl group.

When R₈ is

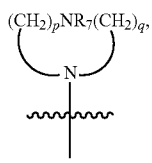

p is 1 to 4, q is 1 to 4, and p and q together total 3 to 6. For example and without limitation, p may be 1 while q is 2, 3, 4 or 5. Alternatively, p may be 2 while q is 1, 2, 3, or 4. In other embodiments, p is 3 while q is 1, 2, or 3.

Some example compounds of formula (VI) are provided in Table 6 below.

TABLE 6

Example Compounds of Formula (VI)

| Compound | R₁ | R₈ | Alk | R₇ | m | n | p | q |
|---|---|---|---|---|---|---|---|---|
| 2290 | H | —N(Alk)₂ | Me | n/a | n/a | 2 | n/a | n/a |
| 2291 | m-Cl | —N(Alk)₂ | Me | n/a | n/a | 2 | n/a | n/a |
| 2292 | m-Cl p-Cl | —N(Alk)₂ | Me | n/a | n/a | 2 | n/a | n/a |
| 2293 | o-OMe | —N(Alk)₂ | Me | n/a | n/a | 2 | n/a | n/a |
| 2294 | p-OMe | —N(Alk)₂ | Me | n/a | n/a | 2 | n/a | n/a |
| 2295 | o-Me | —N(Alk)₂ | Me | n/a | n/a | 2 | n/a | n/a |
| 2296 | m-OCF₃ | —N(Alk)₂ | Me | n/a | n/a | 2 | n/a | n/a |
| 2297 | m-CF₃ p-Cl | —N(Alk)₂ | Me | n/a | n/a | 2 | n/a | n/a |
| 2298 | 2-Cl 5-Cl | —N(Alk)₂ | Me | n/a | n/a | 2 | n/a | n/a |
| 2299 | m-Cl p-F | —N(Alk)₂ | Me | n/a | n/a | 2 | n/a | n/a |
| 2300 | 2-F 3-Cl | —N(Alk)₂ | Me | n/a | n/a | 2 | n/a | n/a |
| 2301 | o-CF₃ | —N(Alk)₂ | Me | n/a | n/a | 2 | n/a | n/a |
| 2302 | H | —NH₂ | n/a | n/a | n/a | 2 | n/a | n/a |
| 2303 | H | (CH₂)ₘ-N- ring | Me | n/a | 5 | 2 | n/a | n/a |
| 2304 | H | (CH₂)ₚNR₇(CH₂)_q-N- ring | Me | Me | n/a | 2 | 2 | 2 |

Figure 6:
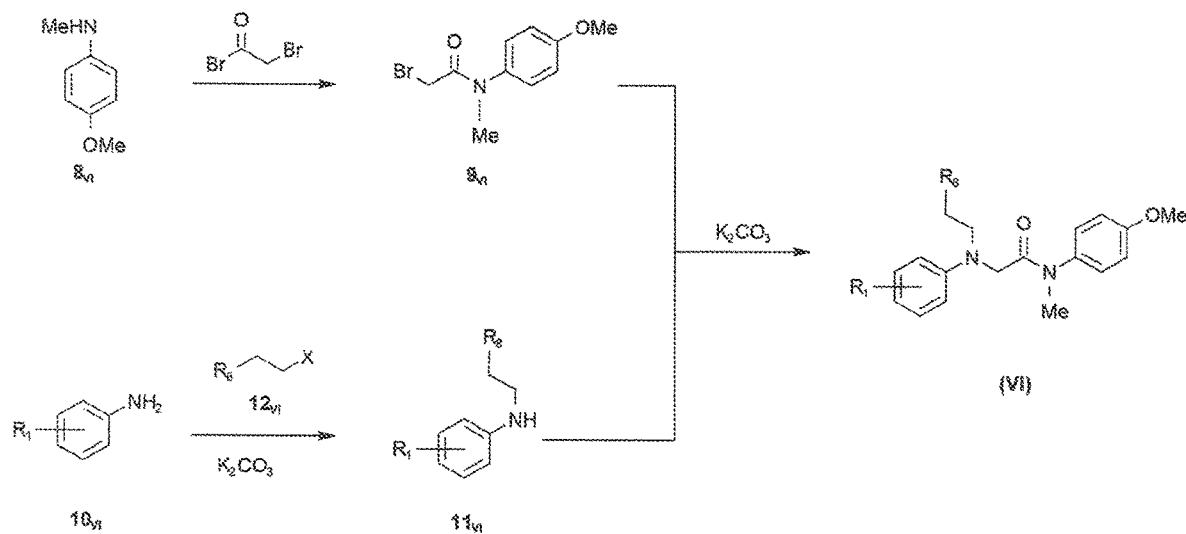
FIG. 6 shows a representative synthetic route for producing compounds of formula (VI).

Referring now to FIG. 6, compounds consistent with formula (VI) can be synthesized by, for example, acylating methylanilines $8_{VI}$ with bromoacetyl bromide to form intermediates $9_{VI}$. Intermediates $11_{VI}$ can be formed by alkylating anilines $10_{VI}$ with β-haloamines $12_{VI}$ in the presence of base. Combining intermediates $11_{VI}$ with intermediates $9_{VI}$ in the presence of base yields compounds of formula (VI).

The present disclosure provides compounds of formula (VII):

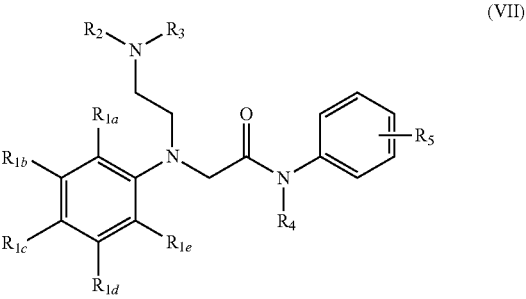

wherein:
R$_{1a}$ is H, Cl, F, —CF₃, —OMe, or methyl;
R$_{1b}$ is H, Cl, F, —CF₃, or —OCF₃;
R$_{1c}$ is H, Cl, F, or —OMe;
R$_{1d}$ is H, Cl, F, —CF₃, or —OCF₃;
R$_{1e}$ is H, Cl, F, —CF₃, —OMe, or methyl;
R₂ and R₃ are each independently H or alkyl or, taken together, form a 4- to 8-membered heterocyclic ring with the adjacent nitrogen atom;

$R_4$ is H or alkyl; and $R_5$ is H or one or more electron donating groups.

In compounds of formula (VII), $R_{1a}$ is H or an ortho-substituent selected from the group consisting of: chloro, fluoro, trifluoromethyl, methoxy, or methyl. $R_{1b}$ is H or a meta-substituent selected from the group consisting of: chloro, fluoro, trifluoromethyl, or trifluoromethoxy. $R_{1c}$ is H a para-substituent selected from the group consisting of: chloro, fluoro, or methoxy. $R_{1d}$ is H or (e.g., when $R_{1b}$ is not H) a meta-substituent selected from the group consisting of: chloro, fluoro, trifluoromethyl, or trifluoromethoxy. $R_{1e}$ is H or (e.g., when $R_{1a}$ is not H) an ortho-substituent selected from the group consisting of: chloro, fluoro, trifluoromethyl, methoxy, or methyl. In some embodiments, $R_{1a}$ is chloro, $R_{1d}$ is chloro, and $R_{1b}$, $R_{1c}$, and $R_{1e}$ are each H. In other embodiments, $R_{1a}$ is fluoro, $R_{1b}$ is chloro, and $R_{1c}$, $R_{1d}$, and $R_{1e}$ are each H. In other embodiments, $R_{1a}$ is trifluoromethyl, and $R_{1b}$, $R_{1c}$, $R_{1d}$, and $R_{1e}$ are each H. In other embodiments, $R_{1a}$ is methoxy, and $R_{1b}$, $R_{1c}$, $R_{1d}$, and $R_{1e}$ are each H. In other embodiments, $R_{1a}$ is methyl, and $R_{1b}$, $R_{1c}$, $R_{1d}$, and $R_{1e}$ are each H. In other embodiments, $R_{1b}$ is chloro, $R_{1e}$ is fluoro, and $R_{1a}$, $R_{1d}$, and $R_{1e}$ are each H. In other embodiments, $R_{1b}$ is trifluoromethyl, $R_{1c}$ is chloro, and $R_{1a}$, $R_{1d}$, and $R_{1e}$ are each H. In other embodiments, $R_{1b}$ is trifluoromethoxyl, and $R_{1a}$, $R_{1c}$, $R_{1d}$, and $R_{1e}$ are each H. In other embodiments, $R_{1b}$ is chloro, $R_{1c}$ is chloro, and $R_{1a}$, $R_{1d}$, and $R_{1e}$ are each H. In other embodiments, $R_{1b}$ is chloro, and $R_{1a}$, $R_{1c}$, $R_{1d}$, and $R_{1e}$ are each H. In other embodiments, $R_{1c}$ is methoxyl, and $R_{1a}$, $R_{1b}$, $R_{1d}$, and $R_{1e}$ are each H.

Each $R_2$ and $R_3$ is independently H or alkyl. When $R_2$ and/or $R_3$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

In some embodiments, $R_2$ and $R_3$ are covalently connected to form, with the adjacent nitrogen atom, a heterocyclic ring. The heterocyclic ring may include one to three nitrogen atoms and a total of four to eight atoms in the ring. The heterocyclic ring may be unsubstituted or substituted, for example with an alkyl or alkoxyl group. For example and without limitation, $R_2$ and $R_3$ may be covalently connected and include a total of five carbon atoms to form a piperidinyl ring including the nitrogen atom adjacent to $R_2$ and $R_3$. In other embodiments, $R_2$ and $R_3$ may, together, have a general formula —$(CH_2)_pN(R_7)(CH_2)_q$—, wherein p is 1 to 4, q is 1 to 4, p and q combined total 3 to 8, and $R_7$ is H or alkyl. When $R_7$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. In some embodiments, $R_2$ and $R_3$ are both H. In other embodiments, $R_2$ and $R_3$ are both methyl. In still other embodiments, $R_2$ is H and $R_3$ is methyl.

$R_4$ is H or alkyl. When $R_4$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds.

$R_5$ is H or one or more electron donating groups. When $R_5$ is one or more electron donating groups, $R_5$ may be a single electron donating group in the ortho-, meta-, or para-position of the aryl ring. In other embodiments, $R_5$ may be two to five electron donating groups in any combination of ortho-, meta-, and para-positions of the aryl ring. Each electron donating group may be independently selected from alkyl and alkoxyl. When $R_5$ is alkyl, the alkyl group may be linear or branched, and may consist of one to six carbon atoms (i.e., $C_{1-6}$ alkyl). The alkyl group may be cyclic, in which case the alkyl group may consist of three to six carbon atoms (i.e., $C_{3-6}$ cycloalkyl). The alkyl group may be saturated or unsaturated with one or more carbon-carbon double bonds and/or carbon-carbon triple bonds. When $R_5$ is alkoxyl, the alkoxy group may be linear or branched, and may consist of one to six carbon atoms (i.e., $C_{1-6}$ alkoxy). The alkoxy group may be cyclic, in which case the alkoxy group may consist of three to six carbon atoms (i.e., $C_{3-6}$ alkoxy). The alkoxy group may be saturated or unsaturated with one or more carbon-carbon double bonds and/or carbon-carbon triple bonds.

Some example compounds of formula (VII) are provided in Table 7 below.

TABLE 7

Example Compounds of Formula (VII)

| Compound | $R_{1x}$ | $R_2$ | $R_3$ | $R_4$ | $R_5$ | $R_7$ | n | p | q |
|---|---|---|---|---|---|---|---|---|---|
| 2290 | a-e: H | Me | Me | Me | p-OMe | n/a | 2 | n/a | n/a |
| 2291 | a: H<br>b: Cl<br>c-e: H | Me | Me | Me | p-OMe | n/a | 2 | n/a | n/a |
| 2292 | a: H<br>b: Cl<br>c: Cl<br>d-e: H | Me | Me | Me | p-OMe | n/a | 2 | n/a | n/a |
| 2293 | a: OMe<br>b-e: H | Me | Me | Me | p-OMe | n/a | 2 | n/a | n/a |
| 2294 | a-b: H<br>c: OMe<br>d-e: H | Me | Me | Me | p-OMe | n/a | 2 | n/a | n/a |
| 2295 | a: Me<br>b-e: H | Me | Me | Me | p-OMe | n/a | 2 | n/a | n/a |
| 2296 | a: H<br>b: OCF$_3$<br>c-e: H | Me | Me | Me | p-OMe | n/a | 2 | n/a | n/a |

TABLE 7-continued

Example Compounds of Formula (VII)

| Compound | $R_{1x}$ | $R_2$ | $R_3$ | $R_4$ | $R_5$ | $R_7$ | n | p | q |
|---|---|---|---|---|---|---|---|---|---|
| 2297 | a: H<br>b: $CF_3$<br>c: Cl<br>d-e: H | Me | Me | Me | p-OMe | n/a | 2 | n/a | n/a |
| 2298 | a: Cl<br>b-c: H<br>d: Cl<br>e: H | Me | Me | Me | p-OMe | n/a | 2 | n/a | n/a |
| 2299 | a: H<br>b: Cl<br>c: F<br>d-e: H | Me | Me | Me | p-OMe | n/a | 2 | n/a | n/a |
| 2300 | a: F<br>b: Cl<br>c-e: H | Me | Me | Me | p-OMe | n/a | 2 | n/a | n/a |
| 2301 | a: $CF_3$<br>b-e: H | Me | Me | Me | p-OMe | n/a | 2 | n/a | n/a |
| 2302 | a-e: H | H | H | Me | p-OMe | n/a | 2 | n/a | n/a |
| 2303 | a-e: H | | —$(CH_2)_5$— | Me | p-OMe | n/a | 2 | n/a | n/a |
| 2304 | a-e: H | | —$(CH_2)_pN(R_7)(CH_2)_q$— | Me | p-OMe | Me | 2 | 2 | 2 |

Figure 7:
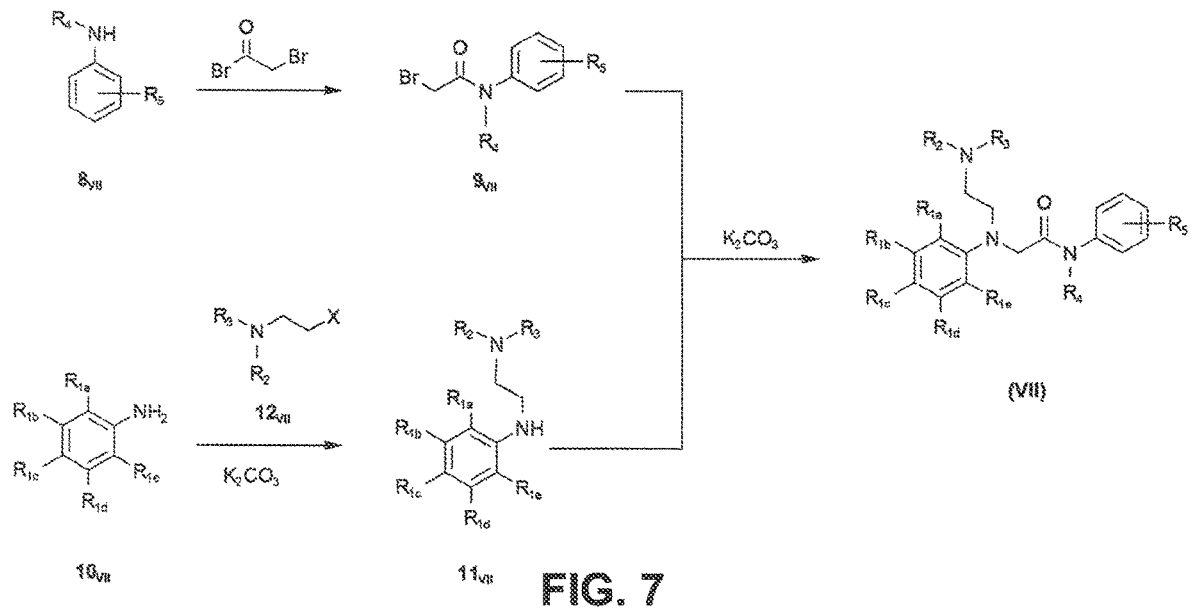
FIG. 7 shows a representative synthetic route for producing compounds of formula (VII).

Referring now to FIG. 7, compounds consistent with formula (VII) can be synthesized by, for example, acylating anilines $8_{VII}$ with bromoacetyl bromide to form intermediates $9_{VII}$. Intermediates $11_{VII}$ can be formed by alkylating anilines $10_{VII}$ with β-haloamines $12_{VIII}$ the presence of base. Combining intermediates $11_{VII}$ with intermediates $9_{VIII}$ the presence of base yields compounds of formula (VII).

In other embodiments, the present disclosure provides a compound of formula (VIIIa):

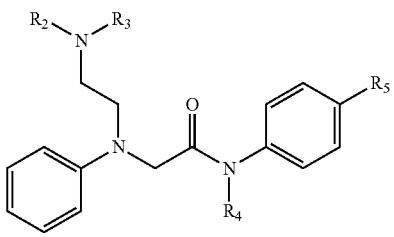

(VIIIa)

wherein:
$R_2$=H or Me;
$R_3$=H or Me;
$R_4$=Alkyl;
$R_5$=O-Alkyl; and
Alkyl=aliphatic $C_1$-$C_4$ alkyl.

In compounds of formula (VIIIa), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIa) are provided in Table 8a below.

TABLE 8a

Example Compounds of Formula (VIIIa)

| Compound | $R_2$ | $R_3$ | $R_4$ | $R_5$ |
|---|---|---|---|---|
| 2290 | Me | Me | Me | —OMe |
| 2305 | Me | Me | Me | —OEt |
| 2306 | Me | Me | Me | —O-nPr |
| 2307 | Me | Me | Me | —O-iPr |
| 2308 | Me | Me | Me | —O-nBu |
| 2309 | Me | Me | Me | —O-iBu |
| 2310 | Me | Me | Me | —O-tBu |
| 2311 | Me | Me | Et | —OMe |
| 2312 | Me | Me | nPr | —OMe |
| 2313 | Me | Me | iPr | —OMe |
| 2314 | Me | Me | nBu | —OMe |
| 2315 | Me | Me | iBu | —OMe |
| 2316 | Me | Me | tBu | —OMe |
| 2302 | H | H | Me | —OMe |
| 2318 | H | H | Me | —OEt |
| 2319 | H | H | Me | —O-nPr |
| 2320 | H | H | Me | —O-iPr |
| 2321 | H | H | Me | —O-nBu |
| 2322 | H | H | Me | —O-iBu |
| 2323 | H | H | Me | —O-tBu |
| 2324 | H | H | Et | —OMe |
| 2325 | H | H | nPr | —OMe |
| 2326 | H | H | iPr | —OMe |
| 2327 | H | H | nBu | —OMe |
| 2328 | H | H | iBu | —OMe |
| 2329 | H | H | tBu | —OMe |
| 2330 | H | Me | Me | —OMe |
| 2331 | H | Me | Me | —OEt |
| 2332 | H | Me | Me | —O-nPr |
| 2333 | H | Me | Me | —O-iPr |
| 2334 | H | Me | Me | —O-nBu |
| 2335 | H | Me | Me | —O-iBu |
| 2336 | H | Me | Me | —O-tBu |
| 2337 | H | Me | Et | —OMe |
| 2338 | H | Me | nPr | —OMe |
| 2339 | H | Me | iPr | —OMe |
| 2340 | H | Me | nBu | —OMe |

TABLE 8a-continued

Example Compounds of Formula (VIIIa)

| Compound | $R_2$ | $R_3$ | $R_4$ | $R_5$ |
|---|---|---|---|---|
| 2341 | H | Me | iBu | —OMe |
| 2342 | H | Me | tBu | —OMe |

Figure 8:
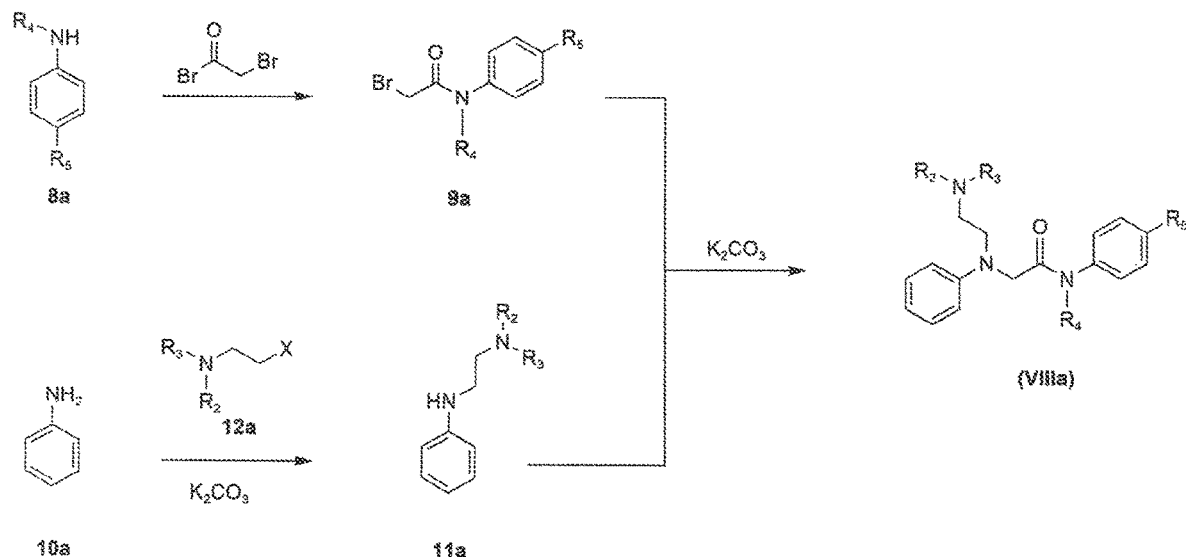
FIG. 8 shows a representative synthetic route for producing compounds of formula (VIIIa).

Referring now to FIG. 8, compounds consistent with formula (VIIIa) can be synthesized by, for example, acylating para-substituted anilines 8a with bromoacetyl bromide to form intermediates 9a. Intermediates 11a can be formed by alkylating aniline 10a with β-haloamines 12a in the presence of base. Combining intermediates 11a with intermediates 9a in the presence of base yields compounds of formula (VIIIa).

In other embodiments, the present disclosure provides a compound of formula (VIIIb):

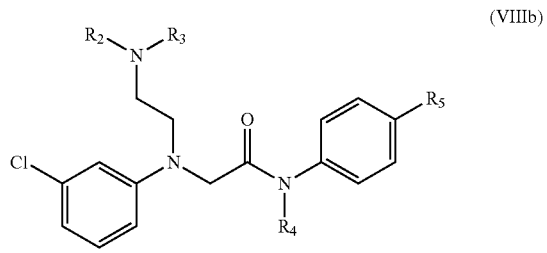

(VIIIb)

wherein:
$R_2$=H or Me;
$R_3$=H or Me;
$R_4$=Alkyl;
$R_5$=O-Alkyl; and
Alkyl=aliphatic $C_1$-$C_4$ alkyl.

In compounds of formula (VIIIb), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIb) are provided in Table 8b below.

TABLE 8b

Example Compounds of Formula (VIIIb)

| Compound | $R_2$ | $R_3$ | $R_4$ | $R_5$ |
|---|---|---|---|---|
| 2291 | Me | Me | Me | —OMe |
| 2343 | Me | Me | Me | —OEt |

TABLE 8b-continued

Example Compounds of Formula (VIIIb)

| Compound | $R_2$ | $R_3$ | $R_4$ | $R_5$ |
|---|---|---|---|---|
| 2344 | Me | Me | Me | —O-nPr |
| 2345 | Me | Me | Me | —O-iPr |
| 2346 | Me | Me | Me | —O-nBu |
| 2347 | Me | Me | Me | —O-iBu |
| 2348 | Me | Me | Me | —O-tBu |
| 2349 | Me | Me | Et | —OMe |
| 2350 | Me | Me | nPr | —OMe |
| 2351 | Me | Me | iPr | —OMe |
| 2352 | Me | Me | nBu | —OMe |
| 2353 | Me | Me | iBu | —OMe |
| 2354 | Me | Me | tBu | —OMe |
| 2355 | H | H | Me | —OMe |
| 2356 | H | H | Me | —OEt |
| 2357 | H | H | Me | —O-nPr |
| 2358 | H | H | Me | —O-iPr |
| 2359 | H | H | Me | —O-nBu |
| 2360 | H | H | Me | —O-iBu |
| 2361 | H | H | Me | —O-tBu |
| 2362 | H | H | Et | —OMe |
| 2363 | H | H | nPr | —OMe |
| 2364 | H | H | iPr | —OMe |
| 2365 | H | H | nBu | —OMe |
| 2366 | H | H | iBu | —OMe |
| 2367 | H | H | tBu | —OMe |
| 2368 | H | Me | Me | —OMe |
| 2369 | H | Me | Me | —OEt |
| 2370 | H | Me | Me | —O-nPr |
| 2371 | H | Me | Me | —O-iPr |
| 2372 | H | Me | Me | —O-nBu |
| 2373 | H | Me | Me | —O-iBu |
| 2374 | H | Me | Me | —O-tBu |
| 2375 | H | Me | Et | —OMe |
| 2376 | H | Me | nPr | —OMe |
| 2377 | H | Me | iPr | —OMe |
| 2378 | H | Me | nBu | —OMe |
| 2379 | H | Me | iBu | —OMe |
| 2380 | H | Me | tBu | —OMe |

Figure 9:
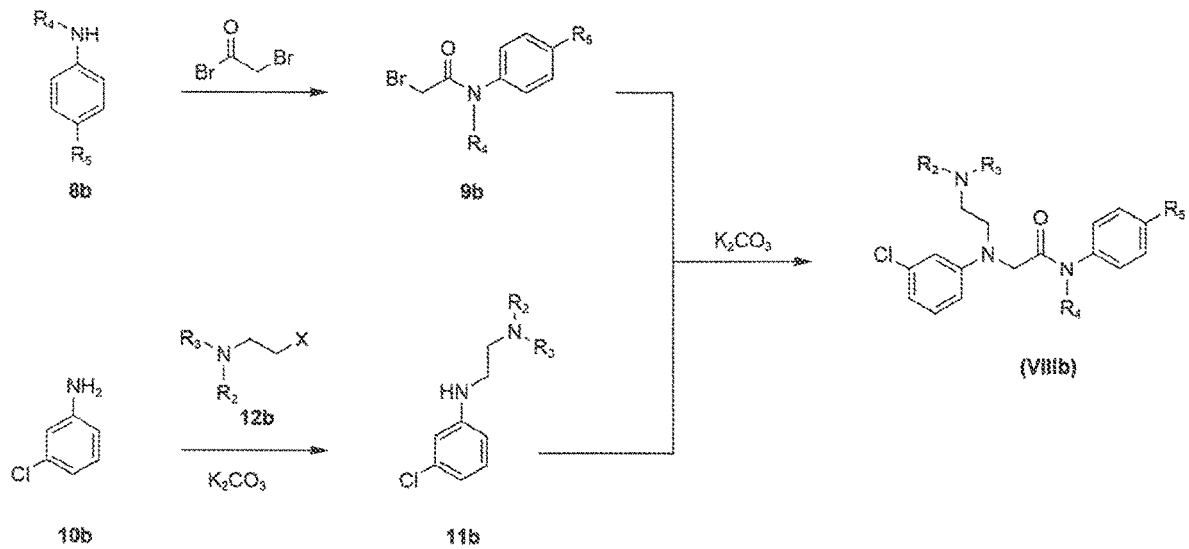
FIG. 9 shows a representative synthetic route for producing compounds of formula (VIIIb).

Referring now to FIG. 9, compounds consistent with formula (VIIIb) can be synthesized by, for example, acylating para-substituted anilines 8b with bromoacetyl bromide to form intermediates 9b. Intermediates 11b can be formed by alkylating m-chloroaniline 10b with β-haloamines 12b in the presence of base. Combining intermediates 11b with intermediates 9b in the presence of base yields compounds of formula (VIIIb).

In other embodiments, the present disclosure provides a compound of formula (VIIIc):

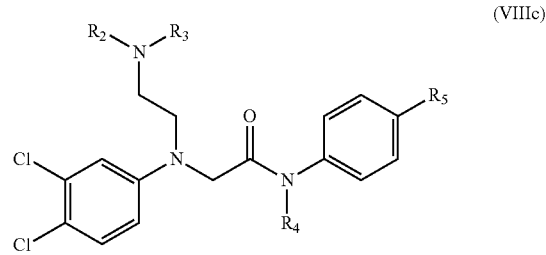

(VIIIc)

wherein:
$R_2$=H or Me;
$R_3$=H or Me;
$R_4$=Alkyl;
$R_5$=O-Alkyl; and
Alkyl=aliphatic $C_1$-$C_4$ alkyl.

In compounds of formula (VIIIc), each $R_2$ and $R_3$ is independently H or methyl; in some embodiments both $R_2$ and R$_3$ are H. In other embodiments, both R$_2$ and R$_3$ are methyl. In some embodiments, one of R$_2$ and R$_3$ is H while the other is methyl.

R$_4$ is Alkyl; may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

R$_5$ is an O-Alkyl (i.e., alkoxy) at the para position. The alkyl group may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

Some example compounds of formula (VIIIc) are provided in Table 8c below.

TABLE 8c

Example Compounds of Formula (VIIIc)

| Compound | R$_2$ | R$_3$ | R$_4$ | R$_5$ |
|---|---|---|---|---|
| 2292 | Me | Me | Me | —OMe |
| 2381 | Me | Me | Me | —OEt |
| 2382 | Me | Me | Me | —O-nPr |
| 2383 | Me | Me | Me | —O-iPr |
| 2384 | Me | Me | Me | —O-nBu |
| 2385 | Me | Me | Me | —O-iBu |
| 2386 | Me | Me | Me | —O-tBu |
| 2387 | Me | Me | Et | —OMe |
| 2388 | Me | Me | nPr | —OMe |
| 2389 | Me | Me | iPr | —OMe |
| 2390 | Me | Me | nBu | —OMe |
| 2391 | Me | Me | iBu | —OMe |
| 2392 | Me | Me | tBu | —OMe |
| 2393 | H | H | Me | —OMe |
| 2394 | H | H | Me | —OEt |
| 2395 | H | H | Me | —O-nPr |
| 2396 | H | H | Me | —O-iPr |
| 2397 | H | H | Me | —O-nBu |
| 2398 | H | H | Me | —O-iBu |
| 2399 | H | H | Me | —O-tBu |
| 2400 | H | H | Et | —OMe |
| 2401 | H | H | nPr | —OMe |
| 2402 | H | H | iPr | —OMe |
| 2403 | H | H | nBu | —OMe |
| 2404 | H | H | iBu | —OMe |
| 2405 | H | H | tBu | —OMe |
| 2406 | H | Me | Me | —OMe |
| 2407 | H | Me | Me | —OEt |
| 2408 | H | Me | Me | —O-nPr |
| 2409 | H | Me | Me | —O-iPr |
| 2410 | H | Me | Me | —O-nBu |
| 2411 | H | Me | Me | —O-iBu |
| 2412 | H | Me | Me | —O-tBu |
| 2413 | H | Me | Et | —OMe |
| 2414 | H | Me | nPr | —OMe |
| 2415 | H | Me | iPr | —OMe |
| 2416 | H | Me | nBu | —OMe |
| 2417 | H | Me | iBu | —OMe |
| 2418 | H | Me | tBu | —OMe |

Figure 10:
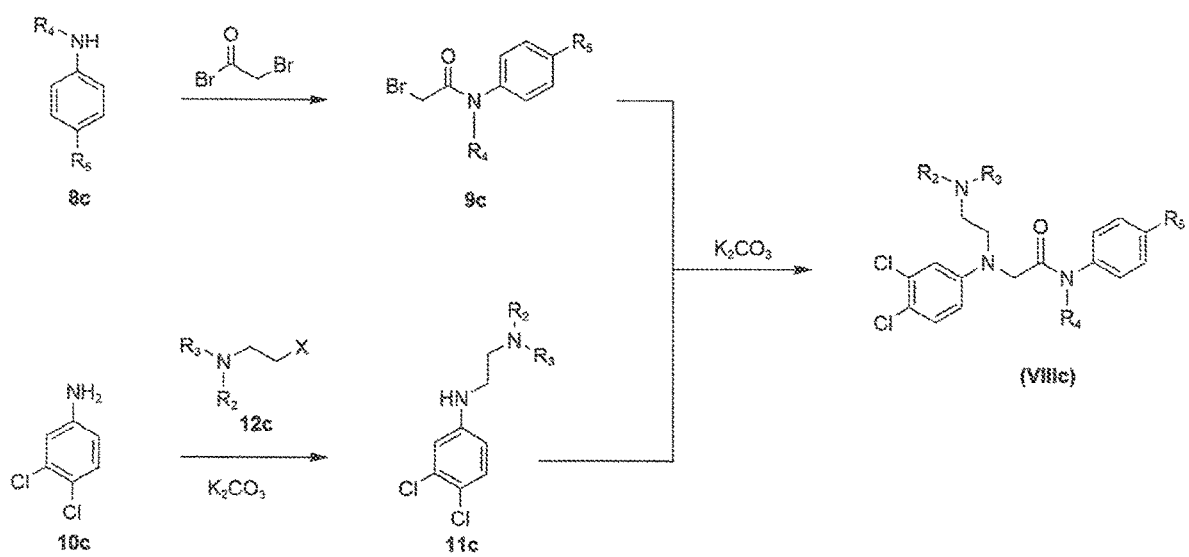
FIG. 10 shows a representative synthetic route for producing compounds of formula (VIIIc).

Referring now to FIG. 10, compounds consistent with formula (VIIIc) can be synthesized by, for example, acylating para-substituted anilines 8c with bromoacetyl bromide to form intermediates 9c. Intermediates 11c can be formed by alkylating m-chloroaniline 10c with β-haloamines 12c in the presence of base. Combining intermediates 11c with intermediates 9c in the presence of base yields compounds of formula (VIIIc).

In other embodiments, the present disclosure provides a compound of formula (VIIId):

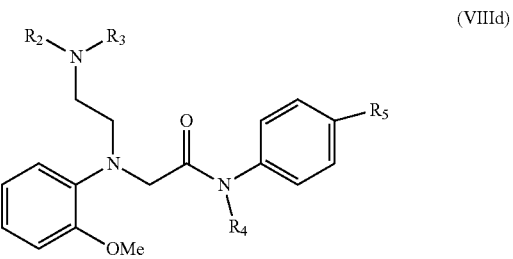

(VIIId)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In compounds of formula (VIIId), each R$_2$ and R$_3$ is independently H or methyl; in some embodiments both R$_2$ and R$_3$ are H. In other embodiments, both R$_2$ and R$_3$ are methyl. In some embodiments, one of R$_2$ and R$_3$ is H while the other is methyl.

R$_4$ is Alkyl; may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

R$_5$ is an O-Alkyl (i.e., alkoxy) at the para position. The alkyl group may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

Some example compounds of formula (VIIId) are provided in Table 8d below.

TABLE 8d

Example Compounds of Formula (VIIId)

| Compound | R$_2$ | R$_3$ | R$_4$ | R$_5$ |
|---|---|---|---|---|
| 2293 | Me | Me | Me | —OMe |
| 2420 | Me | Me | Me | —OEt |
| 2421 | Me | Me | Me | —O-nPr |
| 2422 | Me | Me | Me | —O-iPr |
| 2423 | Me | Me | Me | —O-nBu |
| 2424 | Me | Me | Me | —O-iBu |
| 2425 | Me | Me | Me | —O-tBu |
| 2426 | Me | Me | Et | —OMe |
| 2427 | Me | Me | nPr | —OMe |
| 2428 | Me | Me | iPr | —OMe |
| 2429 | Me | Me | nBu | —OMe |
| 2430 | Me | Me | iBu | —OMe |
| 2431 | Me | Me | tBu | —OMe |
| 2432 | H | H | Me | —OMe |
| 2433 | H | H | Me | —OEt |
| 2434 | H | H | Me | —O-nPr |
| 2435 | H | H | Me | —O-iPr |
| 2436 | H | H | Me | —O-nBu |
| 2437 | H | H | Me | —O-iBu |
| 2438 | H | H | Me | —O-tBu |
| 2439 | H | H | Et | —OMe |

TABLE 8d-continued

Example Compounds of Formula (VIIId)

| Compound | $R_2$ | $R_3$ | $R_4$ | $R_5$ |
|---|---|---|---|---|
| 2440 | H | H | nPr | —OMe |
| 2441 | H | H | iPr | —OMe |
| 2442 | H | H | nBu | —OMe |
| 2443 | H | H | iBu | —OMe |
| 2444 | H | H | tBu | —OMe |
| 2445 | H | Me | Me | —OMe |
| 2446 | H | Me | Me | —OEt |
| 2447 | H | Me | Me | —O-nPr |
| 2448 | H | Me | Me | —O-iPr |
| 2449 | H | Me | Me | —O-nBu |
| 2450 | H | Me | Me | —O-iBu |
| 2451 | H | Me | Me | —O-tBu |
| 2452 | H | Me | Et | —OMe |
| 2453 | H | Me | nPr | —OMe |
| 2454 | H | Me | iPr | —OMe |
| 2455 | H | Me | nBu | —OMe |
| 2456 | H | Me | iBu | —OMe |
| 2457 | H | Me | tBu | —OMe |

Figure 11:
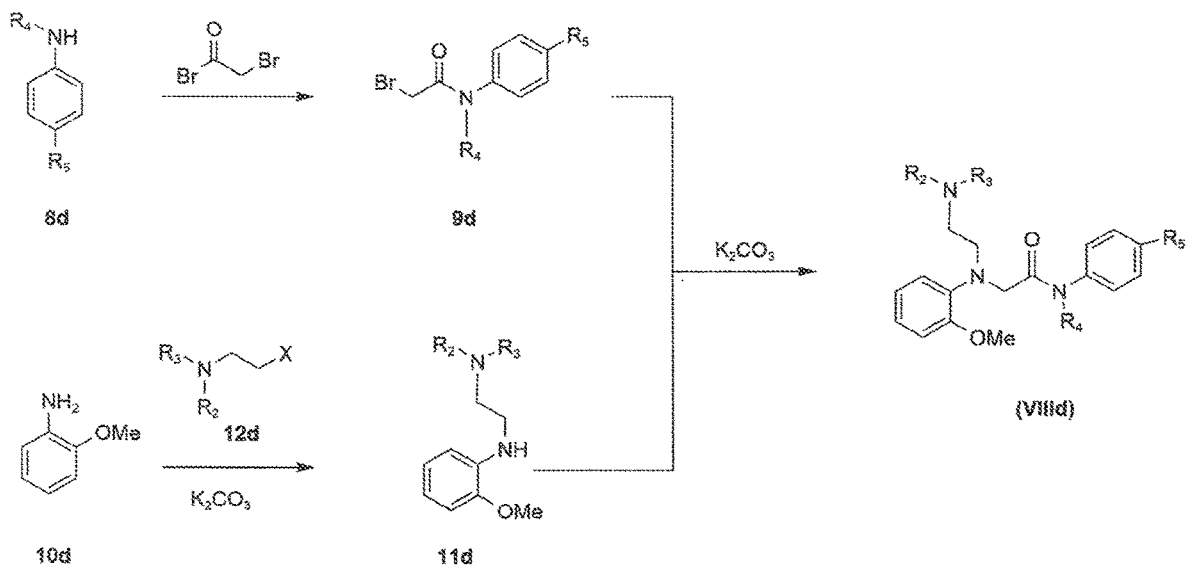
FIG. 11 shows a representative synthetic route for producing compounds of formula (VIIId).

Referring now to FIG. 11, compounds consistent with formula (VIIId) can be synthesized by, for example, acylating para-substituted anilines 8d with bromoacetyl bromide to form intermediates 9d. Intermediates 11d can be formed by alkylating o-methoxyaniline 10d with β-haloamines 12d in the presence of base. Combining intermediates 11d with intermediates 9d in the presence of base yields compounds of formula (VIIId).

In other embodiments, the present disclosure provides a compound of formula (VIIIe):

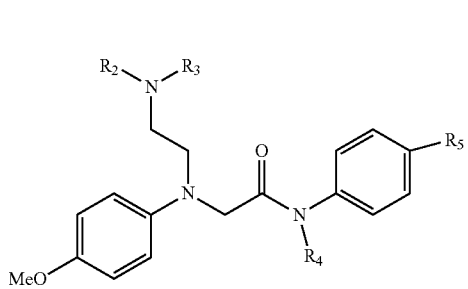

(VIIIe)

wherein:
    $R_2$=H or Me;
    $R_3$=H or Me;
    $R_4$=Alkyl;
    $R_5$=O-Alkyl; and
    Alkyl=aliphatic $C_1$-$C_4$ alkyl.

In compounds of formula (VIIIe), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIe) are provided in Table 8e below.

TABLE 8e

Example Compounds of Formula (VIIIe)

| Compound | $R_2$ | $R_3$ | $R_4$ | $R_5$ |
|---|---|---|---|---|
| 2294 | Me | Me | Me | —OMe |
| 2459 | Me | Me | Me | —OEt |
| 2460 | Me | Me | Me | —O-nPr |
| 2461 | Me | Me | Me | —O-iPr |
| 2462 | Me | Me | Me | —O-nBu |
| 2463 | Me | Me | Me | —O-iBu |
| 2464 | Me | Me | Me | —O-tBu |
| 2465 | Me | Me | Et | —OMe |
| 2466 | Me | Me | nPr | —OMe |
| 2467 | Me | Me | iPr | —OMe |
| 2468 | Me | Me | nBu | —OMe |
| 2469 | Me | Me | iBu | —OMe |
| 2470 | Me | Me | tBu | —OMe |
| 2471 | H | H | Me | —OMe |
| 2472 | H | H | Me | —OEt |
| 2473 | H | H | Me | —O-nPr |
| 2474 | H | H | Me | —O-iPr |
| 2475 | H | H | Me | —O-nBu |
| 2476 | H | H | Me | —O-iBu |
| 2477 | H | H | Me | —O-tBu |
| 2478 | H | H | Et | —OMe |
| 2479 | H | H | nPr | —OMe |
| 2480 | H | H | iPr | —OMe |
| 2481 | H | H | nBu | —OMe |
| 2482 | H | H | iBu | —OMe |
| 2483 | H | H | tBu | —OMe |
| 2484 | H | Me | Me | —OMe |
| 2485 | H | Me | Me | —OEt |
| 2486 | H | Me | Me | —O-nPr |
| 2487 | H | Me | Me | —O-iPr |
| 2488 | H | Me | Me | —O-nBu |
| 2489 | H | Me | Me | —O-iBu |
| 2490 | H | Me | Me | —O-tBu |
| 2491 | H | Me | Et | —OMe |
| 2492 | H | Me | nPr | —OMe |
| 2493 | H | Me | iPr | —OMe |
| 2494 | H | Me | nBu | —OMe |
| 2495 | H | Me | iBu | —OMe |
| 2496 | H | Me | tBu | —OMe |

Figure 12:
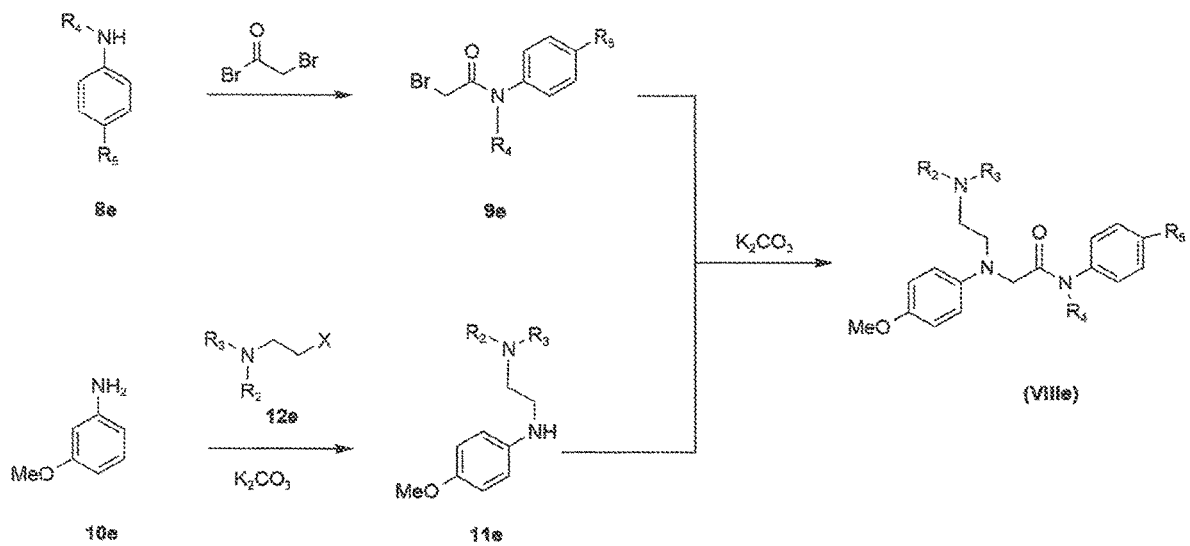
FIG. 12 shows a representative synthetic route for producing compounds of formula (VIIIe).

Referring now to FIG. 12, compounds consistent with formula (VIIIe) can be synthesized by, for example, acylating para-substituted anilines 8e with bromoacetyl bromide to form intermediates 9e. Intermediates 11e can be formed by alkylating β-methoxyaniline 10e with β-haloamines 12e in the presence of base. Combining intermediates 11e with intermediates 9e in the presence of base yields compounds of formula (VIIIe).

In other embodiments, the present disclosure provides a compound of formula (VIIIf):

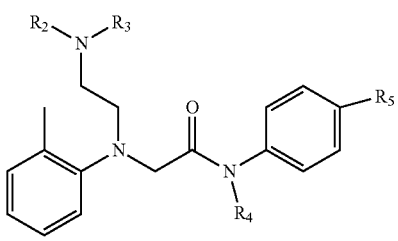

(VIIIf)

wherein:
  $R_2$=H or Me;
  $R_3$=H or Me;
  $R_4$=Alkyl;
  $R_5$=O-Alkyl; and
  Alkyl=aliphatic $C_1$-$C_4$ alkyl.

In compounds of formula (VIIIf), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIf) are provided in Table 8f below.

TABLE 8f

Example Compounds of Formula (VIIIf)

| Compound | $R_2$ | $R_3$ | $R_4$ | $R_5$ |
|---|---|---|---|---|
| 2295 | Me | Me | Me | —OMe |
| 2498 | Me | Me | Me | —OEt |
| 2499 | Me | Me | Me | —O-nPr |
| 2500 | Me | Me | Me | —O-iPr |
| 2501 | Me | Me | Me | —O-nBu |
| 2502 | Me | Me | Me | —O-iBu |
| 2503 | Me | Me | Me | —O-tBu |
| 2504 | Me | Me | Et | —OMe |
| 2505 | Me | Me | nPr | —OMe |
| 2506 | Me | Me | iPr | —OMe |
| 2507 | Me | Me | nBu | —OMe |
| 2508 | Me | Me | iBu | —OMe |
| 2509 | Me | Me | tBu | —OMe |
| 2510 | H | H | Me | —OMe |
| 2511 | H | H | Me | —OEt |
| 2512 | H | H | Me | —O-nPr |
| 2513 | H | H | Me | —O-iPr |
| 2514 | H | H | Me | —O-nBu |
| 2515 | H | H | Me | —O-iBu |
| 2516 | H | H | Me | —O-tBu |
| 2517 | H | H | Et | —OMe |
| 2518 | H | H | nPr | —OMe |
| 2519 | H | H | iPr | —OMe |
| 2520 | H | H | nBu | —OMe |
| 2521 | H | H | iBu | —OMe |
| 2522 | H | H | tBu | —OMe |
| 2523 | H | Me | Me | —OMe |
| 2524 | H | Me | Me | —OEt |
| 2525 | H | Me | Me | —O-nPr |
| 2526 | H | Me | Me | —O-iPr |
| 2527 | H | Me | Me | —O-nBu |
| 2528 | H | Me | Me | —O-iBu |
| 2529 | H | Me | Me | —O-tBu |
| 2530 | H | Me | Et | —OMe |
| 2531 | H | Me | nPr | —OMe |
| 2532 | H | Me | iPr | —OMe |
| 2533 | H | Me | nBu | —OMe |
| 2534 | H | Me | iBu | —OMe |
| 2535 | H | Me | tBu | —OMe |

Figure 13:
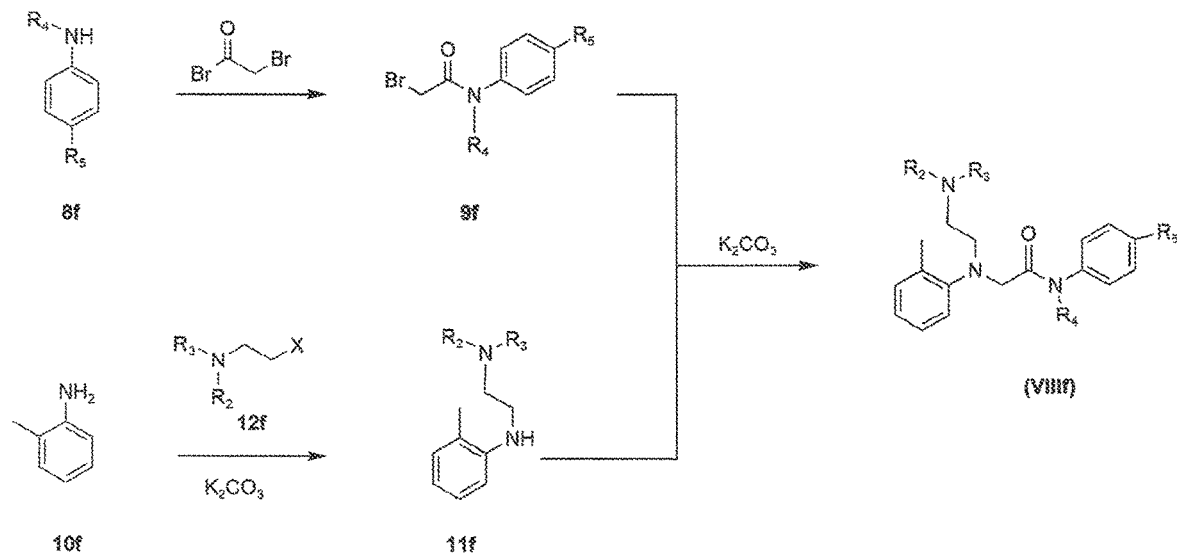
FIG. 13 shows a representative synthetic route for producing compounds of formula (VIIIf).

Referring now to FIG. 13, compounds consistent with formula (VIIIf) can be synthesized by, for example, acylating para-substituted anilines 8f with bromoacetyl bromide to form intermediates 9f. Intermediates 11f can be formed by alkylating β-methoxyaniline 10f with β-haloamines 12f in the presence of base. Combining intermediates 11f with intermediates 9f in the presence of base yields compounds of formula (VIIIf).

In other embodiments, the present disclosure provides a compound of formula (VIIIg):

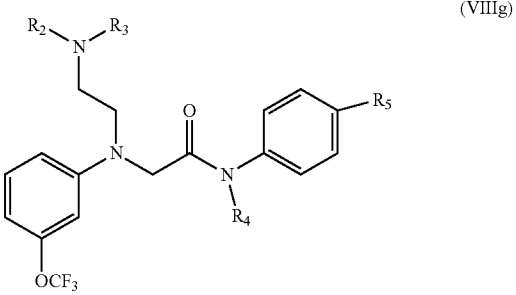

(VIIIg)

wherein:
  $R_2$=H or Me;
  $R_3$=H or Me;
  $R_4$=Alkyl; and
  $R_5$=O-Alkyl; and
  Alkyl=aliphatic $C_1$-$C_4$ alkyl.

In compounds of formula (VIIIg), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIg) are provided in Table 8g below.

TABLE 8g

Example Compounds of Formula (VIIIg)

| Compound | $R_2$ | $R_3$ | $R_4$ | $R_5$ |
|---|---|---|---|---|
| 2296 | Me | Me | Me | —OMe |
| 2537 | Me | Me | Me | —OEt |
| 2538 | Me | Me | Me | —O-nPr |
| 2539 | Me | Me | Me | —O-iPr |
| 2540 | Me | Me | Me | —O-nBu |
| 2541 | Me | Me | Me | —O-iBu |
| 2542 | Me | Me | Me | —O-tBu |
| 2543 | Me | Me | Et | —OMe |
| 2544 | Me | Me | nPr | —OMe |
| 2545 | Me | Me | iPr | —OMe |
| 2546 | Me | Me | nBu | —OMe |
| 2547 | Me | Me | iBu | —OMe |
| 2548 | Me | Me | tBu | —OMe |
| 2549 | H | H | Me | —OMe |
| 2550 | H | H | Me | —OEt |
| 2551 | H | H | Me | —O-nPr |
| 2552 | H | H | Me | —O-iPr |
| 2553 | H | H | Me | —O-nBu |
| 2554 | H | H | Me | —O-iBu |
| 2555 | H | H | Me | —O-tBu |
| 2556 | H | H | Et | —OMe |
| 2557 | H | H | nPr | —OMe |
| 2558 | H | H | iPr | —OMe |
| 2559 | H | H | nBu | —OMe |
| 2560 | H | H | iBu | —OMe |
| 2561 | H | H | tBu | —OMe |
| 2562 | H | Me | Me | —OMe |
| 2563 | H | Me | Me | —OEt |
| 2564 | H | Me | Me | —O-nPr |
| 2565 | H | Me | Me | —O-iPr |
| 2566 | H | Me | Me | —O-nBu |
| 2567 | H | Me | Me | —O-iBu |
| 2568 | H | Me | Me | —O-tBu |
| 2569 | H | Me | Et | —OMe |
| 2570 | H | Me | nPr | —OMe |
| 2571 | H | Me | iPr | —OMe |
| 2572 | H | Me | nBu | —OMe |
| 2573 | H | Me | iBu | —OMe |
| 2574 | H | Me | tBu | —OMe |

Figure 14:
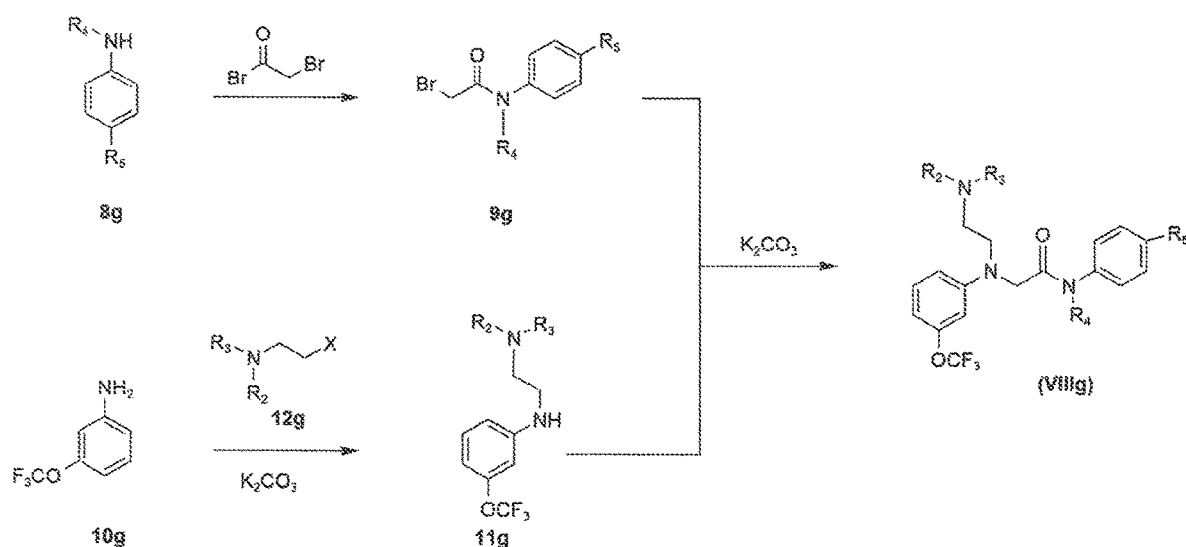
FIG. 14 shows a representative synthetic route for producing compounds of formula (VIIIg).

Referring now to FIG. 14, compounds consistent with formula (VIIIg) can be synthesized by, for example, acylating para-substituted anilines 8g with bromoacetyl bromide to form intermediates 9g. Intermediates 11g can be formed by alkylating m-trifluoromethoxyaniline 10g with β-haloamines 12g in the presence of base. Combining intermediates 11g with intermediates 9g in the presence of base yields compounds of formula (VIIIg).

In other embodiments, the present disclosure provides a compound of formula (VIIIh):

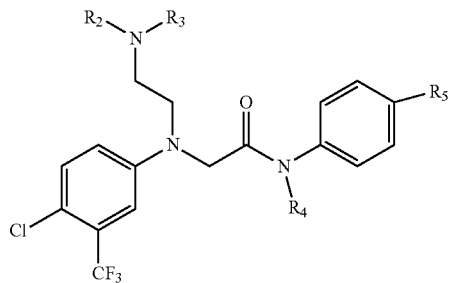

wherein:
$R_2$=H or Me;
$R_3$=H or Me;
$R_4$=Alkyl;
$R_5$=O-Alkyl; and
Alkyl=aliphatic $C_1$-$C_4$ alkyl.

In compounds of formula (VIIIh), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIh) are provided in Table 8h below.

TABLE 8h

Example Compounds of Formula (VIIIh)

| Compound | $R_2$ | $R_3$ | $R_4$ | $R_5$ |
|---|---|---|---|---|
| 2297 | Me | Me | Me | —OMe |
| 2576 | Me | Me | Me | —OEt |
| 2577 | Me | Me | Me | —O-nPr |
| 2578 | Me | Me | Me | —O-iPr |
| 2579 | Me | Me | Me | —O-nBu |
| 2580 | Me | Me | Me | —O-iBu |
| 2581 | Me | Me | Me | —O-tBu |
| 2582 | Me | Me | Et | —OMe |
| 2583 | Me | Me | nPr | —OMe |
| 2584 | Me | Me | iPr | —OMe |
| 2585 | Me | Me | nBu | —OMe |
| 2586 | Me | Me | iBu | —OMe |
| 2587 | Me | Me | tBu | —OMe |
| 2588 | H | H | Me | —OMe |
| 2589 | H | H | Me | —OEt |
| 2590 | H | H | Me | —O-nPr |
| 2591 | H | H | Me | —O-iPr |
| 2592 | H | H | Me | —O-nBu |
| 2593 | H | H | Me | —O-iBu |
| 2594 | H | H | Me | —O-tBu |
| 2595 | H | H | Et | —OMe |
| 2596 | H | H | nPr | —OMe |

TABLE 8h-continued

Example Compounds of Formula (VIIIh)

| Compound | R₂ | R₃ | R₄ | R₅ |
|---|---|---|---|---|
| 2597 | H | H | iPr | —OMe |
| 2598 | H | H | nBu | —OMe |
| 2599 | H | H | iBu | —OMe |
| 2600 | H | H | tBu | —OMe |
| 2601 | H | Me | Me | —OMe |
| 2602 | H | Me | Me | —OEt |
| 2603 | H | Me | Me | —O-nPr |
| 2604 | H | Me | Me | —O-iPr |
| 2605 | H | Me | Me | —O-nBu |
| 2606 | H | Me | Me | —O-iBu |
| 2607 | H | Me | Me | —O-tBu |
| 2608 | H | Me | Et | —OMe |
| 2609 | H | Me | nPr | —OMe |
| 2610 | H | Me | iPr | —OMe |
| 2611 | H | Me | nBu | —OMe |
| 2612 | H | Me | iBu | —OMe |
| 2613 | H | Me | tBu | —OMe |

Figure 15:
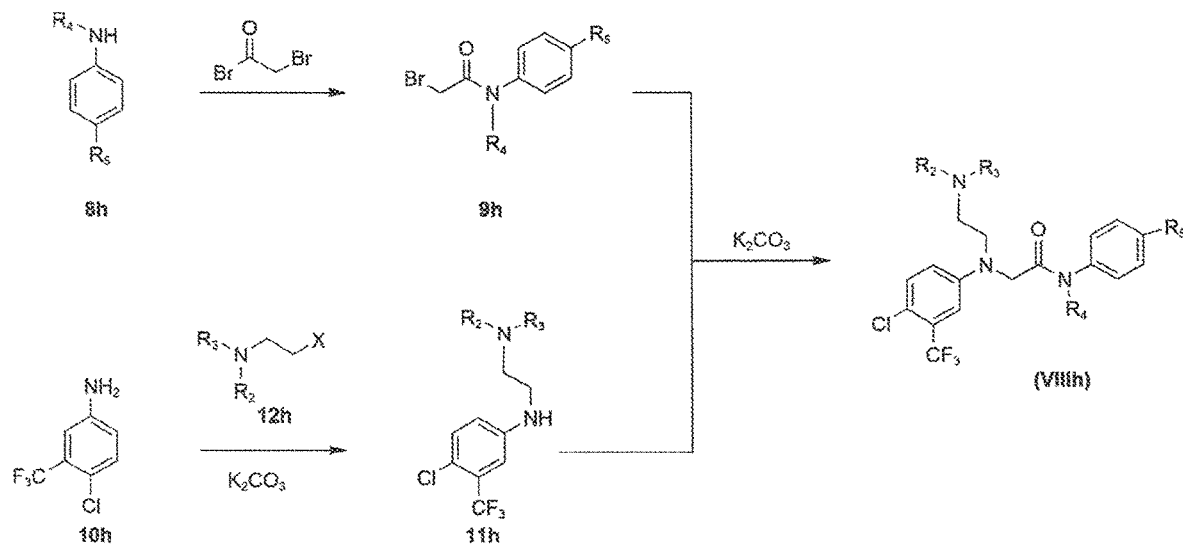
FIG. 15 shows a representative synthetic route for producing compounds of formula (VIIIh).

Referring now to FIG. 15, compounds consistent with formula (VIIIh) can be synthesized by, for example, acylating para-substituted anilines 8h with bromoacetyl bromide to form intermediates 9h. Intermediates 11h can be formed by alkylating β-chloro-m-trifluoromethylaniline 10h with β-haloamines 12h in the presence of base. Combining intermediates 11h with intermediates 9h in the presence of base yields compounds of formula (VIIIh).

In other embodiments, the present disclosure provides a compound of formula (VIIIi):

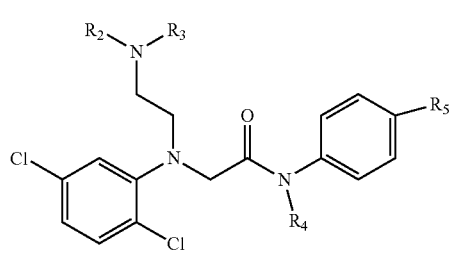

(VIIIi)

wherein:
R₂=H or Me;
R₃=H or Me;
R₄=Alkyl;
R₅=O-Alkyl; and
Alkyl=aliphatic C₁-C₄ alkyl.

In compounds of formula (VIIIi), each R₂ and R₃ is independently H or methyl; in some embodiments both R₂ and R₃ are H. In other embodiments, both R₂ and R₃ are methyl. In some embodiments, one of R₂ and R₃ is H while the other is methyl.

R₄ is Alkyl; may be linear or branched, and may consist of one to four carbon atoms (i.e., C₁₋₄ alkyl). The alkyl group may be cyclic, in which case the alkyl group may consist of three or four carbon atoms (i.e., C₃₋₄ cycloalkyl). The alkyl group may be saturated or unsaturated with one or more carbon-carbon double bonds and/or carbon-carbon triple bonds.

R₅ is an O-Alkyl (i.e., alkoxy) at the para position. The alkyl group may be linear or branched, and may consist of one to four carbon atoms (i.e., C₁₋₄ alkyl). The alkyl group may be cyclic, in which case the alkyl group may consist of three or four carbon atoms (i.e., C₃₋₄ cycloalkyl). The alkyl group may be saturated or unsaturated with one or more carbon-carbon double bonds and/or carbon-carbon triple bonds.

Some example compounds of formula (VIIIi) are provided in Table 8i below.

TABLE 8i

Example Compounds of Formula (VIIIi)

| Compound | R₂ | R₃ | R₄ | R₅ |
|---|---|---|---|---|
| 2298 | Me | Me | Me | —OMe |
| 2615 | Me | Me | Me | —OEt |
| 2616 | Me | Me | Me | —O-nPr |
| 2617 | Me | Me | Me | —O-iPr |
| 2618 | Me | Me | Me | —O-nBu |
| 2619 | Me | Me | Me | —O-iBu |
| 2620 | Me | Me | Me | —O-tBu |
| 2621 | Me | Me | Et | —OMe |
| 2622 | Me | Me | nPr | —OMe |
| 2623 | Me | Me | iPr | —OMe |
| 2624 | Me | Me | nBu | —OMe |
| 2625 | Me | Me | iBu | —OMe |
| 2626 | Me | Me | tBu | —OMe |
| 2627 | H | H | Me | —OMe |
| 2628 | H | H | Me | —OEt |
| 2629 | H | H | Me | —O-nPr |
| 2630 | H | H | Me | —O-iPr |
| 2631 | H | H | Me | —O-nBu |
| 2632 | H | H | Me | —O-iBu |
| 2633 | H | H | Me | —O-tBu |
| 2634 | H | H | Et | —OMe |
| 2635 | H | H | nPr | —OMe |
| 2636 | H | H | iPr | —OMe |
| 2637 | H | H | nBu | —OMe |
| 2638 | H | H | iBu | —OMe |
| 2639 | H | H | tBu | —OMe |
| 2640 | H | Me | Me | —OMe |
| 2641 | H | Me | Me | —OEt |
| 2642 | H | Me | Me | —O-nPr |
| 2643 | H | Me | Me | —O-iPr |
| 2644 | H | Me | Me | —O-nBu |
| 2645 | H | Me | Me | —O-iBu |
| 2646 | H | Me | Me | —O-tBu |
| 2647 | H | Me | Et | —OMe |
| 2648 | H | Me | nPr | —OMe |
| 2649 | H | Me | iPr | —OMe |
| 2650 | H | Me | nBu | —OMe |
| 2651 | H | Me | iBu | —OMe |
| 2652 | H | Me | tBu | —OMe |

Figure 16:
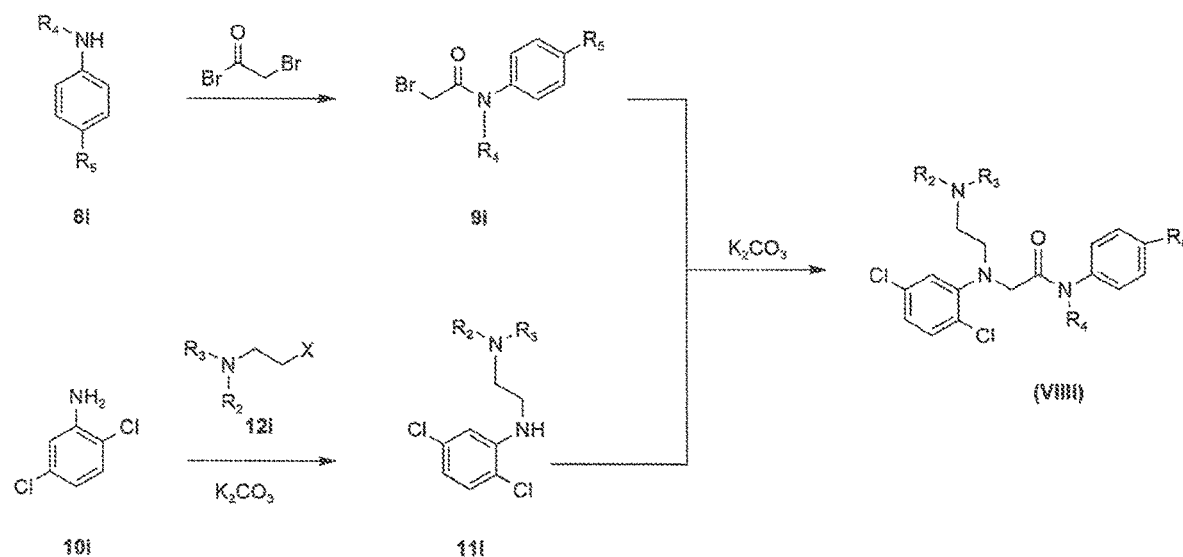
FIG. 16 shows a representative synthetic route for producing compounds of formula (VIIIi).

Referring now to FIG. 16, compounds consistent with formula (VIIIi) can be synthesized by, for example, acylating para-substituted anilines 8i with bromoacetyl bromide to form intermediates 9i. Intermediates 11i can be formed by alkylating 2,5-dichloroaniline 10i with β-haloamines 12i in the presence of base. Combining intermediates 11i with intermediates 9i in the presence of base yields compounds of formula (VIIIi).

In other embodiments, the present disclosure provides a compound of formula (VIIIj):

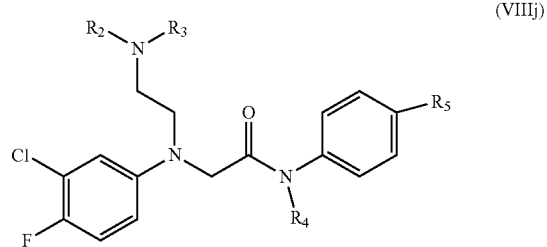

(VIIIj)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In compounds of formula (VIIIj), each R$_2$ and R$_3$ is independently H or methyl; in some embodiments both R$_2$ and R$_3$ are H. In other embodiments, both R$_2$ and R$_3$ are methyl. In some embodiments, one of R$_2$ and R$_3$ is H while the other is methyl.

R$_4$ is Alkyl; may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

R$_5$ is an O-Alkyl (i.e., alkoxy) at the para position. The alkyl group may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

Some example compounds of formula (VIIIj) are provided in Table 8j below.

TABLE 8j

Example Compounds of Formula (VIIIj)

| Compound | R$_2$ | R$_3$ | R$_4$ | R$_5$ |
| --- | --- | --- | --- | --- |
| 2299 | Me | Me | Me | —OMe |
| 2654 | Me | Me | Me | —OEt |
| 2655 | Me | Me | Me | —O-nPr |
| 2656 | Me | Me | Me | —O-iPr |
| 2657 | Me | Me | Me | —O-nBu |
| 2658 | Me | Me | Me | —O-iBu |
| 2659 | Me | Me | Me | —O-tBu |
| 2660 | Me | Me | Et | —OMe |
| 2661 | Me | Me | nPr | —OMe |
| 2662 | Me | Me | iPr | —OMe |
| 2663 | Me | Me | nBu | —OMe |
| 2664 | Me | Me | iBu | —OMe |
| 2665 | Me | Me | tBu | —OMe |
| 2666 | H | H | Me | —OMe |
| 2667 | H | H | Me | —OEt |
| 2668 | H | H | Me | —O-nPr |
| 2669 | H | H | Me | —O-iPr |
| 2670 | H | H | Me | —O-nBu |
| 2671 | H | H | Me | —O-iBu |
| 2672 | H | H | Me | —O-tBu |
| 2673 | H | H | Et | —OMe |
| 2674 | H | H | nPr | —OMe |
| 2675 | H | H | iPr | —OMe |
| 2676 | H | H | nBu | —OMe |
| 2677 | H | H | iBu | —OMe |
| 2678 | H | H | tBu | —OMe |
| 2679 | H | Me | Me | —OMe |
| 2680 | H | Me | Me | —OEt |
| 2681 | H | Me | Me | —O-nPr |
| 2682 | H | Me | Me | —O-iPr |
| 2683 | H | Me | Me | —O-nBu |
| 2684 | H | Me | Me | —O-iBu |
| 2685 | H | Me | Me | —O-tBu |
| 2686 | H | Me | Et | —OMe |
| 2687 | H | Me | nPr | —OMe |
| 2688 | H | Me | iPr | —OMe |
| 2689 | H | Me | nBu | —OMe |
| 2690 | H | Me | iBu | —OMe |
| 2691 | H | Me | tBu | —OMe |

Figure 17:
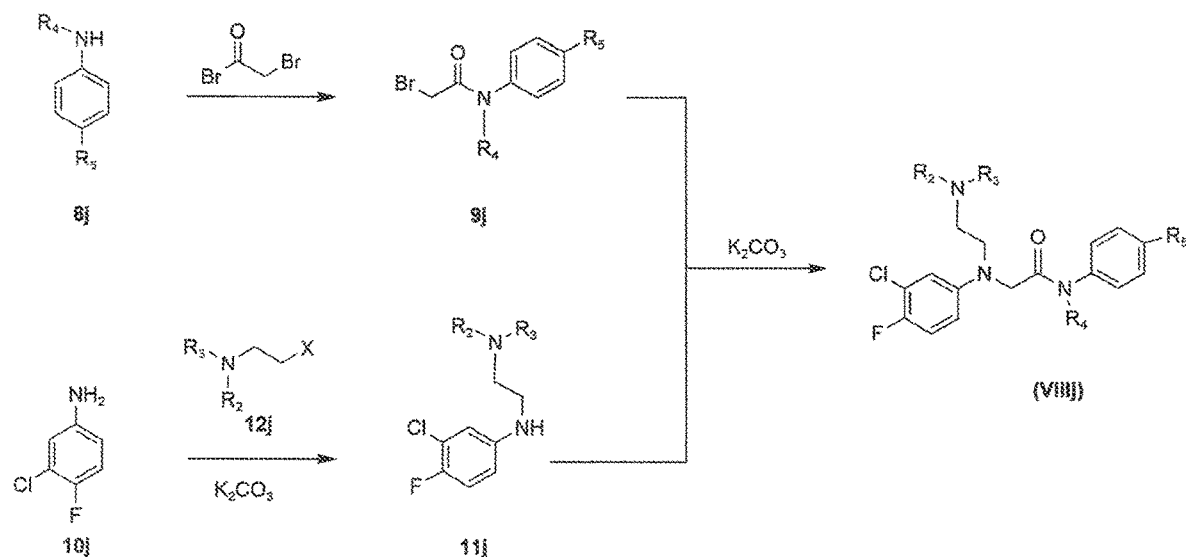
FIG. 17 shows a representative synthetic route for producing compounds of formula (VIIIj).

Referring now to FIG. 17, compounds consistent with formula (VIIIj) can be synthesized by, for example, acylating para-substituted anilines 8j with bromoacetyl bromide to form intermediates 9j. Intermediates 11j can be formed by alkylating 3-chloro-4-fluoroaniline 10j with β-haloamines 12j in the presence of base. Combining intermediates 11j with intermediates 9j in the presence of base yields compounds of formula (VIIIj).

In other embodiments, the present disclosure provides a compound of formula (VIIIk):

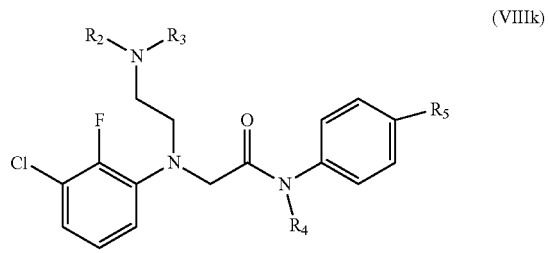

(VIIIk)

wherein:
R$_2$=H or Me;
R$_3$=H or Me;
R$_4$=Alkyl;
R$_5$=O-Alkyl; and
Alkyl=aliphatic C$_1$-C$_4$ alkyl.

In compounds of formula (VIIIk), each R$_2$ and R$_3$ is independently H or methyl; in some embodiments both R$_2$ and R$_3$ are H. In other embodiments, both R$_2$ and R$_3$ are methyl. In some embodiments, one of R$_2$ and R$_3$ is H while the other is methyl.

R$_4$ is Alkyl; may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

R$_5$ is an O-Alkyl (i.e., alkoxy) at the para position. The alkyl group may be linear or branched, and may consist of one to four carbon atoms (i.e., C$_{1-4}$ alkyl). The alkyl group may be cyclic, in which case the alkyl group may consist of three or four carbon atoms (i.e., C$_{3-4}$ cycloalkyl). The alkyl group may be saturated or unsaturated with one or more carbon-carbon double bonds and/or carbon-carbon triple bonds.

Some example compounds of formula (VIIIk) are provided in Table 8k below.

TABLE 8k

Example Compounds of Formula (VIIIk)

| Compound | R$_2$ | R$_3$ | R$_4$ | R$_5$ |
| --- | --- | --- | --- | --- |
| 2300 | Me | Me | Me | —OMe |
| 2693 | Me | Me | Me | —OEt |
| 2694 | Me | Me | Me | —O-nPr |
| 2695 | Me | Me | Me | —O-iPr |
| 2696 | Me | Me | Me | —O-nBu |
| 2697 | Me | Me | Me | —O-iBu |
| 2698 | Me | Me | Me | —O-tBu |
| 2699 | Me | Me | Et | —OMe |
| 2700 | Me | Me | nPr | —OMe |
| 2701 | Me | Me | iPr | —OMe |
| 2702 | Me | Me | nBu | —OMe |

TABLE 8k-continued

Example Compounds of Formula (VIIIk)

| Compound | R₂ | R₃ | R₄ | R₅ |
|---|---|---|---|---|
| 2703 | Me | Me | iBu | —OMe |
| 2704 | Me | Me | tBu | —OMe |
| 2705 | H | H | Me | —OMe |
| 2706 | H | H | Me | —OEt |
| 2707 | H | H | Me | —O-nPr |
| 2708 | H | H | Me | —O-iPr |
| 2709 | H | H | Me | —O-nBu |
| 2710 | H | H | Me | —O-iBu |
| 2711 | H | H | Me | —O-tBu |
| 2712 | H | H | Et | —OMe |
| 2713 | H | H | nPr | —OMe |
| 2714 | H | H | iPr | —OMe |
| 2715 | H | H | nBu | —OMe |
| 2716 | H | H | iBu | —OMe |
| 2717 | H | H | tBu | —OMe |
| 2718 | H | Me | Me | —OMe |
| 2719 | H | Me | Me | —OEt |
| 2720 | H | Me | Me | —O-nPr |
| 2721 | H | Me | Me | —O-iPr |
| 2722 | H | Me | Me | —O-nBu |
| 2723 | H | Me | Me | —O-iBu |
| 2724 | H | Me | Me | —O-tBu |
| 2725 | H | Me | Et | —OMe |
| 2726 | H | Me | nPr | —OMe |
| 2727 | H | Me | iPr | —OMe |
| 2728 | H | Me | nBu | —OMe |
| 2729 | H | Me | iBu | —OMe |
| 2730 | H | Me | tBu | —OMe |

Figure 18:
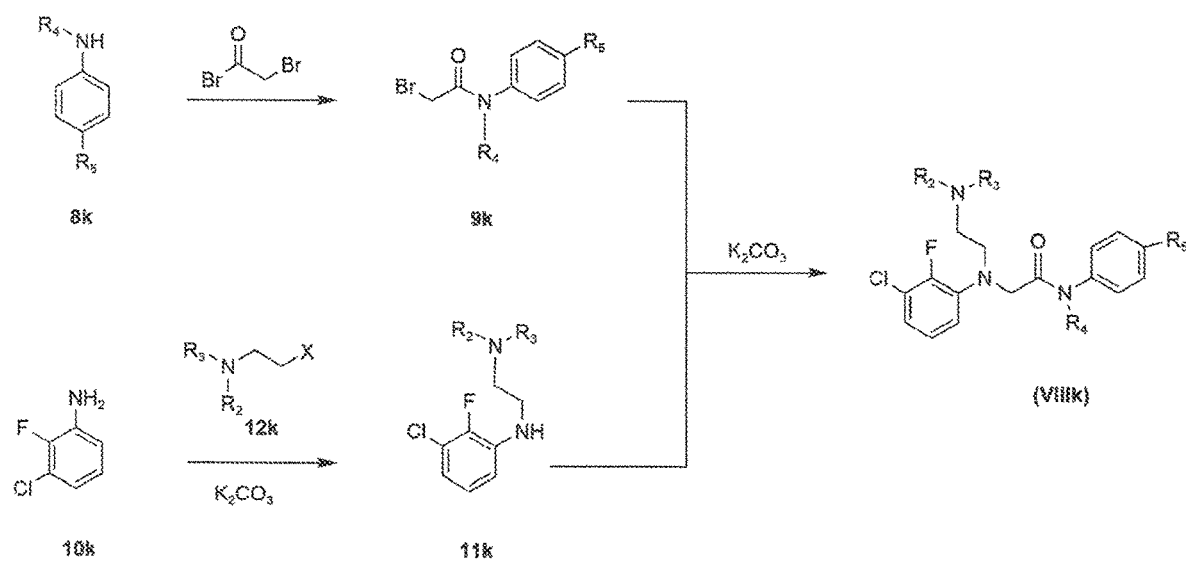
FIG. 18 shows a representative synthetic route for producing compounds of formula (VIIIk).

Referring now to FIG. 18, compounds consistent with formula (VIIIk) can be synthesized by, for example, acylating para-substituted anilines 8k with bromoacetyl bromide to form intermediates 9k. Intermediates 11k can be formed by alkylating 2-fluoro-3-chloroaniline 10k with β-haloamines 12k in the presence of base. Combining intermediates 11k with intermediates 9k in the presence of base yields compounds of formula (VIIIk).

In other embodiments, the present disclosure provides a compound of formula (VIIIm):

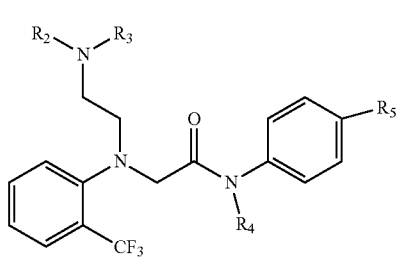

(VIIIm)

wherein:
$R_2$=H or Me;
$R_3$=H or Me;
$R_4$=Alkyl;
$R_5$=O-Alkyl; and
Alkyl=aliphatic $C_1$-$C_4$ alkyl.

In compounds of formula (VIIIm), each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

Some example compounds of formula (VIIIm) are provided in Table 8m below.

TABLE 8m

Example Compounds of Formula (VIIIm)

| Compound | R₂ | R₃ | R₄ | R₅ |
|---|---|---|---|---|
| 2301 | Me | Me | Me | —OMe |
| 2732 | Me | Me | Me | —OEt |
| 2733 | Me | Me | Me | —O-nPr |
| 2734 | Me | Me | Me | —O-iPr |
| 2735 | Me | Me | Me | —O-nBu |
| 2736 | Me | Me | Me | —O-iBu |
| 2737 | Me | Me | Me | —O-tBu |
| 2738 | Me | Me | Et | —OMe |
| 2739 | Me | Me | nPr | —OMe |
| 2740 | Me | Me | iPr | —OMe |
| 2741 | Me | Me | nBu | —OMe |
| 2742 | Me | Me | iBu | —OMe |
| 2743 | Me | Me | tBu | —OMe |
| 2744 | H | H | Me | —OMe |
| 2745 | H | H | Me | —OEt |
| 2746 | H | H | Me | —O-nPr |
| 2747 | H | H | Me | —O-iPr |
| 2748 | H | H | Me | —O-nBu |
| 2749 | H | H | Me | —O-iBu |
| 2750 | H | H | Me | —O-tBu |
| 2751 | H | H | Et | —OMe |
| 2752 | H | H | nPr | —OMe |
| 2753 | H | H | iPr | —OMe |
| 2754 | H | H | nBu | —OMe |
| 2755 | H | H | iBu | —OMe |
| 2756 | H | H | tBu | —OMe |
| 2757 | H | Me | Me | —OMe |
| 2758 | H | Me | Me | —OEt |
| 2759 | H | Me | Me | —O-nPr |
| 2760 | H | Me | Me | —O-iPr |
| 2761 | H | Me | Me | —O-nBu |
| 2762 | H | Me | Me | —O-iBu |
| 2763 | H | Me | Me | —O-tBu |
| 2764 | H | Me | Et | —OMe |
| 2765 | H | Me | nPr | —OMe |
| 2766 | H | Me | iPr | —OMe |
| 2767 | H | Me | nBu | —OMe |
| 2768 | H | Me | iBu | —OMe |
| 2769 | H | Me | tBu | —OMe |

Figure 19:
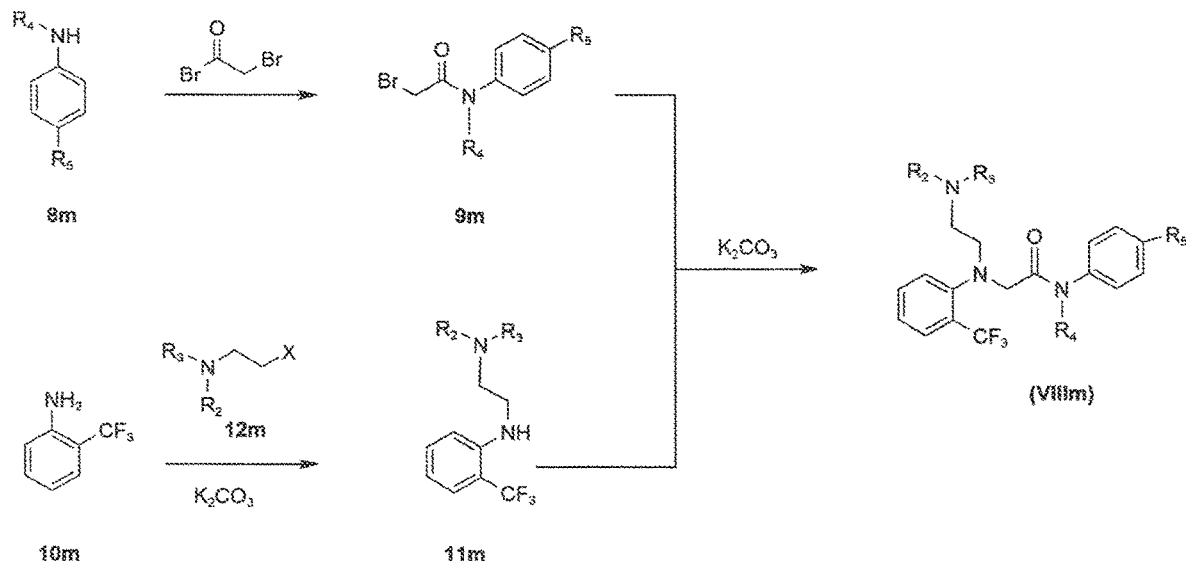
FIG. 19 shows a representative synthetic route for producing compounds of formula (VIIIm).

Referring now to FIG. 19, compounds consistent with formula (VIIIm) can be synthesized by, for example, acylating para-substituted anilines 8m with bromoacetyl bromide to form intermediates 9m. Intermediates 11m can be formed by alkylating o-trifluoromethylaniline 10m with β-haloamines 12m in the presence of base. Combining intermediates 11m with intermediates 9m in the presence of base yields compounds of formula (VIIIm).

In other embodiments, the present disclosure provides a compound of formula (VIIIn):

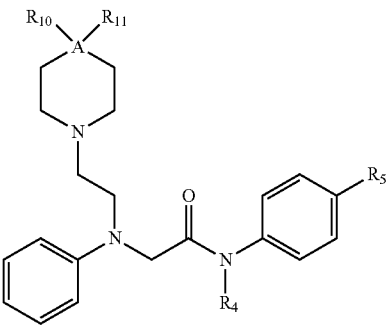

(VIIIn)

wherein:
A=C or N;
$R_2$=H or Me;
$R_3$=H or Me;
$R_4$=Alkyl;
$R_5$=O-Alkyl;
when A=C, then $R_{10}$=$R_{11}$=H; or when A=N, then $R_{10}$=Alkyl and $R_{11}$=null; and
Alkyl=aliphatic $C_1$-$C_4$ alkyl.

In compounds of formula (VIIIn), A is selected from the group consisting of carbon and nitrogen.

Each $R_2$ and $R_3$ is independently H or methyl; in some embodiments both $R_2$ and $R_3$ are H. In other embodiments, both $R_2$ and $R_3$ are methyl. In some embodiments, one of $R_2$ and $R_3$ is H while the other is methyl.

$R_4$ is Alkyl; may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

$R_5$ is an O-Alkyl (i.e., alkoxy) at the para position. The alkyl group may be linear or branched, and may consist of one to four carbon atoms (i.e., $C_{1-4}$ alkyl). The alkyl group may be cyclic, in which case the alkyl group may consist of three or four carbon atoms (i.e., $C_{3-4}$ cycloalkyl). The alkyl group may be saturated or unsaturated with one or more carbon-carbon double bonds and/or carbon-carbon triple bonds.

When A is carbon, then $R_{10}$ and $R_{11}$ are both hydrogen. When A is nitrogen, then $R_{10}$ is Alkyl and $R_{11}$ is no atom (null).

Some example compounds of formula (VIIIn) are provided in Table 8n below.

TABLE 8n

Example Compounds of Formula (VIIIn)

| Compound | $R_4$ | $R_5$ | A | $R_{10}$ | $R_{11}$ |
|---|---|---|---|---|---|
| 2303 | Me | —OMe | C | H | H |
| 2771 | Me | —OEt | C | H | H |
| 2772 | Me | —O-nPr | C | H | H |
| 2773 | Me | —O-iPr | C | H | H |
| 2774 | Me | —O-nBu | C | H | H |
| 2775 | Me | —O-iBu | C | H | H |
| 2776 | Me | —O-tBu | C | H | H |
| 2777 | Et | —OMe | C | H | H |
| 2778 | nPr | —OMe | C | H | H |
| 2779 | iPr | —OMe | C | H | H |
| 2780 | nBu | —OMe | C | H | H |
| 2781 | iBu | —OMe | C | H | H |
| 2782 | tBu | —OMe | C | H | H |
| 2783 | Me | —OMe | C | H | H |
| 2784 | Me | —OEt | C | H | H |
| 2785 | Me | —O-nPr | C | H | H |
| 2786 | Me | —O-iPr | C | H | H |
| 2787 | Me | —O-nBu | C | H | H |
| 2788 | Me | —O-iBu | C | H | H |
| 2789 | Me | —O-tBu | C | H | H |
| 2790 | Et | —OMe | C | H | H |
| 2791 | nPr | —OMe | C | H | H |
| 2792 | iPr | —OMe | C | H | H |
| 2793 | nBu | —OMe | C | H | H |
| 2794 | iBu | —OMe | C | H | H |
| 2795 | tBu | —OMe | C | H | H |
| 2796 | Me | —OMe | C | H | H |
| 2797 | Me | —OEt | C | H | H |
| 2798 | Me | —O-nPr | C | H | H |
| 2799 | Me | —O-iPr | C | H | H |
| 2800 | Me | —O-nBu | C | H | H |
| 2801 | Me | —O-iBu | C | H | H |
| 2802 | Me | —O-tBu | C | H | H |
| 2803 | Et | —OMe | C | H | H |
| 2804 | nPr | —OMe | C | H | H |
| 2805 | iPr | —OMe | C | H | H |
| 2806 | nBu | —OMe | C | H | H |
| 2807 | iBu | —OMe | C | H | H |
| 2808 | tBu | —OMe | C | H | H |
| 2304 | Me | —OMe | N | Me | null |
| 2810 | Me | —OEt | N | Me | null |
| 2811 | Me | —O-nPr | N | Me | null |
| 2812 | Me | —O-iPr | N | Me | null |
| 2813 | Me | —O-nBu | N | Me | null |
| 2814 | Me | —O-iBu | N | Me | null |
| 2815 | Me | —O-tBu | N | Me | null |
| 2816 | Et | —OMe | N | Me | null |
| 2817 | nPr | —OMe | N | Me | null |
| 2818 | iPr | —OMe | N | Me | null |
| 2819 | nBu | —OMe | N | Me | null |
| 2820 | iBu | —OMe | N | Me | null |
| 2821 | tBu | —OMe | N | Me | null |
| 2822 | Me | —OMe | N | Me | null |
| 2823 | Me | —OEt | N | Me | null |
| 2824 | Me | —O-nPr | N | Me | null |
| 2825 | Me | —O-iPr | N | Me | null |
| 2826 | Me | —O-nBu | N | Me | null |
| 2827 | Me | —O-iBu | N | Me | null |
| 2828 | Me | —O-tBu | N | Me | null |
| 2829 | Et | —OMe | N | Me | null |
| 2830 | nPr | —OMe | N | Me | null |
| 2831 | iPr | —OMe | N | Me | null |
| 2832 | nBu | —OMe | N | Me | null |
| 2833 | iBu | —OMe | N | Me | null |
| 2834 | tBu | —OMe | N | Me | null |
| 2835 | Me | —OMe | N | Me | null |
| 2836 | Me | —OEt | N | Me | null |
| 2837 | Me | —O-nPr | N | Me | null |
| 2838 | Me | —O-iPr | N | Me | null |
| 2839 | Me | —O-nBu | N | Me | null |
| 2840 | Me | —O-iBu | N | Me | null |
| 2841 | Me | —O-tBu | N | Me | null |
| 2842 | Et | —OMe | N | Me | null |
| 2843 | nPr | —OMe | N | Me | null |
| 2844 | iPr | —OMe | N | Me | null |
| 2845 | nBu | —OMe | N | Me | null |
| 2846 | iBu | —OMe | N | Me | null |
| 2847 | tBu | —OMe | N | Me | null |
| 2848 | Me | —OMe | N | Et | null |
| 2849 | Me | —OEt | N | Et | null |
| 2850 | Me | —O-nPr | N | Et | null |
| 2851 | Me | —O-iPr | N | Et | null |
| 2852 | Me | —O-nBu | N | Et | null |
| 2853 | Me | —O-iBu | N | Et | null |
| 2854 | Me | —O-tBu | N | Et | null |
| 2855 | Et | —OMe | N | Et | null |
| 2856 | nPr | —OMe | N | Et | null |
| 2857 | iPr | —OMe | N | Et | null |

TABLE 8n-continued

Example Compounds of Formula (VIIIn)

| Compound | $R_4$ | $R_5$ | A | $R_{10}$ | $R_{11}$ |
|---|---|---|---|---|---|
| 2858 | nBu | —OMe | N | Et | null |
| 2859 | iBu | —OMe | N | Et | null |
| 2860 | tBu | —OMe | N | Et | null |
| 2861 | Me | —OMe | N | Et | null |
| 2862 | Me | —OEt | N | Et | null |
| 2863 | Me | —O-nPr | N | Et | null |
| 2864 | Me | —O-iPr | N | Et | null |
| 2865 | Me | —O-nBu | N | Et | null |
| 2866 | Me | —O-iBu | N | Et | null |
| 2867 | Me | —O-tBu | N | Et | null |
| 2868 | Et | —OMe | N | Et | null |
| 2869 | nPr | —OMe | N | Et | null |
| 2870 | iPr | —OMe | N | Et | null |
| 2871 | nBu | —OMe | N | Et | null |
| 2872 | iBu | —OMe | N | Et | null |
| 2873 | tBu | —OMe | N | Et | null |
| 2874 | Me | —OMe | N | Et | null |
| 2875 | Me | —OEt | N | Et | null |
| 2876 | Me | —O-nPr | N | Et | null |
| 2877 | Me | —O-iPr | N | Et | null |
| 2878 | Me | —O-nBu | N | Et | null |
| 2879 | Me | —O-iBu | N | Et | null |
| 2880 | Me | —O-tBu | N | Et | null |
| 2881 | Et | —OMe | N | Et | null |
| 2882 | nPr | —OMe | N | Et | null |
| 2883 | iPr | —OMe | N | Et | null |
| 2884 | nBu | —OMe | N | Et | null |
| 2885 | iBu | —OMe | N | Et | null |
| 2886 | tBu | —OMe | N | Et | null |
| 2887 | Me | —OMe | N | nPr | null |
| 2888 | Me | —OEt | N | nPr | null |
| 2889 | Me | —O-nPr | N | nPr | null |
| 2890 | Me | —O-iPr | N | nPr | null |
| 2891 | Me | —O-nBu | N | nPr | null |
| 2892 | Me | —O-iBu | N | nPr | null |
| 2893 | Me | —O-tBu | N | nPr | null |
| 2894 | Et | —OMe | N | nPr | null |
| 2895 | nPr | —OMe | N | nPr | null |
| 2896 | iPr | —OMe | N | nPr | null |
| 2897 | nBu | —OMe | N | nPr | null |
| 2898 | iBu | —OMe | N | nPr | null |
| 2899 | tBu | —OMe | N | nPr | null |
| 2900 | Me | —OMe | N | nPr | null |
| 2901 | Me | —OEt | N | nPr | null |
| 2902 | Me | —O-nPr | N | nPr | null |
| 2903 | Me | —O-iPr | N | nPr | null |
| 2904 | Me | —O-nBu | N | nPr | null |
| 2905 | Me | —O-iBu | N | nPr | null |
| 2906 | Me | —O-tBu | N | nPr | null |
| 2907 | Et | —OMe | N | nPr | null |
| 2908 | nPr | —OMe | N | nPr | null |
| 2909 | iPr | —OMe | N | nPr | null |
| 2910 | nBu | —OMe | N | nPr | null |
| 2911 | iBu | —OMe | N | nPr | null |
| 2912 | tBu | —OMe | N | nPr | null |
| 2913 | Me | —OMe | N | nPr | null |
| 2914 | Me | —OEt | N | nPr | null |
| 2915 | Me | —O-nPr | N | nPr | null |
| 2916 | Me | —O-iPr | N | nPr | null |
| 2917 | Me | —O-nBu | N | nPr | null |
| 2918 | Me | —O-iBu | N | nPr | null |
| 2919 | Me | —O-tBu | N | nPr | null |
| 2920 | Et | —OMe | N | nPr | null |
| 2921 | nPr | —OMe | N | nPr | null |
| 2922 | iPr | —OMe | N | nPr | null |
| 2923 | nBu | —OMe | N | nPr | null |
| 2924 | iBu | —OMe | N | nPr | null |
| 2925 | tBu | —OMe | N | nPr | null |
| 2926 | Me | —OMe | N | iPr | null |
| 2927 | Me | —OEt | N | iPr | null |
| 2928 | Me | —O-nPr | N | iPr | null |
| 2929 | Me | —O-iPr | N | iPr | null |
| 2930 | Me | —O-nBu | N | iPr | null |
| 2931 | Me | —O-iBu | N | iPr | null |
| 2932 | Me | —O-tBu | N | iPr | null |
| 2933 | Et | —OMe | N | iPr | null |
| 2934 | nPr | —OMe | N | iPr | null |
| 2935 | iPr | —OMe | N | iPr | null |
| 2936 | nBu | —OMe | N | iPr | null |
| 2937 | iBu | —OMe | N | iPr | null |
| 2938 | tBu | —OMe | N | iPr | null |
| 2939 | Me | —OMe | N | iPr | null |
| 2940 | Me | —OEt | N | iPr | null |
| 2941 | Me | —O-nPr | N | iPr | null |
| 2942 | Me | —O-iPr | N | iPr | null |
| 2943 | Me | —O-nBu | N | iPr | null |
| 2944 | Me | —O-iBu | N | iPr | null |
| 2945 | Me | —O-tBu | N | iPr | null |
| 2946 | Et | —OMe | N | iPr | null |
| 2947 | nPr | —OMe | N | iPr | null |
| 2948 | iPr | —OMe | N | iPr | null |
| 2949 | nBu | —OMe | N | iPr | null |
| 2950 | iBu | —OMe | N | iPr | null |
| 2951 | tBu | —OMe | N | iPr | null |
| 2952 | Me | —OMe | N | iPr | null |
| 2953 | Me | —OEt | N | iPr | null |
| 2954 | Me | —O-nPr | N | iPr | null |
| 2955 | Me | —O-iPr | N | iPr | null |
| 2956 | Me | —O-nBu | N | iPr | null |
| 2957 | Me | —O-iBu | N | iPr | null |
| 2958 | Me | —O-tBu | N | iPr | null |
| 2959 | Et | —OMe | N | iPr | null |
| 2960 | nPr | —OMe | N | iPr | null |
| 2961 | iPr | —OMe | N | iPr | null |
| 2962 | nBu | —OMe | N | iPr | null |
| 2963 | iBu | —OMe | N | iPr | null |
| 2964 | tBu | —OMe | N | iPr | null |
| 2965 | Me | —OMe | N | nBu | null |
| 2966 | Me | —OEt | N | nBu | null |
| 2967 | Me | —O-nPr | N | nBu | null |
| 2968 | Me | —O-iPr | N | nBu | null |
| 2969 | Me | —O-nBu | N | nBu | null |
| 2970 | Me | —O-iBu | N | nBu | null |
| 2971 | Me | —O-tBu | N | nBu | null |
| 2972 | Et | —OMe | N | nBu | null |
| 2973 | nPr | —OMe | N | nBu | null |
| 2974 | iPr | —OMe | N | nBu | null |
| 2975 | nBu | —OMe | N | nBu | null |
| 2976 | iBu | —OMe | N | nBu | null |
| 2977 | tBu | —OMe | N | nBu | null |
| 2978 | Me | —OMe | N | nBu | null |
| 2979 | Me | —OEt | N | nBu | null |
| 2980 | Me | —O-nPr | N | nBu | null |
| 2981 | Me | —O-iPr | N | nBu | null |
| 2982 | Me | —O-nBu | N | nBu | null |
| 2983 | Me | —O-iBu | N | nBu | null |
| 2984 | Me | —O-tBu | N | nBu | null |
| 2985 | Et | —OMe | N | nBu | null |
| 2986 | nPr | —OMe | N | nBu | null |
| 2987 | iPr | —OMe | N | nBu | null |
| 2988 | nBu | —OMe | N | nBu | null |
| 2989 | iBu | —OMe | N | nBu | null |
| 2990 | tBu | —OMe | N | nBu | null |
| 2991 | Me | —OMe | N | nBu | null |
| 2992 | Me | —OEt | N | nBu | null |
| 2993 | Me | —O-nPr | N | nBu | null |
| 2994 | Me | —O-iPr | N | nBu | null |
| 2995 | Me | —O-nBu | N | nBu | null |
| 2996 | Me | —O-iBu | N | nBu | null |
| 2997 | Me | —O-tBu | N | nBu | null |
| 2998 | Et | —OMe | N | nBu | null |
| 2999 | nPr | —OMe | N | nBu | null |
| 3000 | iPr | —OMe | N | nBu | null |
| 3001 | nBu | —OMe | N | nBu | null |
| 3002 | iBu | —OMe | N | nBu | null |
| 3003 | tBu | —OMe | N | nBu | null |
| 3004 | Me | —OMe | N | iBu | null |
| 3005 | Me | —OEt | N | iBu | null |
| 3006 | Me | —O-nPr | N | iBu | null |
| 3007 | Me | —O-iPr | N | iBu | null |
| 3008 | Me | —O-nBu | N | iBu | null |
| 3009 | Me | —O-iBu | N | iBu | null |

TABLE 8n-continued

Example Compounds of Formula (VIIIn)

| Compound | R$_4$ | R$_5$ | A | R$_{10}$ | R$_{11}$ |
|---|---|---|---|---|---|
| 3010 | Me | —O-tBu | N | iBu | null |
| 3011 | Et | —OMe | N | iBu | null |
| 3012 | nPr | —OMe | N | iBu | null |
| 3013 | iPr | —OMe | N | iBu | null |
| 3014 | nBu | —OMe | N | iBu | null |
| 3015 | iBu | —OMe | N | iBu | null |
| 3016 | tBu | —OMe | N | iBu | null |
| 3017 | Me | —OMe | N | iBu | null |
| 3018 | Me | —OEt | N | iBu | null |
| 3019 | Me | —O-nPr | N | iBu | null |
| 3020 | Me | —O-iPr | N | iBu | null |
| 3021 | Me | —O-nBu | N | iBu | null |
| 3022 | Me | —O-iBu | N | iBu | null |
| 3023 | Me | —O-tBu | N | iBu | null |
| 3024 | Et | —OMe | N | iBu | null |
| 3025 | nPr | —OMe | N | iBu | null |
| 3026 | iPr | —OMe | N | iBu | null |
| 3027 | nBu | —OMe | N | iBu | null |
| 3028 | iBu | —OMe | N | iBu | null |
| 3029 | tBu | —OMe | N | iBu | null |
| 3030 | Me | —OMe | N | iBu | null |
| 3031 | Me | —OEt | N | iBu | null |
| 3032 | Me | —O-nPr | N | iBu | null |
| 3033 | Me | —O-iPr | N | iBu | null |
| 3034 | Me | —O-nBu | N | iBu | null |
| 3035 | Me | —O-iBu | N | iBu | null |
| 3036 | Me | —O-tBu | N | iBu | null |
| 3037 | Et | —OMe | N | iBu | null |
| 3038 | nPr | —OMe | N | iBu | null |
| 3039 | iPr | —OMe | N | iBu | null |
| 3040 | nBu | —OMe | N | iBu | null |
| 3041 | iBu | —OMe | N | iBu | null |
| 3042 | tBu | —OMe | N | iBu | null |
| 3043 | Me | —OMe | N | tBu | null |
| 3044 | Me | —OEt | N | tBu | null |
| 3045 | Me | —O-nPr | N | tBu | null |
| 3046 | Me | —O-iPr | N | tBu | null |
| 3047 | Me | —O-nBu | N | tBu | null |
| 3048 | Me | —O-iBu | N | tBu | null |
| 3049 | Me | —O-tBu | N | tBu | null |
| 3050 | Et | —OMe | N | tBu | null |
| 3051 | nPr | —OMe | N | tBu | null |
| 3052 | iPr | —OMe | N | tBu | null |
| 3053 | nBu | —OMe | N | tBu | null |
| 3054 | iBu | —OMe | N | tBu | null |
| 3055 | tBu | —OMe | N | tBu | null |
| 3056 | Me | —OMe | N | tBu | null |
| 3057 | Me | —OEt | N | tBu | null |
| 3058 | Me | —O-nPr | N | tBu | null |
| 3059 | Me | —O-iPr | N | tBu | null |
| 3060 | Me | —O-nBu | N | tBu | null |
| 3061 | Me | —O-iBu | N | tBu | null |
| 3062 | Me | —O-tBu | N | tBu | null |
| 3063 | Et | —OMe | N | tBu | null |
| 3064 | nPr | —OMe | N | tBu | null |
| 3065 | iPr | —OMe | N | tBu | null |
| 3066 | nBu | —OMe | N | tBu | null |
| 3067 | iBu | —OMe | N | tBu | null |
| 3068 | tBu | —OMe | N | tBu | null |
| 3069 | Me | —OMe | N | tBu | null |
| 3070 | Me | —OEt | N | tBu | null |
| 3071 | Me | —O-nPr | N | tBu | null |
| 3072 | Me | —O-iPr | N | tBu | null |
| 3073 | Me | —O-nBu | N | tBu | null |
| 3074 | Me | —O-iBu | N | tBu | null |
| 3075 | Me | —O-tBu | N | tBu | null |
| 3076 | Et | —OMe | N | tBu | null |
| 3077 | nPr | —OMe | N | tBu | null |
| 3078 | iPr | —OMe | N | tBu | null |
| 3079 | nBu | —OMe | N | tBu | null |
| 3080 | iBu | —OMe | N | tBu | null |
| 3081 | tBu | —OMe | N | tBu | null |

Figure 20:
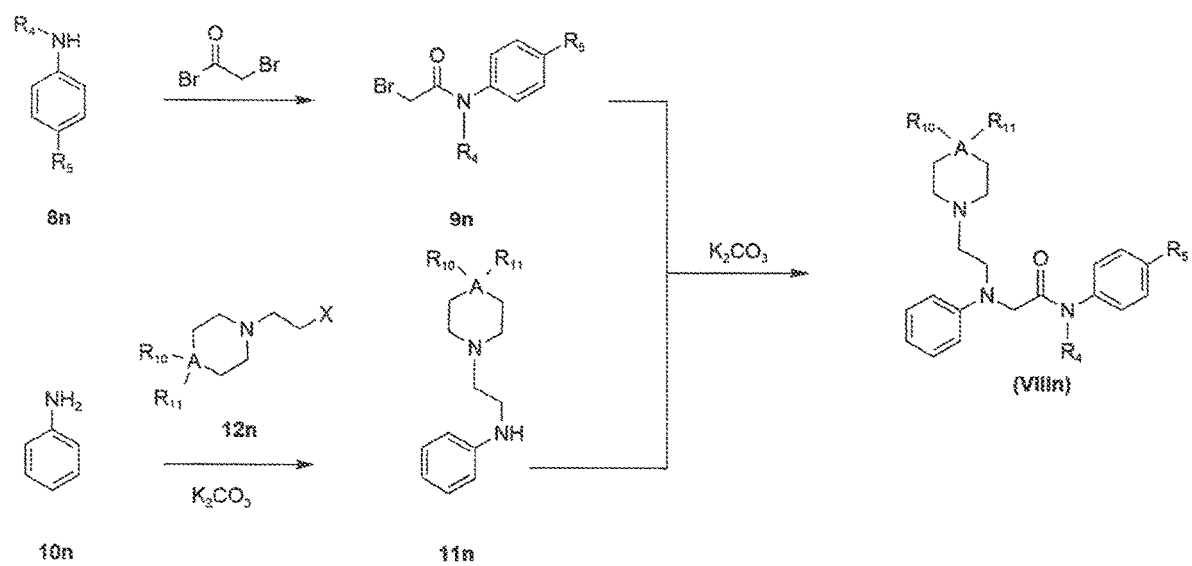
FIG. 20 shows a representative synthetic route for producing compounds of formula (VIIIn).

Referring now to FIG. 20, compounds consistent with formula (VIIIn) can be synthesized by, for example, acylating para-substituted anilines 8n with bromoacetyl bromide to form intermediates 9n. Intermediates 11n can be formed by alkylating aniline 10n with β-halogenated cycloamines 12n in the presence of base. Combining intermediates 11n with intermediates 9n in the presence of base yields compounds of formula (VIIIn).

In other embodiments, the present disclosure provides a compound of formula (IX):

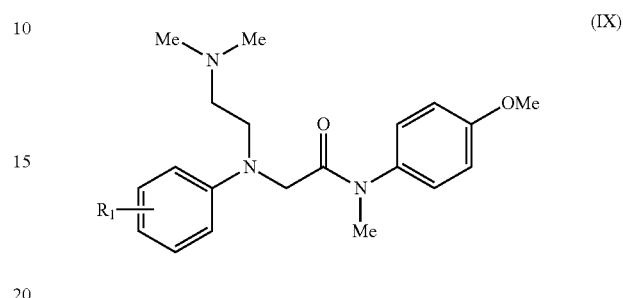

(IX)

wherein R$_1$ is selected from the group consisting of: H, m-chloro; 3,4-dichloro; o-methoxy; β-methoxy; o-methyl; m-trifluoromethoxy; m-trifluoromethyl-β-chloro; 2,5-dichloro; 3-chloro-4-fluoro; 2-fluoro-3-chloro; and o-trifluoromethyl.

Some example compounds of formula (IX) are provided in Table 9 below.

TABLE 9

Example Compounds of Formula (IX)

| Compound | R$_1$ |
|---|---|
| 2290 | H |
| 2291 | m-chloro |
| 2292 | 3,4-dichloro |
| 2293 | o-methoxy |
| 2294 | p-methoxy |
| 2295 | o-methyl |
| 2296 | m-trifluoromethoxy |
| 2297 | m-trifluoromethyl-p-chloro |
| 2298 | 2,5-dichloro |
| 2299 | 3-chloro-4-fluoro |
| 2300 | 2-fluoro-3-chloro |
| 2301 | o-trifluoromethyl |

Figure 21:
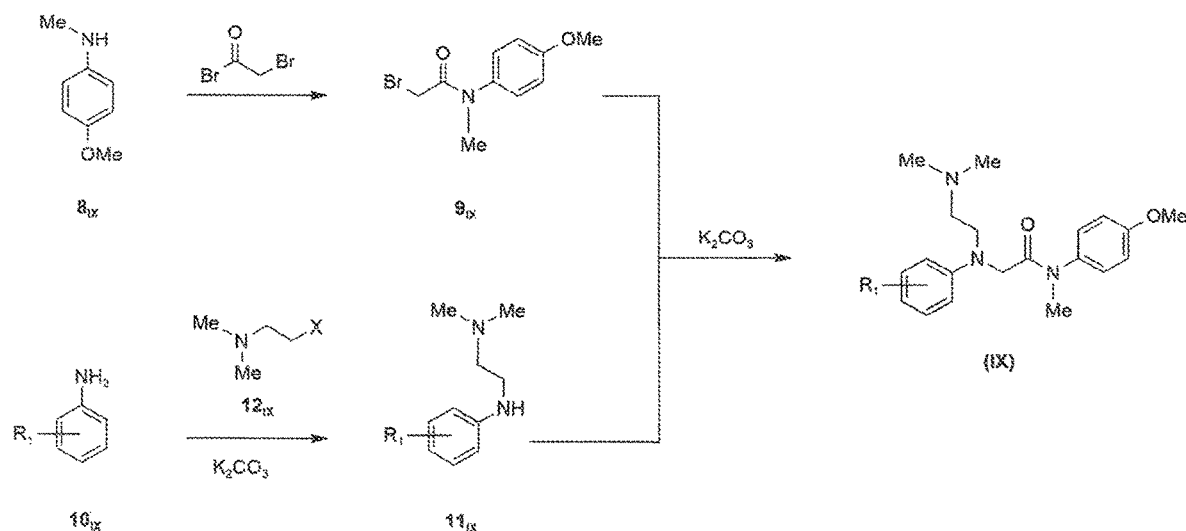
FIG. 21 shows a representative synthetic route for producing compounds of formula (IX).

Referring now to FIG. 21, compounds consistent with formula (IX) can be synthesized by, for example, acylating para-methoxy-N-methylaniline 8$_{IX}$ with bromoacetyl bromide to form intermediate N-bromoacetyl-N-methyl-β-methoxyaniline 9$_{IX}$. Intermediates 11$_{IX}$ can be formed by alkylating R$_1$-substituted anilines 10$_{IX}$ with β-halo-N,N,-dimethylamines 12$_{IX}$ in the presence of base. Combining intermediates 11$_{IX}$ with intermediates 9$_{IX}$ in the presence of base yields compounds of formula (IX).

In other embodiments, the present disclosure provides a compound of formula (X):

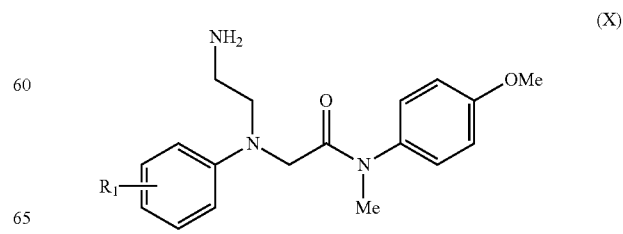

(X)

wherein $R_1$ is selected from the group consisting of: H, m-chloro; 3,4-dichloro; o-methoxy; β-methoxy; o-methyl; m-trifluoromethoxy; m-trifluoromethyl-β-chloro; 2,5-dichloro; 3-chloro-4-fluoro; 2-fluoro-3-chloro; and o-trifluoromethyl.

Some example compounds of formula (X) are provided in Table 10 below.

TABLE 10

Example Compounds of Formula (X)

| Compound | $R_1$ |
|---|---|
| 2302 | H |
| 3094 | m-chloro |
| 3095 | 3,4-dichloro |
| 3096 | o-methoxy |
| 3097 | p-methoxy |
| 3098 | o-methyl |
| 3099 | m-trifluoromethoxy |
| 3100 | m-trifluoromethyl-p-chloro |
| 3102 | 2,5-dichloro |
| 3103 | 3-chloro-4-fluoro |
| 3104 | 2-fluoro-3-chloro |
| 3105 | o-trifluoromethyl |

Figure 22:
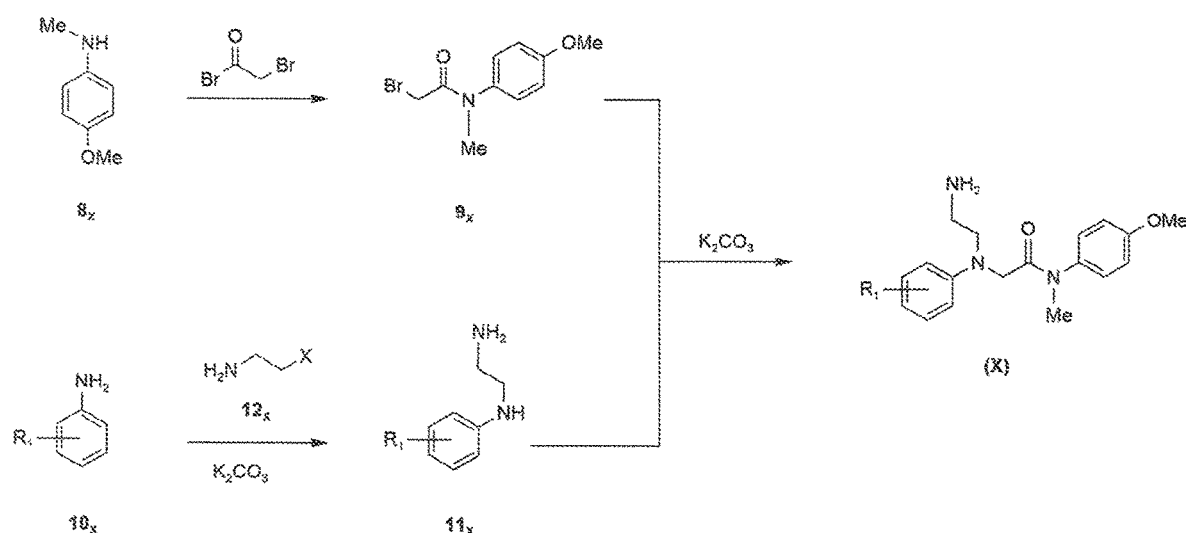
FIG. 22 shows a representative synthetic route for producing compounds of formula (X).

Referring now to FIG. 22, compounds consistent with formula (X) can be synthesized by, for example, acylating para-methoxy-N-methylaniline $8_X$ with bromoacetyl bromide to form intermediate N-bromoacetyl-N-methyl-β-methoxyaniline $9_X$. Intermediates lix can be formed by alkylating $R_1$-substituted anilines $10_X$ with β-haloamines $12_X$ in the presence of base. Combining intermediates $11_X$ with intermediates $9_X$ in the presence of base yields compounds of formula (X).

In other embodiments, the present disclosure provides a compound of formula (XI):

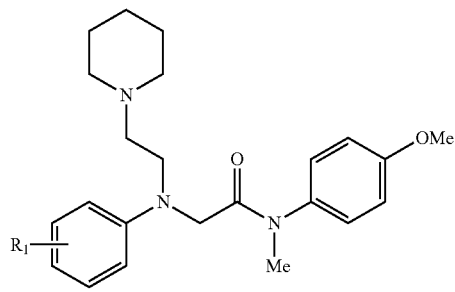

(XI)

wherein $R_1$ is selected from the group consisting of: H, m-chloro; 3,4-dichloro; o-methoxy; β-methoxy; o-methyl; m-trifluoromethoxy; m-trifluoromethyl-β-chloro; 2,5-dichloro; 3-chloro-4-fluoro; 2-fluoro-3-chloro; and o-trifluoromethyl.

Some example compounds of formula (XI) are provided in Table 11 below.

TABLE 11

Example Compounds of Formula (XI)

| Compound | $R_1$ |
|---|---|
| 2303 | H |
| 3106 | m-chloro |
| 3107 | 3,4-dichloro |

TABLE 11-continued

Example Compounds of Formula (XI)

| Compound | $R_1$ |
|---|---|
| 3108 | o-methoxy |
| 3109 | p-methoxy |
| 3110 | o-methyl |
| 3111 | m-trifluoromethoxy |
| 3112 | m-trifluoromethyl-p-chloro |
| 3114 | 2,5-dichloro |
| 3115 | 3-chloro-4-fluoro |
| 3116 | 2-fluoro-3-chloro |
| 3117 | o-trifluoromethyl |

Figure 23:
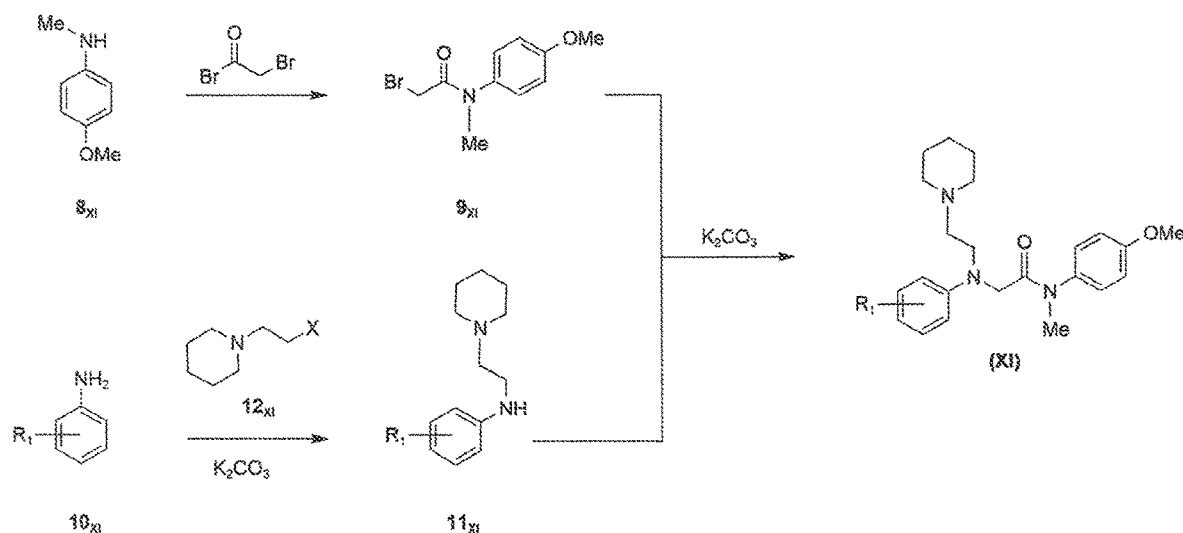
FIG. 23 shows a representative synthetic route for producing compounds of formula (XI).

Referring now to FIG. 23, compounds consistent with formula (XI) can be synthesized by, for example, acylating para-methoxy-N-methylaniline $8_{XI}$ with bromoacetyl bromide to form intermediate N-bromoacetyl-N-methyl-β-methoxyaniline $9_{XI}$. Intermediates $11_{XI}$ can be formed by alkylating $R_1$-substituted anilines $10_{XI}$ with N-(β-haloethyl) piperdine $12_{XII}$ the presence of base. Combining intermediates $11_{XI}$ with intermediates $9_{XII}$ the presence of base yields compounds of formula (XI).

In other embodiments, the present disclosure provides a compound of formula (XII):

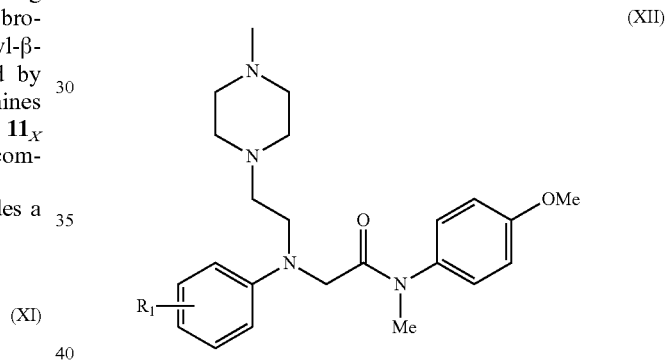

(XII)

wherein $R_1$ is selected from the group consisting of: H, m-chloro; 3,4-dichloro; o-methoxy; β-methoxy; o-methyl; m-trifluoromethoxy; m-trifluoromethyl-β-chloro; 2,5-dichloro; 3-chloro-4-fluoro; 2-fluoro-3-chloro; or o-trifluoromethyl.

Some example compounds of formula (XII) are provided in Table 12 below.

TABLE 12

Example Compounds of Formula (XII)

| Compound | $R_1$ |
|---|---|
| 2304 | H |
| 3118 | m-chloro |
| 3119 | 3,4-dichloro |
| 3120 | o-methoxy |
| 3121 | p-methoxy |
| 3122 | o-methyl |
| 3123 | m-trifluoromethoxy |
| 3124 | m-trifluoromethyl-p-chloro |
| 3126 | 2,5-dichloro |
| 3127 | 3-chloro-4-fluoro |
| 3128 | 2-fluoro-3-chloro |
| 3129 | o-trifluoromethyl |

Figure 24:
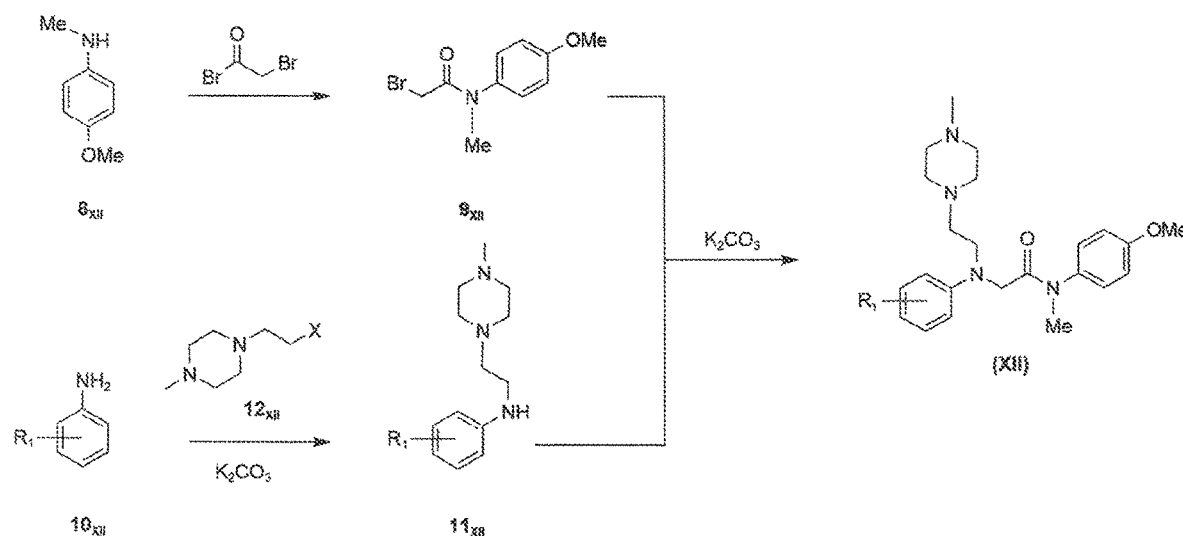
FIG. 24 shows a representative synthetic route for producing compounds of formula (XII).

Referring now to FIG. 24, compounds consistent with formula (XII) can be synthesized by, for example, acylating para-methoxy-N-methylaniline 8$_{XII}$ with bromoacetyl bromide to form intermediate N-bromoacetyl-N-methyl-β-methoxyaniline 9$_{XII}$. Intermediates 11$_{XII}$ can be formed by alkylating R$_1$-substituted anilines 10$_X$ with N-(β-haloethyl)-N'-methylpiperazines 12$_{XIII}$ the presence of base. Combining intermediates 11$_{XII}$ with intermediates 9$_{XIII}$ the presence of base yields compounds of formula (XII).

In other embodiments, the present disclosure provides a compound of formula (XIII):

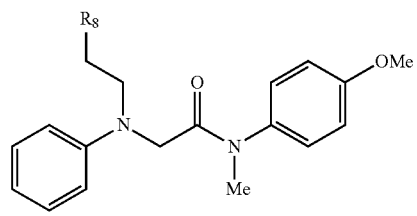

(XIII)

wherein R$_8$ is selected from the group consisting of: NH$_2$, NH(Me), N(Me)$_2$,

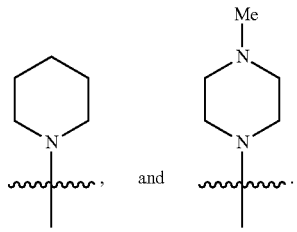 [SMILES: *N1CCCCC1 ; *N1CCN(C)CC1]

Some example compounds of formula (XIII) are provided in Table 13 below.

TABLE 13

| Example Compounds of Formula (XIII) | |
|---|---|
| Compound | R$_8$ |
| 3130 | —NH$_2$ |
| 3131 | —NH(Me) |
| 2290 | —N(Me)$_2$ |
| 2303 | ![piperidine] |
| 2304 | ![N-methylpiperazine] |

Figure 25:
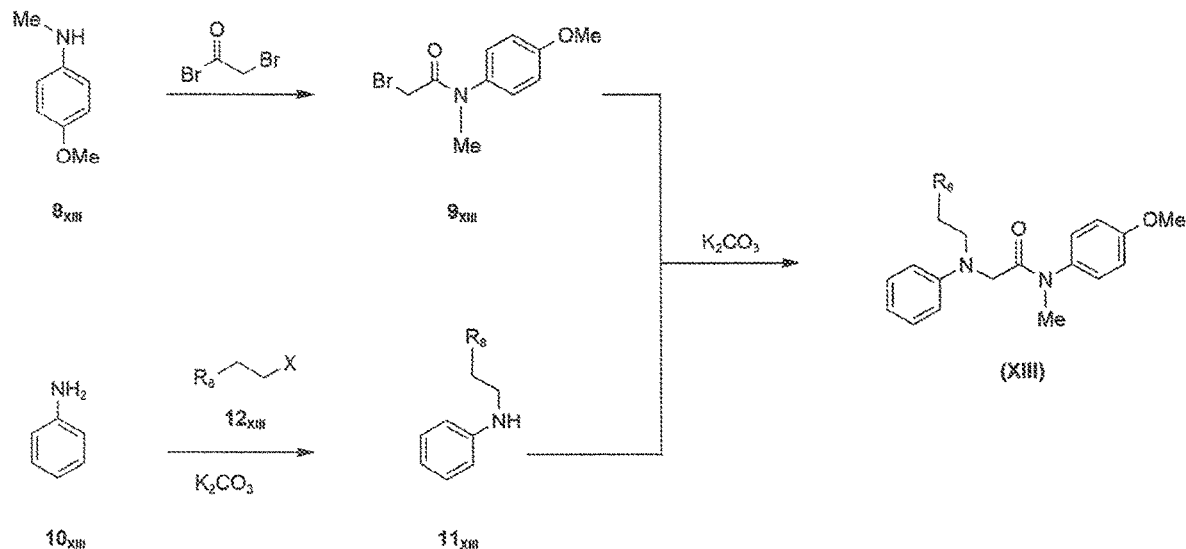
FIG. 25 shows a representative synthetic route for producing compounds of formula (XIII).

Referring now to FIG. 25, compounds consistent with formula (XIII) can be synthesized by, for example, acylating para-methoxy-N-methylaniline 8$_{XIII}$ with bromoacetyl bromide to form intermediate N-bromoacetyl-N-methyl-β-methoxyaniline 9$_{XIII}$. Intermediates 11$_{XIII}$ can be formed by alkylating aniline 10$_{XIII}$ with β-R$_8$-substituted-α-haloethanes 12$_{XIIII}$ the presence of base. Combining intermediates 11$_{XIII}$ with intermediates 9$_{XIII}$ the presence of base yields compounds of formula (XIII).

In other embodiments, the present disclosure provides a compound of formula (XIV):

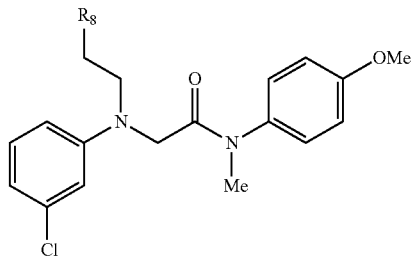

(XIV)

wherein R$_8$ is selected from the group consisting of: NH$_2$, NH(Me), N(Me)$_2$,

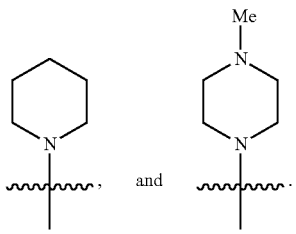 [SMILES: *N1CCCCC1 ; *N1CCN(C)CC1]

Some example compounds of formula (XIV) are provided in Table 14 below.

TABLE 14

| Example Compounds of Formula (XIV) | |
|---|---|
| Compound | R$_8$ |
| 3135 | —NH$_2$ |
| 3136 | —NH(Me) |
| 2291 | —N(Me)$_2$ |
| 3138 | ![piperidine] |
| 3139 | ![N-methylpiperazine] |

Figure 26:
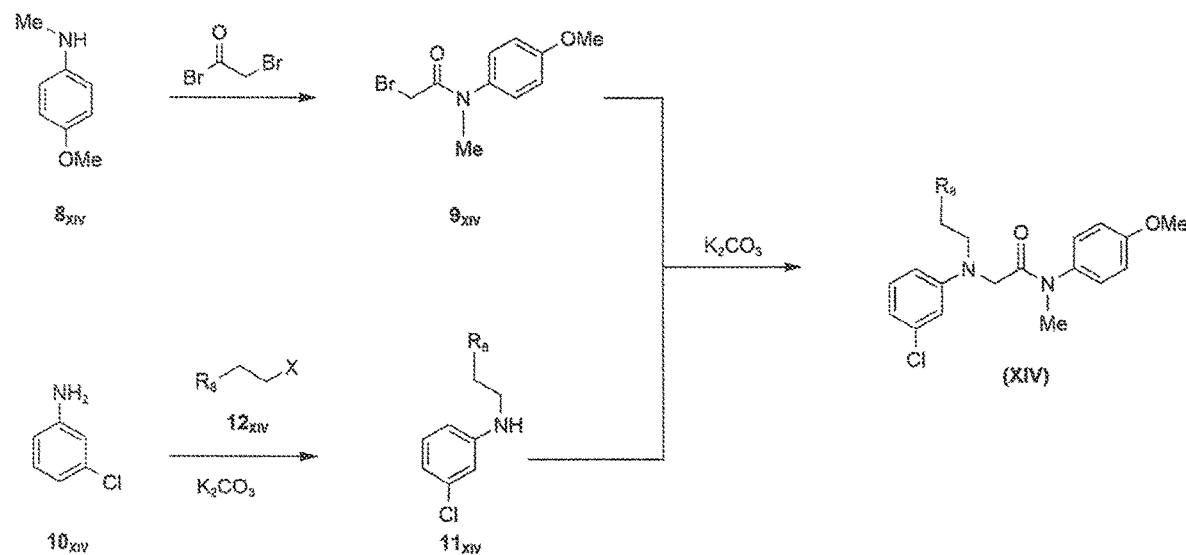
FIG. 26 shows a representative synthetic route for producing compounds of formula (XIV).

Referring now to FIG. 26, compounds consistent with formula (XIV) can be synthesized by, for example, acylating para-methoxy-N-methylaniline 8$_{XIV}$ with bromoacetyl bromide to form intermediate N-bromoacetyl-N-methyl-β-methoxyaniline 9$_{XIV}$. Intermediates 11$_{XIV}$ can be formed by alkylating m-chloroaniline 10$_{XIV}$ with β-R$_8$-substituted-α-haloethanes 12$_{XIV}$ in the presence of base. Combining intermediates 11$_{XIV}$ with intermediates 9$_{XIV}$ in the presence of base yields compounds of formula (XIV).

In other embodiments, the present disclosure provides a compound of formula (XV):

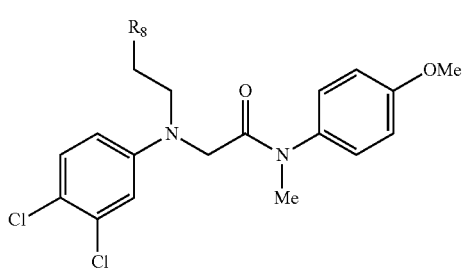

(XV)

wherein R$_8$ is selected from the group consisting of: NH$_2$, NH(Me), N(Me)$_2$,

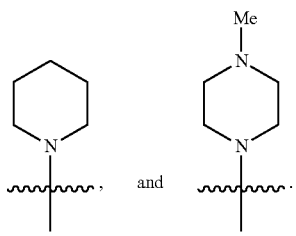 [SMILES: *N1CCCCC1 ; *N1CCN(C)CC1]

Some example compounds of formula (XV) are provided in Table 15 below.

TABLE 15

| Compound | R$_8$ |
|---|---|
| \multicolumn{2}{l}{Example Compounds of Formula (XV)} | |
| 3140 | —NH$_2$ |
| 3141 | —NH(Me) |
| 2292 | —N(Me)$_2$ |
| 3143 | piperidinyl |
| 3144 | 4-methylpiperazinyl |

Figure 27:
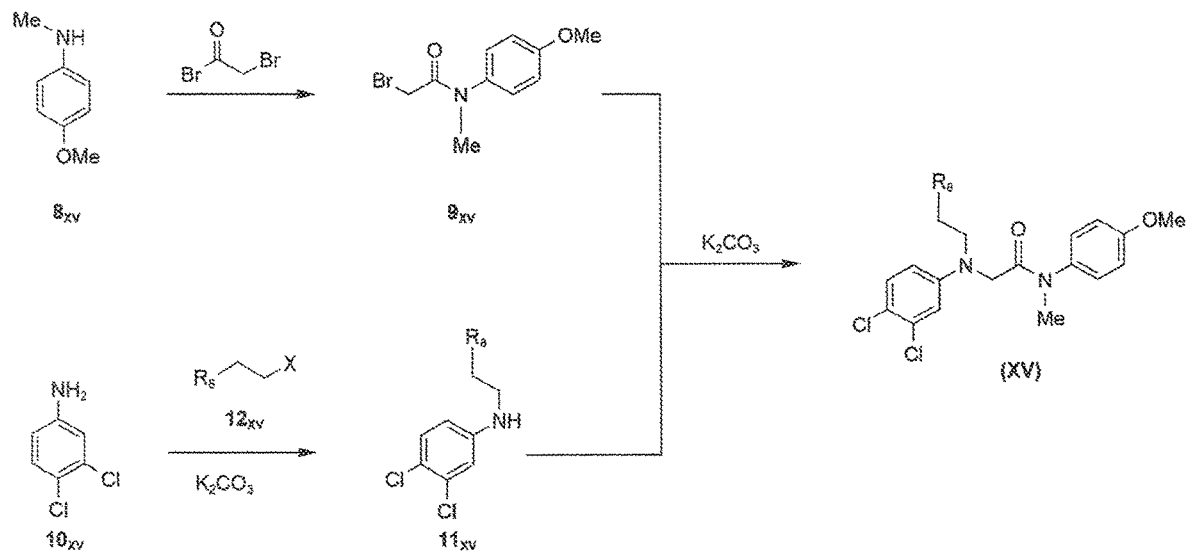
FIG. 27 shows a representative synthetic route for producing compounds of formula (XV).

Referring now to FIG. 27, compounds consistent with formula (XV) can be synthesized by, for example, acylating para-methoxy-N-methylaniline 8$_{XV}$ with bromoacetyl bromide to form intermediate N-bromoacetyl-N-methyl-β-methoxyaniline 9$_{XV}$. Intermediates 11$_{XV}$ can be formed by alkylating 3,4-dichloroaniline 10$_{XV}$ with β-R$_8$-substituted-α-haloethanes 12$_{XV}$ in the presence of base. Combining intermediates 11$_{XV}$ with intermediates 9$_{XV}$ in the presence of base yields compounds of formula (XV).

In other embodiments, the present disclosure provides a compound of formula (XVI):

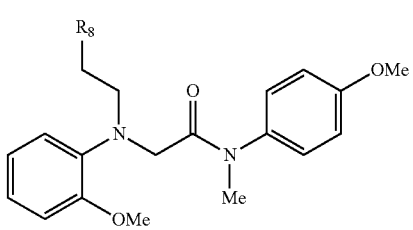

(XVI)

wherein R$_8$ is selected from the group consisting of: NH$_2$, NH(Me), N(Me)$_2$,

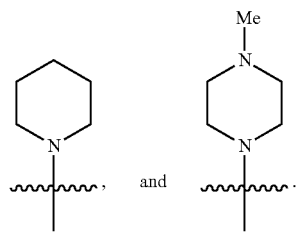 [SMILES: *N1CCCCC1 ; *N1CCN(C)CC1]

Some example compounds of formula (XVI) are provided in Table 16 below.

TABLE 16

| Compound | R$_8$ |
|---|---|
| \multicolumn{2}{l}{Example Compounds of Formula (XVI)} | |
| 3145 | —NH$_2$ |
| 3146 | —NH(Me) |
| 2293 | —N(Me)$_2$ |
| 3148 | piperidinyl |
| 3149 | 4-methylpiperazinyl |

Figure 28:
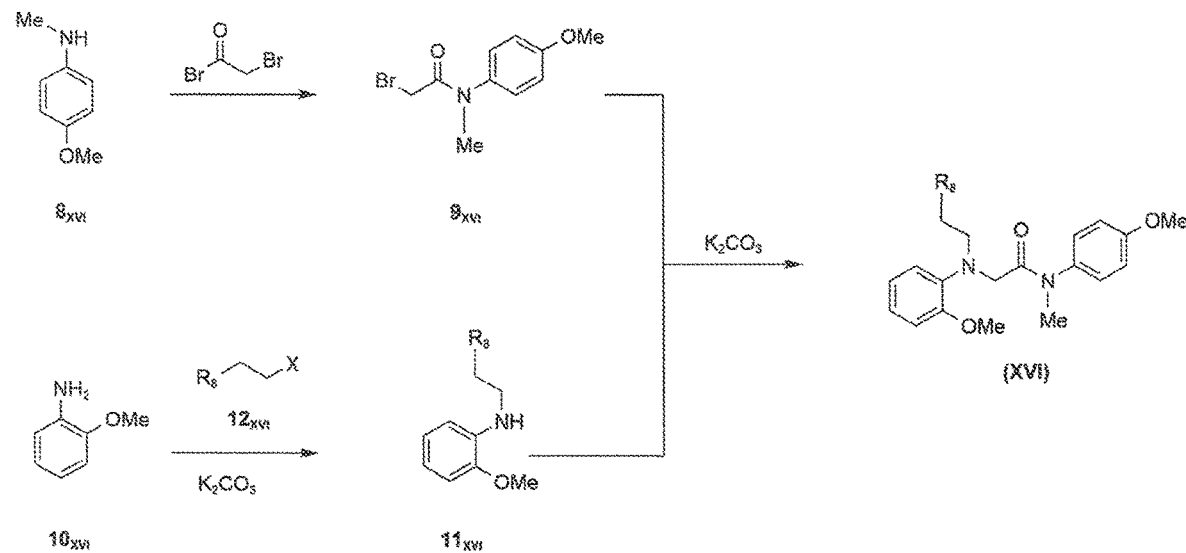
FIG. 28 shows a representative synthetic route for producing compounds of formula (XVI).

Referring now to FIG. 28, compounds consistent with formula (XVI) can be synthesized by, for example, acylating para-methoxy-N-methylaniline 8$XVI$ with bromoacetyl bromide to form intermediate N-bromoacetyl-N-methyl-β-methoxyaniline 9$_{XVI}$. Intermediates 11$XVI$ can be formed by alkylating o-methoxyaniline 10$XVI$ with β-R$_8$-substituted-α-haloethanes 12$_{XVII}$ the presence of base. Combining intermediates 11$XVI$ with intermediates 9$_{XVII}$ the presence of base yields compounds of formula (XVI).

In other embodiments, the present disclosure provides a compound of formula (XVII):

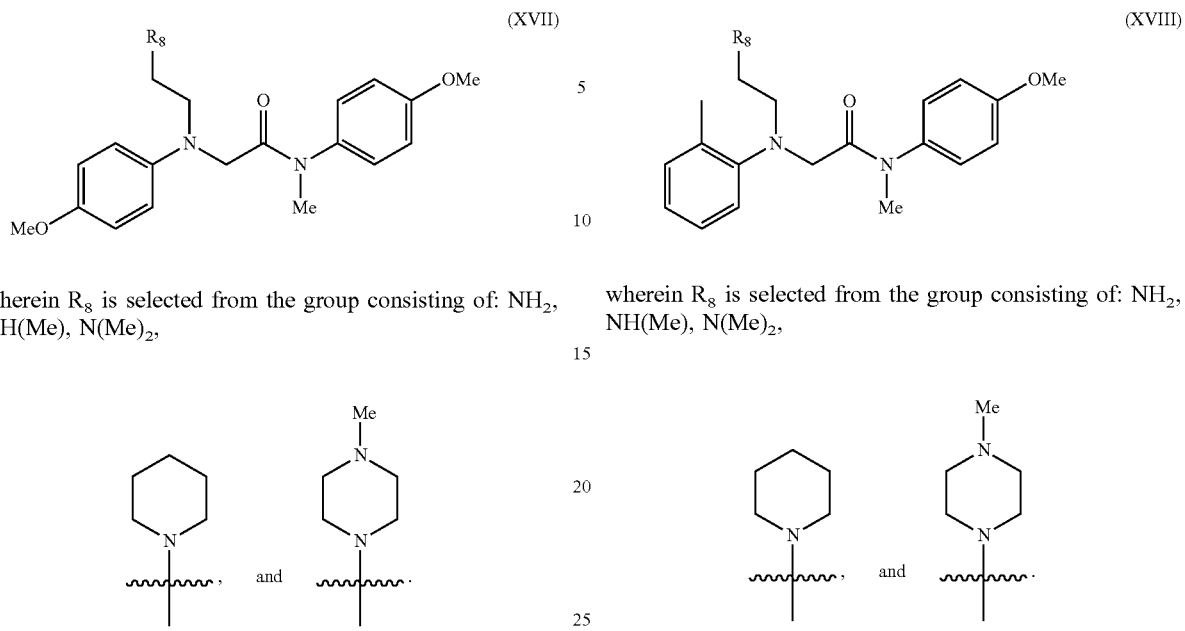

wherein $R_8$ is selected from the group consisting of: $NH_2$, NH(Me), $N(Me)_2$, and wherein $R_8$ is selected from the group consisting of: $NH_2$, NH(Me), $N(Me)_2$, and Some example compounds of formula (XVII) are provided in Table 17 below.

Some example compounds of formula (XVIII) are provided in Table 18 below.

TABLE 17

Example Compounds of Formula (XVII)

| Compound | $R_8$ |
|---|---|
| 3150 | —$NH_2$ |
| 3151 | —NH(Me) |
| 2294 | —$N(Me)_2$ |
| 3153 | (piperidinyl) |
| 3154 | (N-methylpiperazinyl) |

TABLE 18

Example Compounds of Formula (XVIII)

| Compound | $R_8$ |
|---|---|
| 3155 | —$NH_2$ |
| 3156 | —NH(Me) |
| 2295 | —$N(Me)_2$ |
| 3158 | (piperidinyl) |
| 3159 | (N-methylpiperazinyl) |

Figure 29:
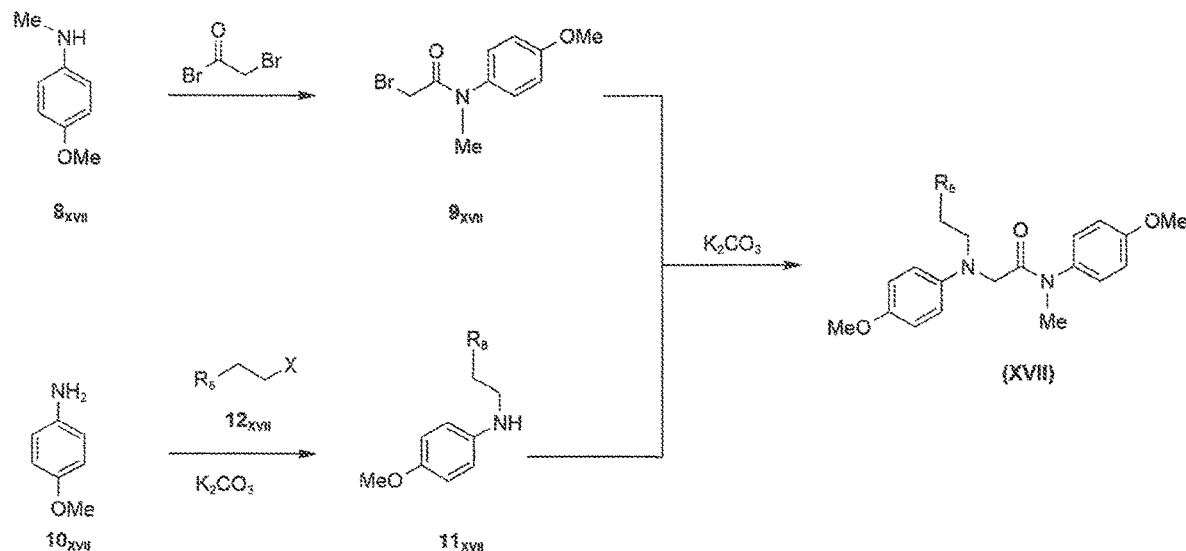
FIG. 29 shows a representative synthetic route for producing compounds of formula (XVII).

Referring now to FIG. 29, compounds consistent with formula (XVII) can be synthesized by, for example, acylating para-methoxy-N-methylaniline 8XVI with bromoacetyl bromide to form intermediate N-bromoacetyl-N-methyl-β-methoxyaniline $9_{XVII}$. Intermediates $11_{XVII}$ can be formed by alkylating β-methoxyaniline 10XVI with β-$R_8$-substituted-α-haloethanes $12_{XVII}$ the presence of base. Combining intermediates 11XVI with intermediates $9_{XVII}$ the presence of base yields compounds of formula (XVII).

Figure 30:
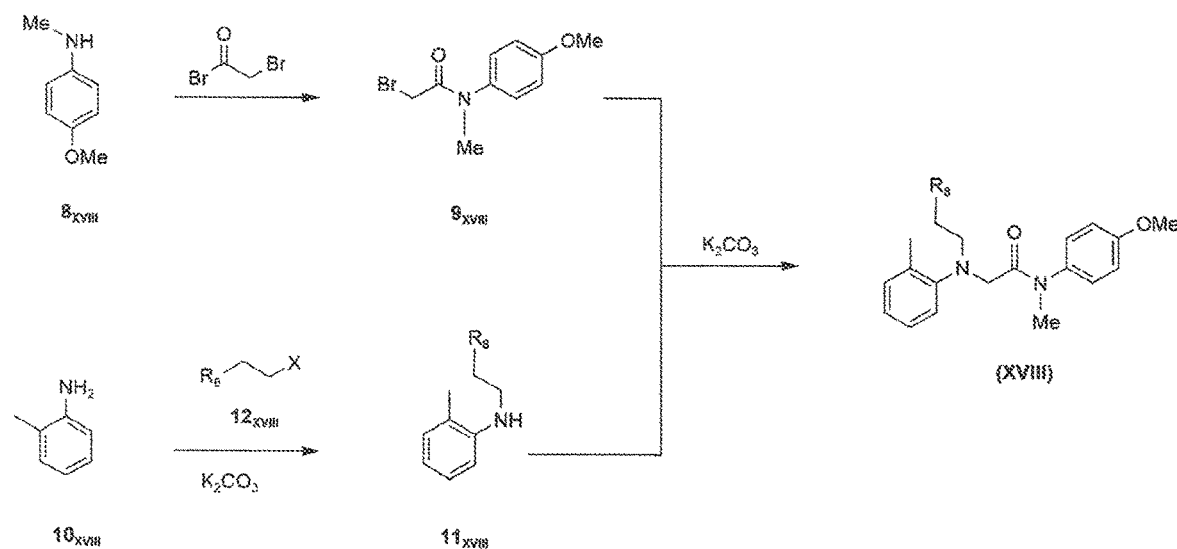
FIG. 30 shows a representative synthetic route for producing compounds of formula (XVIII).

In other embodiments, the present disclosure provides a compound of formula (XVIII):

Referring now to FIG. 30, compounds consistent with formula (XVIII) can be synthesized by, for example, acylating para-methoxy-N-methylaniline $8_{XVIII}$ with bromoacetyl bromide to form intermediate N-bromoacetyl-N-methyl-β-methoxyaniline $9_{XVI}$ m. Intermediates 11XVI can be formed by alkylating o-methylaniline 10XVI (also referred to as o-toluidine or 2-aminotoluene) with β-$R_8$-substituted-α-haloethanes $12_{XVIIII}$ the presence of base. Combining intermediates $11_{XVIII}$ with intermediates $9_{XVIIII}$ the presence of base yields compounds of formula (XVIII).

In other embodiments, the present disclosure provides a compound of formula (XIX):

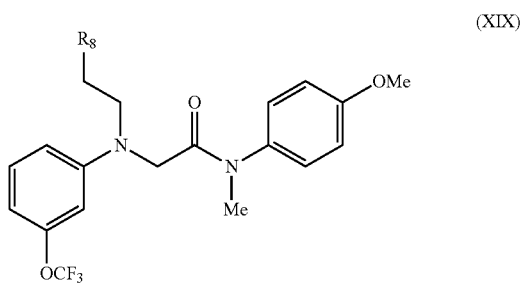

(XIX)

wherein $R_8$ is selected from the group consisting of: $NH_2$, $NH(Me)$, $N(Me)_2$,

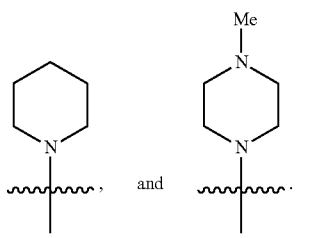 [SMILES: *N1CCCCC1 ; *N1CCN(C)CC1]

Some example compounds of formula (XIX) are provided in Table 19 below.

TABLE 19

Example Compounds of Formula (XIX)

| Compound | $R_8$ |
|---|---|
| 3160 | —$NH_2$ |
| 3161 | —$NH(Me)$ |
| 2296 | —$N(Me)_2$ |
| 3163 | piperidinyl |
| 3164 | 4-methylpiperazinyl |

Figure 31:
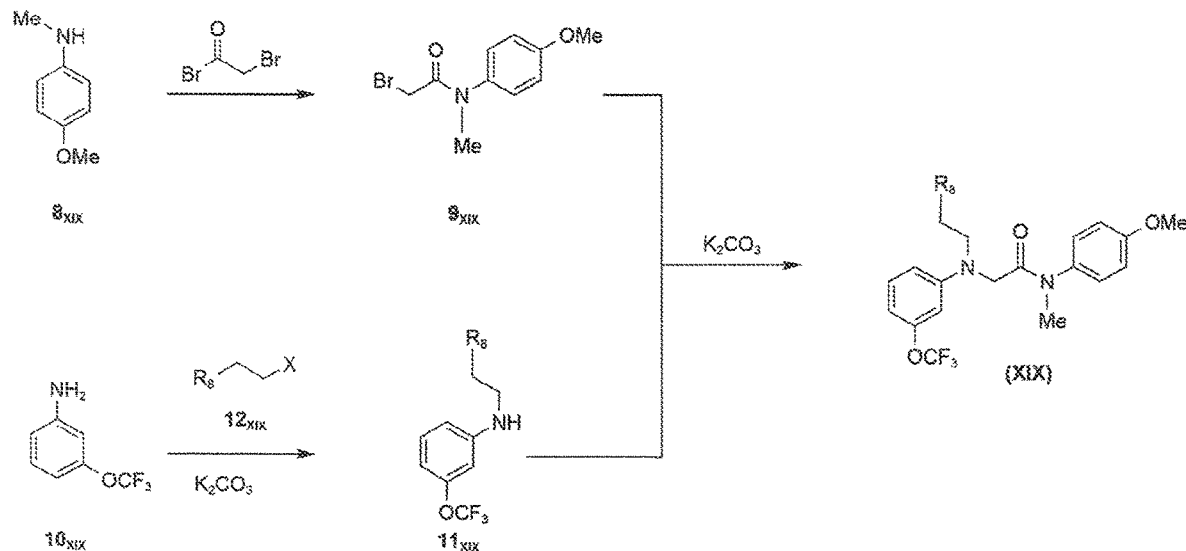
FIG. 31 shows a representative synthetic route for producing compounds of formula (XIX).

Referring now to FIG. 31, compounds consistent with formula (XIX) can be synthesized by, for example, acylating para-methoxy-N-methylaniline $8XIX$ with bromoacetyl bromide to form intermediate N-bromoacetyl-N-methyl-β-methoxyaniline $9_{XIX}$. Intermediates $11XIX$ can be formed by alkylating 3-trifluoromethoxyaniline $10XIX$ with β-$R_8$-substituted-α-haloethanes $12_{XIX}$ in the presence of base. Combining intermediates $11XIX$ with intermediates $9_{XIX}$ in the presence of base yields compounds of formula (XIX).

In other embodiments, the present disclosure provides a compound of formula (XX):

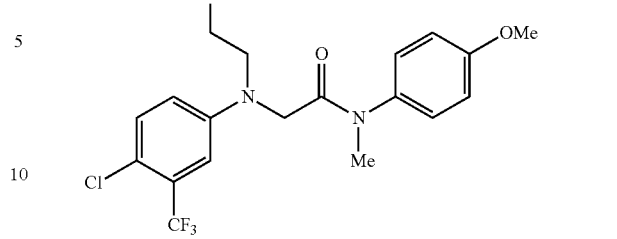

(XX)

wherein $R_8$ is selected from the group consisting of: $NH_2$, $NH(Me)$, $N(Me)_2$,

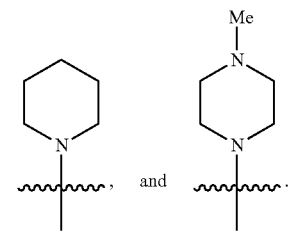 [SMILES: *N1CCCCC1 ; *N1CCN(C)CC1]

Some example compounds of formula (XX) are provided in Table 20 below.

TABLE 20

Example Compounds of Formula (XX)

| Compound | $R_8$ |
|---|---|
| 3165 | —$NH_2$ |
| 3166 | —$NH(Me)$ |
| 2297 | —$N(Me)_2$ |
| 3168 | piperidinyl |
| 3169 | 4-methylpiperazinyl |

Figure 32:
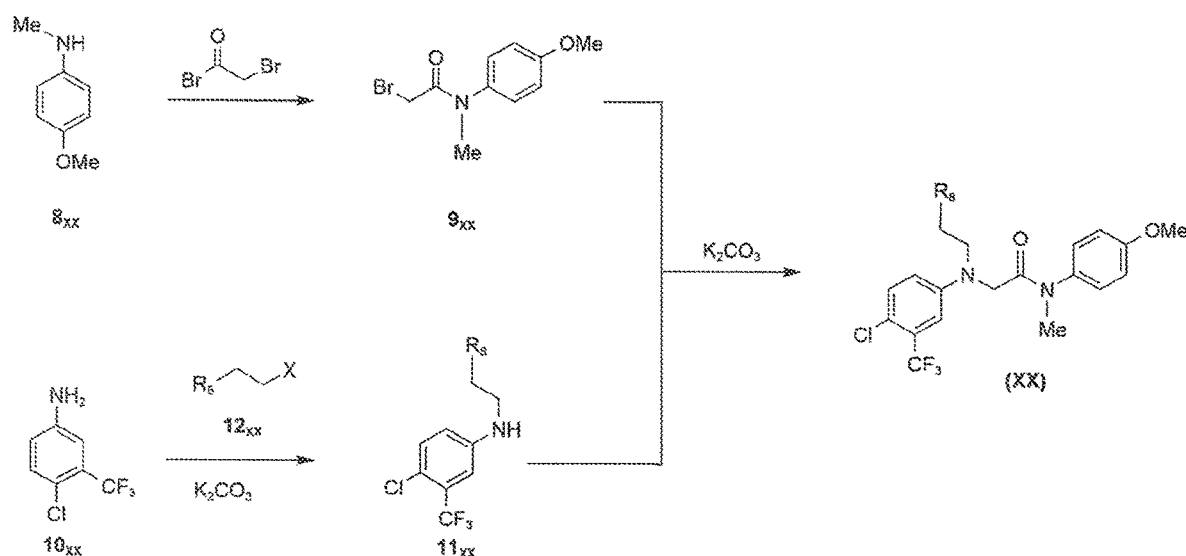
FIG. 32 shows a representative synthetic route for producing compounds of formula (XX).

Referring now to FIG. 32, compounds consistent with formula (XX) can be synthesized by, for example, acylating para-methoxy-N-methylaniline $8_{XX}$ with bromoacetyl bromide to form intermediate N-bromoacetyl-N-methyl-β-methoxyaniline $9_{XX}$. Intermediates $11_{XX}$ can be formed by alkylating 4-chloro-3-trifluoromethylaniline $10_{XX}$ with β-$R_8$-substituted-α-haloethanes $12_{XX}$ in the presence of base. Combining intermediates $11_{XX}$ with intermediates $9_{XX}$ in the presence of base yields compounds of formula (XX).

In other embodiments, the present disclosure provides a compound of formula (XXI):

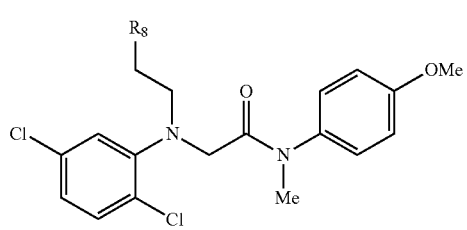

(XXI)

wherein $R_8$ is selected from the group consisting of: $NH_2$, $NH(Me)$, $N(Me)_2$,

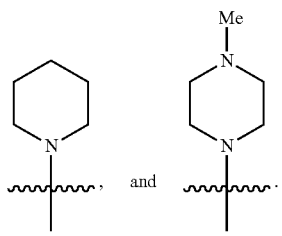 [SMILES: *N1CCCCC1 ; *N1CCN(C)CC1]

Some example compounds of formula (XXI) are provided in Table 21 below.

TABLE 21

Example Compounds of Formula (XXI)

| Compound | $R_8$ |
|---|---|
| 3170 | —$NH_2$ |
| 3171 | —$NH(Me)$ |
| 2298 | —$N(Me)_2$ |
| 3173 | —N(piperidinyl) |
| 3174 | —N(N-methylpiperazinyl) |

Figure 33:
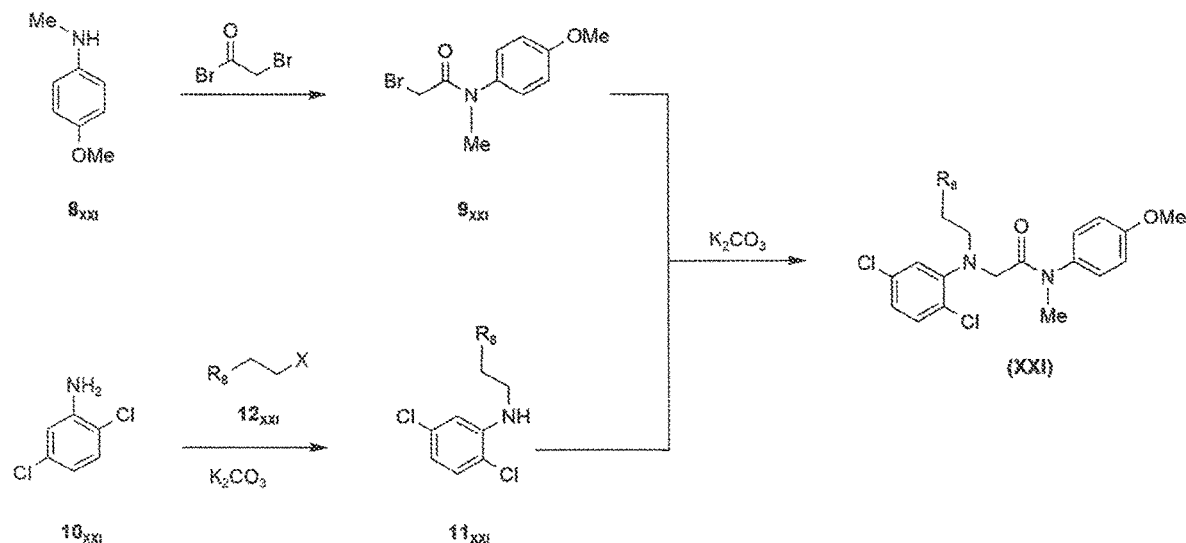
FIG. 33 shows a representative synthetic route for producing compounds of formula (XXI).

Referring now to FIG. 33, compounds consistent with formula (XXI) can be synthesized by, for example, acylating para-methoxy-N-methylaniline $8_{XXI}$ with bromoacetyl bromide to form intermediate N-bromoacetyl-N-methyl-β-methoxyaniline $9_{XXI}$. Intermediates $11_{XXI}$ can be formed by alkylating 2,5-dichloroaniline $10_{XXI}$ with β-$R_8$-substituted-α-haloethanes $12_{XXI}$ the presence of base. Combining intermediates $11XXI$ with intermediates $9_{XXII}$ the presence of base yields compounds of formula (XXI).

In other embodiments, the present disclosure provides a compound of formula (XXII):

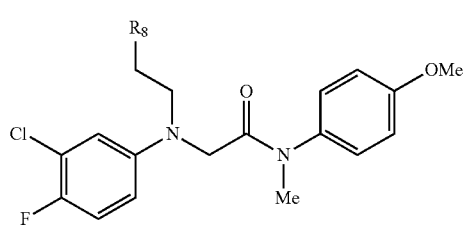

(XXII)

wherein $R_8$ is selected from the group consisting of: $NH_2$, $NH(Me)$, $N(Me)_2$,

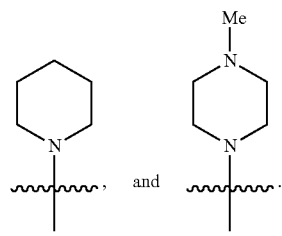 [SMILES: *N1CCCCC1 ; *N1CCN(C)CC1]

Some example compounds of formula (XXII) are provided in Table 22 below.

TABLE 22

Example Compounds of Formula (XXII)

| Compound | $R_8$ |
|---|---|
| 3175 | —$NH_2$ |
| 3176 | —$NH(Me)$ |
| 2299 | —$N(Me)_2$ |
| 3178 | —N(piperidinyl) |
| 3179 | —N(N-methylpiperazinyl) |

Figure 34:
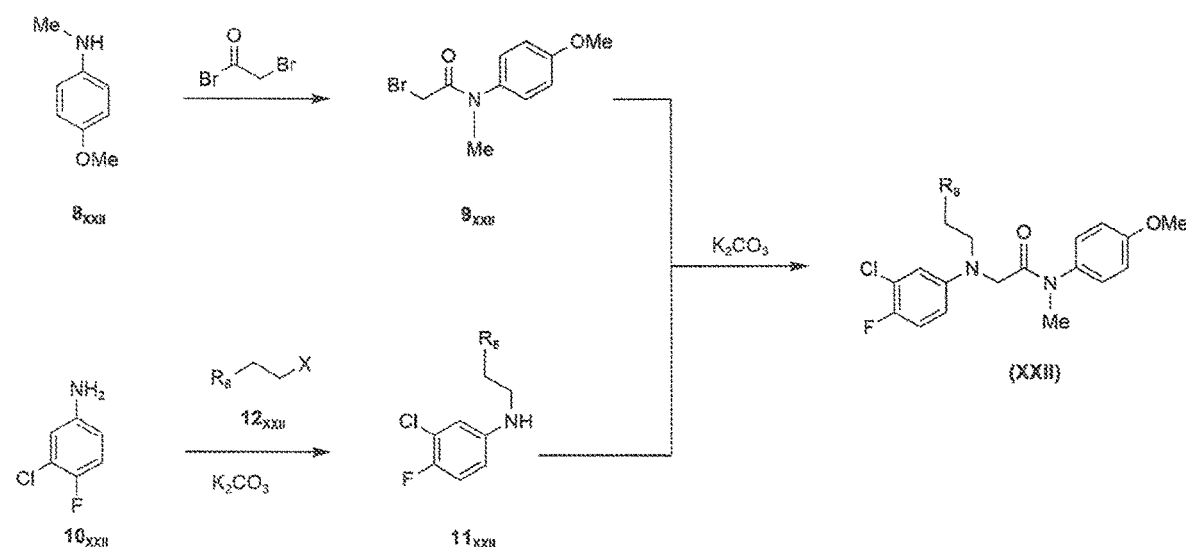
FIG. 34 shows a representative synthetic route for producing compounds of formula (XXII).

Referring now to FIG. 34, compounds consistent with formula (XXII) can be synthesized by, for example, acylating para-methoxy-N-methylaniline $8_{XXI}$ with bromoacetyl bromide to form intermediate N-bromoacetyl-N-methyl-β-methoxyaniline $9_{XXII}$. Intermediates $11_{XXII}$ can be formed by alkylating 3-chloro-4-fluoroaniline $10_{XXI}$ with β-$R_8$-substituted-α-haloethanes $12_{XXII}$ the presence of base. Combining intermediates $11_{XXII}$ with intermediates $9_{XXII}$ in the presence of base yields compounds of formula (XXII).

In other embodiments, the present disclosure provides a compound of formula (XXIII):

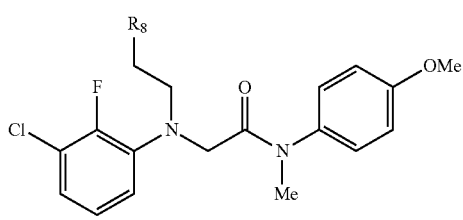

(XXIII)

wherein R₈ is selected from the group consisting of: NH₂, NH(Me), N(Me)₂,

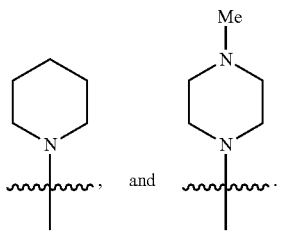 [SMILES: *N1CCCCC1 ; *N1CCN(C)CC1]

Some example compounds of formula (XXIII) are provided in Table 23 below.

TABLE 23

Example Compounds of Formula (XXIII)

| Compound | R₈ |
|---|---|
| 3180 | —NH₂ |
| 3181 | —NH(Me) |
| 2300 | —N(Me)₂ |
| 3183 | ![piperidine] |
| 3184 | ![N-methylpiperazine] |

Figure 35:
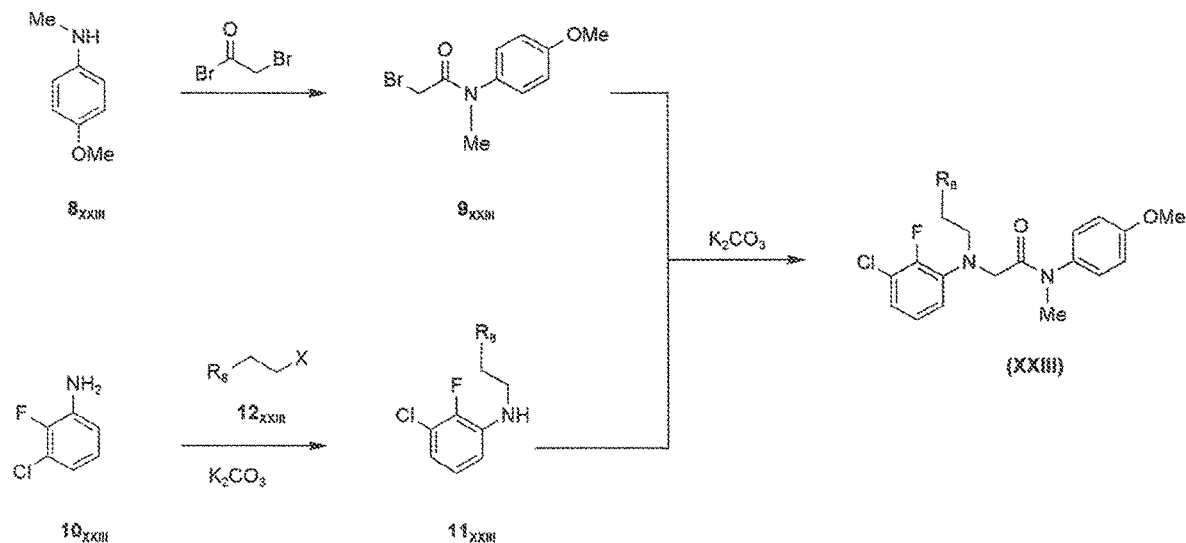
FIG. 35 shows a representative synthetic route for producing compounds of formula (XXIII).

Referring now to FIG. 35, compounds consistent with formula (XXIII) can be synthesized by, for example, acylating para-methoxy-N-methylaniline $8_{XXI}$ with bromoacetyl bromide to form intermediate N-bromoacetyl-N-methyl-β-methoxyaniline $9_{XXIII}$. Intermediates $11_{XXIII}$ can be formed by alkylating 3-chloro-2-fluoroaniline $10_{XXI}$ with β-R₈-substituted-α-haloethanes $12_{XXIII}$ in the presence of base. Combining intermediates $11_{XXIII}$ with intermediates $9_{XX}$ m in the presence of base yields compounds of formula (XXIII).

In other embodiments, the present disclosure provides a compound of formula (XXIV):

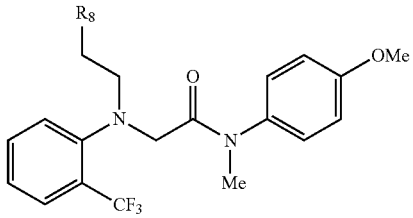

(XXIV)

wherein R₈ is selected from the group consisting of: NH₂, NH(Me), N(Me)₂,

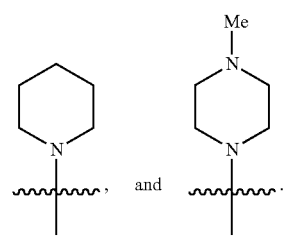 [SMILES: *N1CCCCC1 ; *N1CCN(C)CC1]

Some example compounds of formula (XXIV) are provided in Table 24 below.

TABLE 24

Example Compounds of Formula (XXIV)

| Compound | R₈ |
|---|---|
| 3185 | —NH₂ |
| 3186 | —NH(Me) |
| 2301 | —N(Me)₂ |
| 3188 | ![piperidine] |
| 3189 | ![N-methylpiperazine] |

Figure 36:
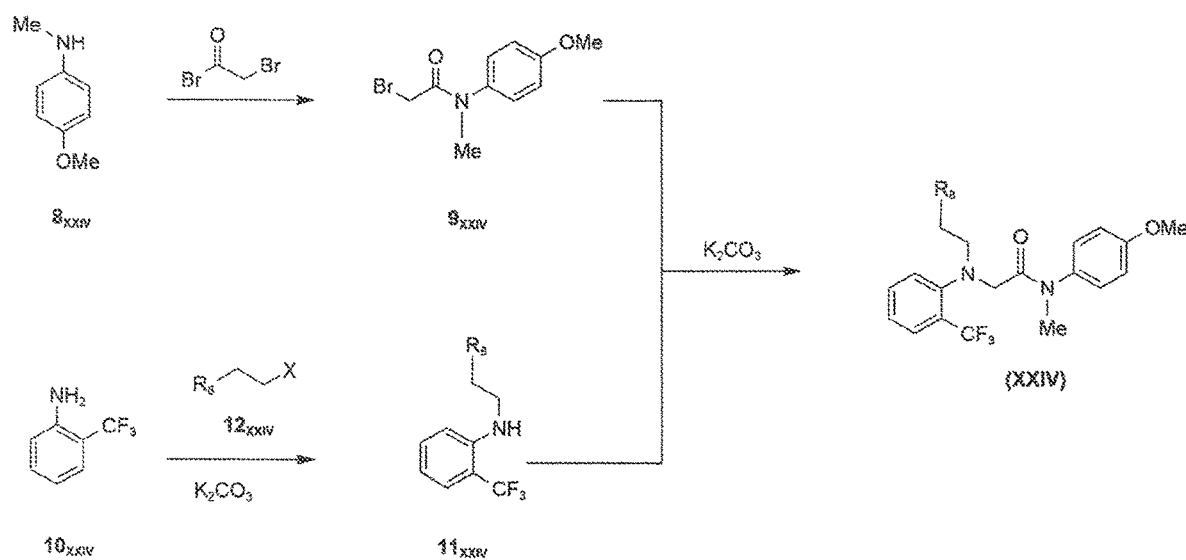
FIG. 36 shows a representative synthetic route for producing compounds of formula (XXIV).

Referring now to FIG. 36, compounds consistent with formula (XXIV) can be synthesized by, for example, acylating para-methoxy-N-methylaniline $8_{XXIV}$ with bromoacetyl bromide to form intermediate N-bromoacetyl-N-methyl-β-methoxyaniline $9_{XXIV}$. Intermediates $11_{XXIV}$ can be formed by alkylating 3-chloro-2-fluoroaniline $10_{XXIV}$ with β-R₈-substituted-α-haloethanes $12_{XXIV}$ in the presence of base. Combining intermediates $11_{XXIV}$ with intermediates $9_{XXIV}$ in the presence of base yields compounds of formula (XXIV).

2. Anesthetic Compositions

The present disclosure provides compositions comprising a compound of any one of formulas (I) to (XXIV). Compositions of the present disclosure may be in any suitable form for delivery to a subject in need thereof, including without limitation topical (cutaneous and transdermal) formulations, injectable (IV, IM, SQ) formulations, intrathecal formulations, oral formulations, sublingual formulations, buccal formulations, otic formulations, ophthalmic formulations, intravesical formulations, rectal formulations, vaginal formulations, inhaled formulations, or nasal formulations.

A) Topical Compositions

Compositions of the present disclosure may be a topical formulation in the form of a lotion, a cream, a gel, a stick, a spray, an ointment, or a paste. In some embodiments, the composition may be applied to skin of the subject using a dispenser. In other embodiments, the composition may be applied to skin of the subject using a dressing, a patch or a pad.

In some embodiments, the compound of any one of formulas (I) to (XXIV) is present in a topical composition in an amount effective to treat perceived pain or to prevent expected pain in a subject after the composition is applied to skin of the subject proximal to the perceived pain or the expected pain. In some embodiments, the compound is present in an amount of about 0.01% w/w to about 5% w/w, in an amount of about 0.05% w/w to about 2% w/w, or in an amount of about 0.1% w/w to about 1% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w.

In some embodiments, the topical composition further comprises a carrier. In some embodiments, the carrier comprises, consists essentially of, or consists of water. In some embodiments, the carrier includes one or more solubilizing agents such as a hydrophobic solvent, an amphipathic solvent, a co-solvent, an emulsifier, a surfactant, etc.

In some embodiments, the topical composition further comprises a penetration enhancer, for example to enhance passage of the compound through skin of the subject. For example and without limitation, a composition of the present disclosure may include a vasodilator.

B) Injectable Formulations

Compositions of the present disclosure may be an injectable formulation in the form of an intravenous formulation, an intramuscular formulation, or a subcutaneous formulation.

In some embodiments, the compound of any one of formulas (I) to (XXIV) is present in an injectable composition in an amount effective to treat perceived pain or to prevent expected pain in a subject after the composition is injected in the subject intravenously, intramuscularly, or subcutaneously. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the injectable composition further comprises a solvent system. The solvent system may include one or more solvents. In some embodiments, the solvent system comprises water (e.g., Water for Injection). In some embodiments, the solvent system comprises, consists essentially of, or consists of water (e.g., Water for Injection). In other embodiments, the solvent system comprises water (e.g., Water for Injection) and a cosolvent, such as polyethylene glycol 300, polyethylene glycol 400, ethanol, propylene glycol, glycerin, N-methyl-2-pyrrolidone, dimethylacetamide, and/or dimethylsulfoxide.

In some embodiments, the injectable composition further comprises a tonicity agent, such as sodium chloride or sodium sulfite.

In some embodiments, the injectable composition comprises a pH adjuster, such as an acid or a base.

In some embodiments, the injectable composition comprises a buffer system to maintain the pH level of the injectable composition within a desired pH range.

In some embodiments, the injectable composition comprises a non-ionic surfactant, such as Cremophor EL, Cremophor RH 40, Cremophor RH 60, d-alpha-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, mono-fatty acid esters of PEG 300, mono-fatty acid esters of PEG 400, mono-fatty acid esters of PEG 1750, di-fatty acid esters of PEG 300, di-fatty acid esters of PEG 400, and/or di-fatty acid esters of PEG 1750.

In some embodiments, the injectable composition comprises a water-insoluble lipid, such as castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and/or medium-chain triglycerides of palm seed oil.

In some embodiments, the injectable composition comprises an organic liquid/semi-solid, such as beeswax, D-α-tocopherol, oleic acid, medium-chain monoglycerides, and/or medium-chain diglycerides.

In some embodiments, the injectable composition comprises a cyclodextrin, such as alpha-cyclodextrin, beta-cyclodextrin, hydroxypropyl-beta-cyclodextrin, and/or sulfobutylether-beta-cyclodextrin.

In some embodiments, the injectable composition comprises a phospholipid, such as hydrogenated soy phosphatidylcholine, distearoylphosphatidylglycerol, L-alpha-dimyristoylphosphatidylcholine, and/or L-alpha-dimyristoylphosphatidylglycerol.

C) Intrathecal Formulations

Compositions of the present disclosure may be an intrathecal formulation in the form of a solution suitable for injection into the spinal cord or into the subarachnoid space.

In some embodiments, the compound of any one of formulas (I) to (XXIV) is present in an intrathecal composition in an amount effective to treat perceived pain or to prevent expected pain in a subject after the composition is provided to the cerebrospinal fluid of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the intrathecal composition further comprises a solvent system. The solvent system may include one or more solvents. In some embodiments, the solvent system comprises water (e.g., Water for Injection). In some embodiments, the solvent system comprises, consists essentially of, or consists of water (e.g., Water for Injection). In other embodiments, the solvent system comprises water (e.g., Water for Injection) and a cosolvent, such as polyethylene glycol 300, polyethylene glycol 400, ethanol, propylene glycol, glycerin, N-methyl-2-pyrrolidone, dimethylacetamide, and/or dimethylsulfoxide.

In some embodiments the osmolality of the intrathecal composition is about 260 mOsm/kg to about 320 mOsm/kg.

In some embodiments, the intrathecal composition further comprises a tonicity agent, such as sodium chloride or sodium sulfite.

In some embodiments, the intrathecal composition comprises a pH adjuster, such as an acid or a base.

In some embodiments, the intrathecal composition comprises a buffer system to maintain the pH level of the intrathecal composition within a desired pH range.

In some embodiments, the intrathecal composition comprises a non-ionic surfactant, such as Cremophor EL, Cremophor RH 40, Cremophor RH 60, d-alpha-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, mono-fatty acid esters of PEG 300, mono-fatty acid esters of PEG 400, mono-fatty acid esters of PEG 1750, di-fatty acid esters of PEG 300, di-fatty acid esters of PEG 400, and/or di-fatty acid esters of PEG 1750.

In some embodiments, the intrathecal composition comprises a water-insoluble lipid, such as castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and/or medium-chain triglycerides of palm seed oil.

In some embodiments, the intrathecal composition comprises an organic liquids/semi-solid, such as beeswax, D-α-tocopherol, oleic acid, medium-chain monoglycerides, and/or medium-chain diglycerides.

In some embodiments, the intrathecal composition comprises a cyclodextrin, such as alpha-cyclodextrin, beta-cyclodextrin, hydroxypropyl-beta-cyclodextrin, and/or sulfobutylether-beta-cyclodextrin.

In some embodiments, the intrathecal composition comprises a phospholipid, such as hydrogenated soy phosphatidylcholine, distearoylphosphatidylglycerol, L-alpha-dimyristoylphosphatidylcholine, and/or L-alpha-dimyristoylphosphatidylglycerol.

D) Oral Formulations

Compositions of the present disclosure may be an oral dosage formulation in the form of a capsule, lozenge, syrup, solution, elixir, emulsion, tincture, decoction, tablet, thin film, or powder.

In some embodiments, the compound of any one of formulas (I) to (XXIV) is present in an oral composition in an amount effective to treat perceived pain or to prevent expected pain in a subject after the composition is ingested by the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the oral composition comprises an outer coating material, such as a polyvinyl alcohol-based film coating system (e.g., the Opadry Clear Coating system 85F190000 further including talc and PEG). When present, the outer coating material may comprise about 4% w/w to about 14% w/w (e.g., about 4% w/w, about 6% w/w, about 8% w/w, about 10% w/w, about 12% w/w, or about 14% w/w) compared to the weight of the oral composition's other components.

In some embodiments, the oral composition comprises a disintegrant, such as alginic acid (Kelacid™, Protacid™, Satialgine H8™), calcium phosphate, tribasic (Tri-Cafos™, TRI-CAL WG™ TRI-TAB™), carboxymethylcellulose calcium (ECG 505™, Nymcel ZSC™) carboxymethylcellulose sodium (Akucell™, Aquasorb™, Blanose™, Finnfix™, Nymcel Tylose CB™), colloidal silicon dioxide (Aerosil™, Cab-O-Sil™, Cab-O-Si™-5P™, Wacker HDK™), croscarmellose sodium (Ac-Di-Sol™, Explocel™, Nymcel ZSX™, Pharmacel XL™, Primellose™ Solutab™, Vivasol™), crospovidone (Kollidon CL™, Kollidon CL-M™, Polyplasdone XL™ Polyplasdone XL-IO™), docusate sodium, guar gum (Galactosol™, Meprogat™, Meyprodor™, Meyprofin™, Meyproguar™), low substituted hydroxypropyl Cellulose, magnesium aluminum silicate (Carrisorb™, Gelsorb™, Magnabite™, Neusilin™, Pharmsorb™, Veegum™) methylcellulose (Benecel™, Culminal MC™, Methocel™, Metolose™), microcrystalline cellulose (Avicel PH™, Celex™, Celphere™, Ceolus KG™, Emcoel™, Ethispheres™, Fibrocel™, Pharmacel™, Tabulose™, Vivapur™), povidone (Kollidon™, Plasdone™) sodium alginate (Kelcosol™, Keltone™, Protanal™), sodium starch glycolate (Explotab™, Primojel™, Vivastar P™) polacrilin potassium (Amberlite IRP88™), silicified microcrystalline cellulose (ProSolv™) starch (Aytex P™, Fluftex W™, Instant Pure-Cote™, Melojel™, Meritena™, Paygel 55™ Perfectamyl D6PH™, Pure-Bind™, Pure-Cote™, Pure-Dent™, Pure-Gel™, Pure-Set™, Purity 21™ Purity 826™, Tablet White™) or pre-gelatinized starch (Instanstarch™, Lycatab C™, Lycatab PGS™, Merigel™, National 78-1551™, Pharma-Gel™, Pee™, Sepistab ST 200™, Spress B820™, Starch 1500 G™, Tablitz™, Unipure LD™ and Unipure WG220™), or mixtures thereof. When present the disintegrant may comprise about 2% w/w to about 16% w/w (e.g., about 2% w/w, about 4% w/w, about 6% w/w, about 8% w/w, about 10% w/w, about 12% w/w, about 14% w/w, or about 16% w/w) of the oral composition's total weight.

In some embodiments, the oral composition comprises a binder, such as acacia, alginic acid (Kelacid™, Protacid™, Satialgine H8™), carbomer (Acritamer™, Carbopol™, Pemulen™ Ultrez™), carboxymethylcellulose sodium (Akucell™, Aquasorb™, Blanose™, Finnfix™, Nymcel™, Tylose™), ceratonia (Meyprofleur™), cottonseed oil, dextrin (Avedex™, Caloreen™, Crystal Gum™, Primogran W™), dextrose (Caridex™, Dextrofm™, Lycedex PF™, Roferose™, Tabfme D-IOO™), gelatin (Cryogel™, Instagel™, Solugel™), guar gum (Galactosol™, Meprogat™, Meyprodor™, Meyprofm™, Meyproguar™), hydrogenated vegetable oil type I (Akofine™ Lubritab™, Sterotex™, Dynasan P[omicron]O™, Softisan 154™, Hydrocote™, Lipovol™, HS-K™, Sterotex HM™), hydroxyethyl cellulose (Alcoramnosan™, Cellosize™, Idroramnosan™ Liporamnosan™, Natrosol™, Tylose PHA™), hydroxyethylmethyl cellulose (Culminal™, Tylopur MH™, Tylopur MHB™, Tylose MB™, Tylose MH™, Tylose MHB™), hydroxypropyl cellulose (Klucel™, Methocel™ Nisso HPC™), low substituted hydroxypropyl cellulose, hypromellose (Benecel MHPC™, Methocel™, Metolose™, Pharmacoat™, Spectracel 6™, Spectracel 15™ Tylopur™), magnesium aluminium silicate (Carrisorb™, Gelsorb™, Magnabite™, Neusilin™ Pharmsorb™, Veegum™), maltodextrin (C*Dry MD™, Glucidex™, Glucodry™, Lycatab DSH™ Maldex™, Maltagran™, Maltrin™, Maltrin QD™, Paselli MD 10 PH™, Star_Dri™) maltose (Advantose 100™) methylcellulose (Benecel™, Culminal MC™, Methocel™, Metolose™) microcrystalline cellulose (Avicel PH™ CelexV™, Celphere™, Ceolus KG™, Emcocel™ Ethispheres™, Fibrocel™, Pharmacel™, Tabulose™, Vivapur™), polydextrose (Litesse™) polyethylene oxide (Polyox™), polymethacrylates (Eastacryl 30D™, Eudragit™, Kollicoat MAE 30D™, Kollicoat MAE 30DP™), povidone (Kollidon™, Plasdone™), sodium alginate (Kelcosol™ Keltone™, Protana™), starch (Aytex P™, Fluftex W™, Instant Pure-Cote™, Melojel™, Meritena Paygel 55™, Perfectamyl D6PH™, Pure-Bind™, Pure-Cote™, Pure-Dent™, Pure-Gel™, Pure-Set™, Purity 21™ Purity 826™, Tablet White™), pregelatinised starch (Instastarch™, Lycatab C™, Lycatab PGS™, Merigel™, National 78-1551™, Pharma-Gel™, Prejel™, Sepistab ST 200™ Spress B820™, Starch 1500 G™, Tablitz™, Unipure LD™, Unipure WG 220™), stearic acid (Crodacid™, Emersol Hystrene™, Industrene™, Kortacid 1895™, Pristerene™), sucrose and zein, or mixtures thereof. When present, the binder may comprise about 0.5% w/w to about 20% w/w (e.g., about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w) of the oral composition's total weight.

In some embodiments, the oral composition comprises a diluent (also referred to as a filler), such as calcium carbonate (Barcroft™, Cal_Carb™, CalciPure™, Destab™, MagGran™, Millicarb™ Pharma-Carb™, Precarb™, Sturcal™, Vivapres Ca™), calcium phosphate, dibasic anhydrous (A-TAB™, Di-Cafos A-N™, Emcompress Anhydrous™, Fujicalin™), calcium phosphate, dibasic dihydrate (Cafos™, Calipharm™ Calstar™, Di-Cafos™, Emcompress™), calcium phosphate tribasic (Tri-Cafos™, TRI-CAL WG™, TRI-TAB™), calcium sulphate (Destab™, Drierite™, Snow White™, Cal-Tab™, Compactrol™, USG Terra Alba™), cellulose powdered (Arbocel™, Elcema™ Sanacel™, Solka-Floc™), silicified microcrystalline cellulose (ProSolv™), cellulose acetate, compressible sugar (Di-Pac™), confectioner's sugar, dextranes (Candex™, Emdex™), dextrin (Avedex™, Caloreen™, Crystal Gum™, Primogran W™), dextrose (Caridex™, Dextrofin™ Lycadex PF™, Roferose™, Tab fine DT-IOO™), fructose (Advantose™, Fructamyl™, Fructofin™ Krystar™), kaolin (Lion™, Sim 90™), lactitol (Finlac ACX™, Finlac DC™, Finlac MCX™), lactose (Aero Flo 20™, Aero Flo 65™, Anhydrox™, CapsuLac™, Fast-Flo™, FlowLac™, GranuLac™ InhaLac™, Lactochem™, Lactohale™, Lactopressr™, Microfine™, Microtose™, Pharmatose™ Prisma Lac™, Respitose™, SacheLac™, SorboLac™, SuperTab™, Tablettose™, Wyndale™ Zeparox™), magnesium carbonate, magnesium oxide (MagGran MO™), maltodextrin (C*Dry MD™, Glucidex™, Glucodry™, Lycatab DSH™, Maldex™, Maltagran™, Maltrin™, Maltrin QD™ Paselli MD 10 PH™, Star_Dri™), maltose (Advantose 100™), mannitol (Mannogem™, Pearlitol™) microcrystalline cellulose (Avicel PH™, Celex™, Celphere™, Ceolus KG™, Emcocel™, Ethispheres™, Fibrocel™, Pharmacel™, Tabulose™, Vivapur™), polydextrose (Litesse™) simethicone (Dow Corning Q7-2243 LVA™, Cow Corning Q7-2587™, Sentry Simethicone™) sodium alginate (Kelcosol™, Keltone™, Protanal™), sodium chloride (Alberger™), sorbitol (Liponec 70-NC™, Liponic 76-NCv, Meritol™, Neosorb™, Sorbifin™, Sorbitol Instant™ Sorbogem™), starch (Aytex P™, Fluftex W™, Instant Pure-Cote™, Melojel™, Meritena Paygel 55™, Perfectamyl D6PH™, Pure-Bind™, Pure-Cote™, Pure-Dent™, Pure-Gel™, Pure-Set™, Purity 21™, Purity 826™, Tablet White™), pregelatinized starch (Instastarch™, Lycatab C™ Lycatab PGS™, Merigel™, National 78-1551™, Pharma-Gel™, Prejel™, Sepistab ST 200™, Spress B820™, Starch 1500 G™, Tablitz™, Unipure LD™, Unipure WG220™), sucrose, trehalose and xylitol (Klinit™, Xylifm™, Xylitab™, Xylisorb™, Xylitolo™), or mixtures thereof. When present, the diluent may comprise up to about 20% w/w (e.g., about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w) of the oral composition's total weight.

In some embodiments, the oral composition comprises a lubricant, such as calcium stearate (HyQual™), glycerine monostearate (Capmul GMS-50™, Cutina GMS™, ImwitorTMl91 and 900, Kessco GMS5™ Lipo GMS™ 410, 450 and 600, Myvaplex 600P™, Myvatex™, Protachem GMS-450™, Rita GMS™, Stepan GMS™, Tegin™, Tegin™503 and 515, Tegin 4100™, Tegin M™ Unimate GMS™), glyceryl behenate (Compritol 888 ATO™), glyceryl palmitostearate (Precirol ATO 5™), hydrogenated castor oil (Castorwax™, Castorwax MP 70™, Castorwax MP 80™ Crodure™, Cutina HR™, Fancol™, Simulsol 1293™), hydrogenated vegetable oil type I (Akofine™, Lubritab™, Sterotex™, Dynasan P60™, Softisan 154™, Hydrocote™, Lipovol HS-K™ Sterotex HM™), magnesium lauryl sulphate, magnesium stearate, medium-chain triglycerides (Captex 300™, Captex 355™, Crodamol GTC/C™, Labrafac CC™, Miglyol 810™, Miglyol 812™ Myritol™, Neobee M5™, Nesatol™, Waglinol 3/9280™), poloxamer (Lutrol™, Monolan™ Pluronic™, SynperOniC™) polyethylene glyCOl (CarbOwaX™, CarbowaX Sentry™, Lipo™, Lipoxol™, Lutrol E™, Pluriol E™), sodium benzoate (Antimol™), sodium chloride (Alberger™) sodium lauryl sulphate (Elfan 240™, Texapon K1 2P™), sodium stearyl fumarate (Pruvr™), stearic acid (Crodacid E570™, Emersol™, Hystrene™, Industrene™, Kortacid 1895™, Pristerene™), talc (Altaic™, Luzenac™, Luzenac Pharma™, Magsil Osmanthus™, Magsil Star™, Superiore™) sucrose stearate (Surfhope SE Pharma D-1803 F™) and zinc stearate (HyQual™), or mixtures thereof. When present, the lubricant may comprise about 0.1% w/w to about 6% w/w (e.g., about 0.1% w/w, about 0.25% w/w, about 0.5% w/w, about 0.75% w/w, about 1% w/w, about 2% w/w, about 3% w/w, about 4% w/w, about 5% w/w, or about 6% w/w) of the oral composition's total weight.

In some embodiments, the oral composition comprises a glidant, such as tribasic calcium phosphate (Tri-Cafos™, TRI-CAL™, TRI-TAB™), CalCium siliCate, Cellulose, powdered (Arbocel™, Elcema™, Sanacel™, Solka-Floc™) colloidal silicon dioxide (Aerosi™, Cab-O-SiI™, Cab-O-Sil M-5P™, Wacker HDK™), magnesium silicate, magnesium trisilicate, starch (Aytex P™, Fluftex W™ Instant Pure-Cote™, Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Altaic™, Luzenac™, Luzenac Pharma™, Magsil Osmanthus™, Magsil Star™, Superiore™), or mixtures thereof. When present, the glidant may comprise about 0.1% w/w to about 4% w/w (e.g., about 0.1% w/w, about 0.25% w/w, about 0.5% w/w, about 0.75% w/w, about 1% w/w, about 2% w/w, about 3% w/w, or about 4% w/w) of the oral composition's total weight.

In some embodiments, the oral composition further comprises an inner protective barrier coating material, such as a methacrylic acid and ethyl acrylate copolymer system (e.g., Acryl-EZE II), a methacrylic acid, methyl methacrylate (1:1) polymer system (e.g., Eudragit L100), a methacrylic acid, methyl methacrylate (1:2) polymer system (e.g., Eudragit S100), or a hydroxypropylmethylcellulose-based film coating system (e.g., the Opadry Complete film coating system 03B28796 additionally including titanium dioxide and PEG). The protective barrier coating material may be present in an amount of about 1% w/w to about 10% w/w (e.g., about 2% w/w or about 4% w/w) of the oral composition weight.

E) Sublingual Formulations

Compositions of the present disclosure may be a sublingual formulation in the form of a sublingual tablet, sublingual strip, soluble sublingual tablet, sublingual drop, sublingual spray, lozenge, or effervescent sublingual tablet.

In some embodiments, the compound of any one of formulas (I) to (XXIV) is present in a sublingual composition in an amount effective to treat perceived pain or to prevent expected pain in a subject after the composition is absorbed by a mucous membrane of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the sublingual composition is a molded sublingual tablet comprising, in addition to an effective amount of a compound of any one of formulas (I) to (XXIV), an excipient such as lactose, dextrose, sucrose, mannitol, finely divided kaolin, calcium carbonate, calcium phosphate, an antioxidant (e.g., sodium bisulfate), a buffer, glucose, sucrose, acacia, povidone, or mixtures of any two or more of the foregoing.

In some embodiments, the sublingual composition is a compressed sublingual tablet comprising, in addition to an effective amount of a compound of any one of formulas (I) to (XXIV), a disintegrant (e.g., a super disintegrant), a lubricant, microcrystalline cellulose, a dry binder, a buffer system, a surface-active agent, a sweetener, a flavorant, a bulking agent (e.g., a sugar-based bulking agent), a saccharide-based material, an effervescent agent, or a mixture of any two or more of the foregoing.

F) Buccal Formulations

Compositions of the present disclosure may be a buccal formulation in the form of a buccal tablet, such as an effervescent buccal tablet.

In some embodiments, the compound of any one of formulas (I) to (XXIV) is present in a buccal composition in an amount effective to treat perceived pain or to prevent expected pain in a subject after the composition is absorbed by a mucous membrane of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the buccal composition further comprises a penetration enhancer, such as a surfactant (e.g., sodium lauryl sulfate, cetyl pyridinium chloride, poloxamer, Brij, Span, Myrj, or Tween), a bile salt (e.g., sodium glycocholate, sodium tauro deoxycholate, or sodium tauro cholate), a fatty acid (e.g., oleic acid, caprylic acid, lauric acid, lyso phosphatidyl choline, or phosphatidyl choline), a cyclodextrin (e.g., α-cyclodextrin, β-cyclodextrin, γ-cyclodextrin, or methylated β-cyclodextrins), a chelator (e.g., EDTA, citric acid, sodium salicylate, or methoxy salicylate), a positively-charged polymer (e.g., chitosan or trimethyl chitosan), or a cationic compound (e.g., poly-L-arginine or L-lysine).

In some embodiments, the buccal composition further comprises an enzyme inhibitor, such as aprotinin, bestatin, puromycin, some bile salts, polyacrylic acid (e.g., carbomer), a chitosan derivative (e.g., chitosan-EDTA), a thiol derivative of polyacrylate, or a thiol derivative of chitosan.

In some embodiments, the buccal composition further comprises a solubility modifier, such as a cyclodextrin (e.g., hydroxylpropyl-β-cyclodextrin) or hydroxylpropyl methyl cellulose.

In some embodiments, the buccal composition further comprises an acid to promote intercellular (paracellular) transport of the compound of formula (I) to (XXIV) across buccal mucosa.

In some embodiments, the buccal composition further comprises a mucoadhesive polymer, such as agarose, chitosan, gelatin, hyaluronic acid, guar gum, hakea gum, xanthan gum, gellan, carragenan, pectin, sodium alginate, a cellulose derivative (e.g., CMC, thiolated CMC, sodium CMC, HEC, HPC, HPMC, or MC), a poly(acrylic acid)-based polymer (e.g., CP, PC, PAA, or a copolymer of acrylic acid and PEG), PVA, PVP, a thiolated polymer (e.g., a thiolated polyacrylates, thiolated chitosan, or deacetylated gellan gum), aminodextran, dimethylaminoethyl (DEAE)-dextran, trimethylated chitosan, chitosan-EDTA, hydroxyethyl starch, poly(ethylene oxide), scleroglucan, cyanoacrylate, a lectin, or a bacterial adhesive agent.

G) Otic Formulations

Compositions of the present disclosure may be an otic formulation in the form of a solution, a suspension, an emulsions, a drop, or a spray.

In some embodiments, the compound of any one of formulas (I) to (XXIV) is present in an otic composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the otic composition further comprises a pH modifier, such as acetic acid, calcium carbonate, citric acid, hydrochloric acid, benzethonium chloride, benzyl alcohol, hydrochloric acid, lactic acid, monopotassium phosphate, sodium acetate, sodium borate, sodium citrate, dibasic sodium phosphate, monobasic sodium diphosphate, sodium hydroxide, sulfuric acid, or tromethamine.

In some embodiments, the otic composition further comprises an antimicrobial preservative, such as aluminum acetate, benzalkonium chloride, benzethonium chloride, benzyl alcohol, boric acid, chlorobutanol, isopropyl alcohol, phenethyl alcohol, methylparaben, potassium metabisulfate, propylparaben, or thiomersal.

In some embodiments, the otic composition further comprises a suspension agent, such as aluminum sulfate, cetyl alcohol, hydroxyethyl cellulose, methylparaben, or polyvinyl alcohol.

In some embodiments, the otic composition further comprises a stabilizing agent, such as creatinine, hydrogenated soybean lecithin, povidone K30, povidone K90, or poloxamer 407.

In some embodiments, the otic composition further comprises an emollient, such as cupric sulfate, glycerol, or polyoxyl 40 stearate.

In some embodiments, the otic composition further comprises a solubilizer, such as polysorbate 20, polysorbate 80, or tyloxapol.

In some embodiments, the otic composition further comprises a tonicity agent, such as sodium chloride or sodium sulfite.

In some embodiments, the otic composition further comprises an ointment base, such as mineral oil, peanut oil, or petrolatum.

H) Ophthalmic Formulations

Compositions of the present disclosure may be an ophthalmic formulation in the form of an eye drop, an ointment, an in situ gel, an insert, a multicompartment drug delivery system, or a bioadhesive formulation.

In some embodiments, the compound of any one of formulas (I) to (XXIV) is present in an ophthalmic composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the ophthalmic composition further comprises a solvent system. The solvent system may include one or more solvents. In some embodiments, the solvent system comprises water (e.g., Water for Injection). In some embodiments, the solvent system comprises, consists essentially of, or consists of water (e.g., Water for Injection). In other embodiments, the solvent system comprises water (e.g., Water for Injection) and a cosolvent, such as polyethylene glycol 300, polyethylene glycol 400, ethanol, propylene glycol, glycerin, N-methyl-2-pyrrolidone, dimethylacetamide, and/or dimethylsulfoxide.

In some embodiments, the ophthalmic composition further comprises a preservative, such as benzyl alcohol.

In some embodiments, the ophthalmic composition further comprises a buffer system configured to maintain the pH level of the composition within a range of about 4 to about 8 (e.g., about 7.4).

n some embodiments, the ophthalmic composition further comprises a viscosity agent to maintain the viscosity of the composition within a range of about 15 mPas to about 150 mPas. When present, the viscosity agent may optionally be a polyvinyl alcohol, a poloxamer (e.g., poloxamer 407), hyaluronic acid, a carbomer, a polysaccharide (e.g., a cellulose derivative, gellan gum, or xanthan gum).

In some embodiments, the ophthalmic composition further comprises a penetration enhancer, such as a chelating agent, a preservative (e.g., benzalkonium chloride), a surfactant, or a bile acid salt. When present, the penetration enhancer should be included in an amount sufficient to improve bioavailability of the compound of any one of formulas (I) to (XXIV) (e.g., in the aqueous humor) without inducing irritation or local tissue toxicity.

In some embodiments, the ophthalmic composition further comprises a solubilizer, such as a cyclodextrin (e.g., 2-hydroxypropyl-β-cyclodextrin). When present, the solubilizer may comprise about 1% w/w to about 15% w/w (e.g., about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w) of the total weight of the composition.

I) Intravesical Formulations

Compositions of the present disclosure may be an intravesical formulation in the form of a nanoparticle, a hydrogel, a dendrimer, or a liposome.

In some embodiments, the compound of any one of formulas (I) to (XXIV) is present in an intravesical composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the intravesical composition further comprises a mucoadhesive system, such as a polymer capable of interacting with urothelial glycosaminoglycans.

In some embodiments, the intravesical composition further comprises a viscosity enhancer, such as a thermosensitive polymer having a relatively low viscosity at low temperature and a gel-like consistency at relatively higher temperature (e.g., TCGel®).

In some embodiments, the intravesical composition further comprises an effervescent (e.g., $CO_2$— or gas-generating) agent, such as sodium bicarbonate, ammonium bicarbonate, or perfluoro pentane.

In some embodiments, the intravesical composition is housed within an intravesical drug reservoir having a pressure responsive valve (e.g., a UROS infusor, Situs Corp.).

In some embodiments, the intravesical composition is housed within an intravesical balloon, which is delivered to the bladder via magnetic or other control device.

In some embodiments, the intravesical composition is housed within a microsphere matrix (e.g., polydimethylsiloxane microspheres), optionally bound together by resorbable suture threads. In such embodiments, the microspheres may be provided to the bladder where the compound of formula (I) to (XXIV) elutes from the microsphere matrix.

In some embodiments, the intravesical composition is housed within a silicon tube, such as a retentive silicon tube-nitinol wire device, that is provided to the bladder (e.g., by catheter) whereafter the compound of formula (I) to (XXIV) elutes from the silicon tube.

In some embodiments, the intravesical composition is housed within a biodegradable elastomer-based device including an osmotic release mechanism. Upon delivery of the device to the bladder, the compound of formula (I) to (XXIV) elutes by osmosis and diffusion.

In some embodiments, the intravesical composition is housed within a U- or helix-shaped PVA matrix. Upon delivery of the PVA matrix to the bladder, the compound of any one of formulas (I) to (XXIV) elutes.

J) Rectal Formulations

Compositions of the present disclosure may be a rectal formulation in the form of a suppository or an enema.

In some embodiments, the compound of any one of formulas (I) to (XXIV) is present in a rectal composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the rectal composition is a suppository and further comprises an excipient system configured to melt at body temperature. In some embodiments, the excipient system comprises an oleaginous base (e.g., cocoa butter, emulsified cocoa butter, hydrogenated oils), a hydrophilic base (e.g., glycerol-gelatin base, soap-glycerine base, or a PEG), an emulsifying base (e.g., Witepsol, massa estarinum, or massuppol).

In some embodiments, the rectal composition is an enema and further comprises a solvent system. The solvent system may include one or more solvents. In some embodiments, the solvent system comprises water (e.g., Water for Injection). In some embodiments, the solvent system comprises, consists essentially of, or consists of water (e.g., Water for Injection). In other embodiments, the solvent system comprises water (e.g., Water for Injection) and a cosolvent, such as polyethylene glycol 300, polyethylene glycol 400, ethanol, propylene glycol, glycerin, N-methyl-2-pyrrolidone, dimethylacetamide, and/or dimethylsulfoxide. In some embodiments, the enema composition further comprises a tonicity agent, such as sodium chloride or sodium sulfite.

K) Vaginal Formulations

Compositions of the present disclosure may be a vaginal formulation in the form of a hydrogel, a vaginal tablet, a pessary, a suppository, a particulate system, or an intravaginal ring.

In some embodiments, the compound of any one of formulas (I) to (XXIV) is present in a vaginal composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the vaginal composition is a hydrogel and further comprises a vehicle, a gelling agent, a humectant, a preservative, and/or a mucoadhesive agent (e.g., hydroxypropylmethyl cellulose).

In some embodiments, the vaginal composition is a pessary and further comprises one or more of: lactose monohydrate, microcrystalline cellulose, lactic acid, maize starch, crospovidone, calcium lactate pentahydrate, magnesium stearate, colloidal anhydrous silica and/or Hypromellose.

In some embodiments, the vaginal composition is a vaginal tablet and further comprises one or more of: a diluent, a binder, a disintegrant, a glidant, a lubricant, and/or an antiadherant.

In some embodiments, the vaginal composition is a particulate system further comprising a polymer matrix in which the compound of any one of formulas (I) to (XXIV) is included. In some embodiments, the matrix comprises a natural polymer such as a polysaccharide, zein, glutein, collagen, gelatin, albumin, or elastin. In some embodiments, the matrix comprises a synthetic biodegradable polymer such as poly(DL-lactic acid), poly(lactic-co-glycolic acid), polycaprolactone, polyacrylates, polymethacrylates, cellulose derivatives, triblock copolymers of poly(ethylene oxide)/poly(propylene oxide) or poloxamers), poly(vinyl alcohol), poly(ethylene glycol), or alginate. In some embodiments, the matrix comprises a synthetic non-biodegradable polymer such as poly(ethyl acrylate-co-methyl methacrylate-co-trimethylammonioethyl methacrylate chloride) (Eudragit® RS 100).

In some embodiments, the vaginal composition is housed in an intravaginal ring matrix comprising polyurethane, ethylene vinyl acetate, silicone, acacia gum, or a copolymer of 2-hydroxyethyl methacrylate and sodium methacrylate.

L) Inhaled Formulations

Compositions of the present disclosure may be an inhaled formulation in the form of a dry powder, an aerosol, or a nebulizable solution.

In some embodiments, the compound of any one of formulas (I) to (XXIV) is present in an inhalable composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the inhalable composition is a dry powder and further comprises an amino acid, a sugar, a stabilizer, a surfactant, and/or a lipid.

In some embodiments, the inhalable composition is an aerosol and further comprises a propellant, a saccharide (e.g., lactose), and/or a co-solvent.

In some embodiments, the inhalable composition is a nebulizable solution further comprising a solvent (e.g., water), a pH adjuster, a buffer system, a starch, a chelator, an emulsifier, a viscosity agent, a tonicity agent, and/or a surfactant.

M) Nasal Formulations

Compositions of the present disclosure may be a nasal formulation in the form of an aqueous solution, an oil, a suspension, an emulsion, or a dry powder.

In some embodiments, the compound of any one of formulas (I) to (XXIV) is present in a nasal composition in an amount effective to treat perceived pain or to prevent expected pain in a subject after the composition is administered to an ear canal of the subject. In some embodiments, the compound is present in an amount of about 0.01% w/w to about 10% w/w, in an amount of about 0.1% w/w to about 8% w/w, in an amount of about 1% w/w to about 6% w/w, or in an amount of about 2% w/w to about 5% w/w. In some embodiments, the compound is present in an amount of about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.1% w/w, about 0.15% w/w, about 0.2% w/w, about 0.25% w/w, about 0.3% w/w, about 0.35% w/w, about 0.4% w/w, about 0.45% w/w, about 0.5% w/w, about 0.55% w/w, about 0.6% w/w, about 0.65% w/w, about 0.7% w/w, about 0.75% w/w, about 0.8% w/w, about 0.85% w/w, about 0.9% w/w, about 0.95% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10 w/w %.

In some embodiments, the nasal composition is an aqueous solution and further comprises a solvent (e.g., water), a pH adjuster, a buffer system, a starch, a chelator, an emulsifier, a viscosity agent, a tonicity agent, and/or a surfactant.

In some embodiments, the nasal composition is an oil and further comprises a solvent (e.g., a hydrophobic liquid), a pH adjuster, a buffer system, a starch, a chelator, an emulsifier, a viscosity agent, a tonicity agent, and/or a surfactant.

In some embodiments, the nasal composition is a suspension and further comprises a solvent (e.g., water), a pH adjuster, a buffer system, a starch, a chelator, an emulsifier, a viscosity agent, a tonicity agent, and/or a surfactant In some embodiments, the nasal composition is an emulsion and further comprises a solvent (e.g., water), a pH adjuster, a buffer system, a starch, a chelator, an emulsifier, a viscosity agent, a tonicity agent, and/or a surfactant.

In some embodiments, the nasal composition is a dry powder and further comprises an amino acid, a sugar, a stabilizer, a surfactant, and/or a lipid.

3. Methods of Treating or Preventing Pain

The present disclosure provides methods of treating or preventing pain in a subject. Generally, methods consistent with the present disclosure comprise administering a composition comprising an effective amount of a compound of any one of formulas (I) to (XXIV) to a subject experiencing pain symptoms or expected to experience pain symptoms.

In some embodiments, the method comprises topically applying a composition of the present disclosure including a compound of any one of formulas (I) to (XXIV) to tissue (e.g., skin) of the subject. In some embodiments, the step of topically applying the composition occurs after the subject observes a pain sensation, and the composition is applied to tissue proximal to the observed pain sensation. In other embodiments, the step of topically applying the composition occurs before the subject observes a pain sensation, and the composition is applied to tissue proximal to a location where a pain sensation is expected to be observed by the subject.

In some embodiments, the method comprises administering a composition of the present disclosure including a compound of any one of formulas (I) to (XXIV) to the subject by injecting the composition intravenously, intramuscularly, or subcutaneously. In some embodiments, the step of administering the composition occurs after the subject observes a pain sensation, and the composition is injected proximal to the observed pain sensation. In other embodiments, the step of administering the composition occurs before the subject observes a pain sensation, and the composition is injected proximal to a location where a pain sensation is expected to be observed by the subject.

In some embodiments, the method comprises administering a composition of the present disclosure including a compound of any one of formulas (I) to (XXIV) to the subject by injecting the composition intrathecally, such as into the spinal cord or into the subarachnoid space of the subject. In some embodiments, the step of administering the composition occurs after the subject observes a pain sensation, and the composition is injected intrathecally proximal to the observed pain sensation. In other embodiments, the step of administering the composition occurs before the subject observes a pain sensation, and the composition is injected intrathecally proximal to a location where a pain sensation is expected to be observed by the subject.

In some embodiments, the method comprises administering a composition of the present disclosure including a compound of any one of formulas (I) to (XXIV) to the subject orally. In some embodiments, the step of administering the composition occurs after the subject observes a pain sensation, and the composition is administered orally to the subject to reduce or eliminate the observed pain. In other embodiments, the step of administering the composition occurs before the subject observes a pain sensation, and the composition is administered orally to the subject to avoid altogether or reduce the severity of pain to be experienced by the subject.

In some embodiments, the method comprises administering a composition of the present disclosure including a compound of any one of formulas (I) to (XXIV) to the subject sublingually. In some embodiments, the step of administering the composition occurs after the subject observes a pain sensation, and the composition is administered sublingually to the subject to reduce or eliminate the observed pain. In other embodiments, the step of administering the composition occurs before the subject observes a pain sensation, and the composition is administered sublingually to the subject to avoid altogether or reduce the severity of pain to be experienced by the subject.

In some embodiments, the method comprises administering a composition of the present disclosure including a compound of any one of formulas (I) to (XXIV) to the subject buccally. In some embodiments, the step of administering the composition occurs after the subject observes a pain sensation, and the composition is administered bucally to the subject to reduce or eliminate the observed pain. In other embodiments, the step of administering the composition occurs before the subject observes a pain sensation, and the composition is administered bucally to the subject to avoid altogether or reduce the severity of pain to be experienced by the subject.

In some embodiments, the method comprises administering a composition of the present disclosure including a compound of any one of formulas (I) to (XXIV) to the subject optically. In some embodiments, the step of administering the composition occurs after the subject observes a pain sensation, and the composition is administered to an ear canal of the subject to reduce or eliminate the observed pain. In other embodiments, the step of administering the composition occurs before the subject observes a pain sensation, and the composition is administered to an ear canal of the subject to avoid altogether or reduce the severity of pain to be experienced by the subject.

In some embodiments, the method comprises administering a composition of the present disclosure including a compound of any one of formulas (I) to (XXIV) to one or both eyes of the subject. In some embodiments, the step of administering the composition occurs after the subject observes a pain sensation, and the composition is administered to one or both eyes of the subject to reduce or eliminate the observed pain. In other embodiments, the step of administering the composition occurs before the subject observes a pain sensation, and the composition is administered to one or both eyes of the subject to avoid altogether or reduce the severity of pain to be experienced by the subject.

In some embodiments, the method comprises administering a composition of the present disclosure including a compound of any one of formulas (I) to (XXIV) to the subject intravesically. In some embodiments, the step of administering the composition occurs after the subject observes a pain sensation, and the composition is administered into the bladder of the subject to reduce or eliminate the observed pain. In other embodiments, the step of administering the composition occurs before the subject observes a pain sensation, and the composition is administered into the bladder of the subject to avoid altogether or reduce the severity of pain to be experienced by the subject.

In some embodiments, the method comprises administering a composition of the present disclosure including a compound of any one of formulas (I) to (XXIV) to the subject rectally. In some embodiments, the step of administering the composition occurs after the subject observes a pain sensation, and the composition is administered rectally to the subject to reduce or eliminate the observed pain. In other embodiments, the step of administering the composition occurs before the subject observes a pain sensation, and the composition is administered rectally to the subject to avoid altogether or reduce the severity of pain to be experienced by the subject.

In some embodiments, the method comprises administering a composition of the present disclosure including a compound of any one of formulas (I) to (XXIV) to the subject vaginally. In some embodiments, the step of administering the composition occurs after the subject observes a pain sensation, and the composition is administered vaginally to the subject to reduce or eliminate the observed pain. In other embodiments, the step of administering the composition occurs before the subject observes a pain sensation, and the composition is administered vaginally to the subject to avoid altogether or reduce the severity of pain to be experienced by the subject.

In some embodiments, the method comprises administering a composition of the present disclosure including a compound of any one of formulas (I) to (XXIV) to the subject via inhalation pathway. In some embodiments, the step of administering the composition occurs after the subject observes a pain sensation, and the composition is administered via inhalation pathway to the subject to reduce or eliminate the observed pain. In other embodiments, the step of administering the composition occurs before the subject observes a pain sensation, and the composition is administered via inhalation pathway to the subject to avoid altogether or reduce the severity of pain to be experienced by the subject.

In some embodiments, the method comprises administering a composition of the present disclosure including a compound of any one of formulas (I) to (XXIV) to the subject nasally. In some embodiments, the step of administering the composition occurs after the subject observes a pain sensation, and the composition is administered nasally to the subject to reduce or eliminate the observed pain. In other embodiments, the step of administering the composition occurs before the subject observes a pain sensation, and the composition is administered nasally to the subject to avoid altogether or reduce the severity of pain to be experienced by the subject.

EXAMPLES

Example 1. Patch Clamp Testing

An examination of the in vitro effects of the compounds consistent with the present disclosure on ion channels $Na_V1.5$ (a sodium voltage-gated channel alpha subunit found predominantly in cardiac muscle cells) and $Na_V1.7$ (a sodium voltage-gated channel alpha subunit normally expressed in high levels in nociceptive pain neurons at dorsal root ganglion (DRG) and trigeminal ganglion and in sympathetic ganglion neurons) was performed using adult epithelial (ovarian) tissue CHO cells of Chinese hamsters (*C. griseus*) transformed with adenovirus 5 DNA and transfected with human ion channel cDNAs (ATCC, Manassas, VA; ChanTest Corp., Cleveland, OH). Cells were cultured in Ham's F-12 medium supplemented with 10% fetal bovine serum, 100 U/mL penicillin G sodium, 100 µg/mL streptomycin sulfate, and 500 µg/mL G418 aminoglycoside antibiotic.

Each compound was analyzed at concentrations of 1000 µM, 300 µM, 100 µM, 30 µM, 10 µM, 3 µM, 1 µM, and 0.3 µM. Lidocaine was included as a positive control at concentrations of 3000 µM, 1000 µM, 300 µM, 100 µM, 30 µM, 10 µM, 3 µM, and 1 µM. All tested compound formulations contained 0.3% DMSO. Each concentration of each compound was loaded into a well of a 384-well polypropylene compound plate using an automated liquid handling system (Integra Assist Plus, Integra) and then placed in the plate well of SyncroPatch 384PE (SP384PE; Nanion Technologies, Livingston, NJ) immediately before application of the cells.

Observed $IC_{50}$ values of the channel current inhibition for each test article are provided in Table 25 ($Na_V1.5$ ion channel inhibition) and Table 26 ($Na_V1.7$ ion channel inhibition).

TABLE 25

Inhibition of $Na_V1.5$ Ion Channel

| Compound | $IC_{50}$, µM | | |
| --- | --- | --- | --- |
|  | TP1A | TP2A | TP25B |
| 2290 | >1000 | >1000 | >1000 |
| 2291 | 808.5 | 740.3 | 692.5 |
| 2292 | 207.7 | 215.7 | 193.1 |
| 2293 | >1000 | >1000 | >1000 |
| 2294 | >1000 | >1000 | >1000 |
| 2295 | >1000 | >1000 | >1000 |
| 2296 | 254.4 | 235.9 | 221.6 |
| 2297 | 95.1 | 91.2 | 72.7 |
| 2298 | 249.4 | 240.3 | 204.0 |
| 2299 | 515.2 | 449.0 | 504.5 |
| 2300 | 327.2 | 307.0 | 259.2 |
| 2301 | 265.3 | 242.5 | 154.0 |
| 2302 | 124.1 | 96.8 | 75.9 |
| 2303 | 16.6 | 13.5 | 9.5 |
| 2304 | >1000 | 880.4 | 670.2 |
| Lidocaine (pos. control) | 453.2 | 15.8 | 68.7 |

TP1A = Tonic Block
TP2A = Inactivated State-Dependent Block
TP25B = Use-Dependent Block

TABLE 26

Inhibition of $Na_V1.7$ Ion Channel

| Compound | $IC_{50}$, µM | | |
| --- | --- | --- | --- |
|  | TP1A | TP2A | TP25B |
| 2290 | >1000 | >1000 | >1000 |
| 2291 | 561.4 | 463.1 | 490.4 |
| 2292 | 164.8 | 162.1 | 166.5 |
| 2293 | >1000 | >1000 | >1000 |
| 2294 | >1000 | >1000 | >1000 |

TABLE 26-continued

Inhibition of Na,1.7 Ion Channel

| Compound | IC$_{50}$, μM | | |
|---|---|---|---|
| | TP1A | TP2A | TP25B |
| 2295 | >1000 | >1000 | >1000 |
| 2296 | 265.4 | 231.2 | 210.5 |
| 2297 | 74.7 | 66.2 | 54.4 |
| 2298 | 272.5 | 228.6 | 220.5 |
| 2299 | 392.6 | 315.0 | 334.3 |
| 2300 | 546.4 | 672.8 | 625.8 |
| 2301 | 312.1 | 275.3 | 235.0 |
| 2302 | 70.2 | 77.9 | 55.4 |
| 2303 | 15.0 | 14.5 | 13.1 |
| 2304 | >1000 | >1000 | >1000 |
| Lidocaine (pos. control) | 407.8 | 23.7 | 112.7 |

TP1A = Tonic Block
TP2A = Inactivated State-Dependent Block
TP25B = Use-Dependent Block

What is claimed is:

1. A compound of formula (VIIIk):

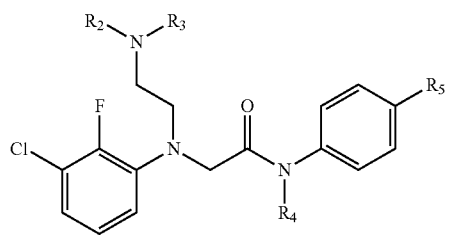

wherein:
R$_2$=H or Me;
R$_3$=H or Me;
R$_4$=Alkyl;
R$_5$=O-Alkyl; and
Alkyl=alphatic C$_1$-C$_4$ alkyl.

2. The compound of claim 1, wherein R$_2$ is H and R$_3$ is H.
3. The compound of claim 1, wherein R$_2$ is H and R$_3$ is methyl.
4. The compound of claim 1, wherein R$_2$ is methyl and R$_3$ is methyl.
5. The compound of claim 1, wherein R$_4$ is methyl.
6. The compound of claim 1, wherein R$_4$ is ethyl.
7. The compound of claim 1, wherein R$_4$ is C$_3$ alkyl.
8. The compound of claim 1, wherein R$_4$ is C$_4$ alkyl.
9. The compound of claim 1, wherein R$_5$ is methoxyl.
10. The compound of claim 1, wherein R$_5$ is ethoxyl.
11. The compound of claim 1, wherein R$_5$ is propoxyl.
12. The compound of claim 1, wherein R$_5$ is butoxyl.
13. The compound of claim 1, wherein:
R$_4$ is methyl; and
R$_5$ is methoxyl.
14. The compound of claim 1, wherein:
at least one of R$_2$ and R$_3$ is methyl; and
R$_4$ is methyl.
15. The compound of claim 1, wherein:
at least one of R$_2$ and R$_3$ is methyl; and
R$_5$ is methoxyl.
16. The compound of claim 1, wherein:
R$_2$ is methyl;
R$_3$ is methyl;
R$_4$ is methyl; and
R$_5$ is methoxyl.

17. A method of treating or preventing pain in a subject, the method comprising administering to the subject an effective amount of a compound of claim 1.
18. The method of claim 17, wherein:
R$_4$ is methyl; and
R$_5$ is methoxyl.
19. The method of claim 17, wherein:
R$_2$ is methyl;
R$_3$ is methyl;
R$_4$ is methyl; and
R$_5$ is methoxyl.
20. A method of making a compound of claim 1, the method comprising:
contacting a compound of formula 8k:

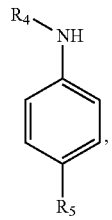

R$_4$=Alkyl,
R$_5$=O-Alkyl, and
Alkyl=alphatic C$_1$-C$_4$ alkyl;
with bromoacetyl bromide to produce a compound of formula 9k:

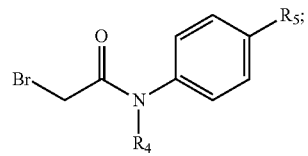

contacting 2-fluoro-3-chloroaniline with a β-haloamine of formula 12k:

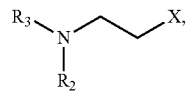

X is halogen,
R$_2$ is H or Me, and
R$_3$ is H or Me,
in the presence of a base to form a compound of formula 11k:

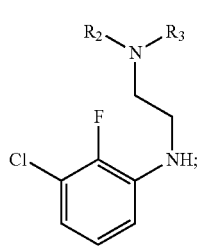 (11k)
contacting the compound of formula 9k with the compound of formula 11k in the presence of a base to form the compound of claim 1.
* * * * *